United States Patent
Kemp et al.

(10) Patent No.: US 11,130,748 B2
(45) Date of Patent: *Sep. 28, 2021

(54) COMPOUNDS

(71) Applicant: MISSION THERAPEUTICS LIMITED, Cambridge (GB)

(72) Inventors: Mark Ian Kemp, Cambridge (GB); Martin Lee Stockley, Cambridge (GB); Andrew Madin, Cambridge (GB)

(73) Assignee: MISSION THERAPEUTICS LIMITED, Cambridge (GB)

( * ) Notice: Subject to any disclaimer, the term of this patent is extended or adjusted under 35 U.S.C. 154(b) by 251 days.

This patent is subject to a terminal disclaimer.

(21) Appl. No.: 15/781,615

(22) PCT Filed: Dec. 16, 2016

(86) PCT No.: PCT/GB2016/053971
§ 371 (c)(1),
(2) Date: Jun. 5, 2018

(87) PCT Pub. No.: WO2017/103614
PCT Pub. Date: Jun. 22, 2017

(65) Prior Publication Data
US 2020/0172516 A1    Jun. 4, 2020

(30) Foreign Application Priority Data
Dec. 17, 2015  (GB) ..................... 1522267

(51) Int. Cl.
| | |
|---|---|
| *A61P 35/00* | (2006.01) |
| *A61P 35/04* | (2006.01) |
| *A61P 25/16* | (2006.01) |
| *A61P 25/28* | (2006.01) |
| *A61P 25/00* | (2006.01) |
| *A61P 25/14* | (2006.01) |
| *A61P 9/00* | (2006.01) |
| *A61P 43/00* | (2006.01) |
| *A61P 3/00* | (2006.01) |
| *A61P 3/10* | (2006.01) |
| *C07D 487/04* | (2006.01) |
| *C07D 413/12* | (2006.01) |
| *C07D 417/12* | (2006.01) |
| *C07D 417/14* | (2006.01) |
| *C07D 403/14* | (2006.01) |

(Continued)

(52) U.S. Cl.
CPC ............ *C07D 403/12* (2013.01); *A61P 25/00* (2018.01); *A61P 35/04* (2018.01); *C07D 403/14* (2013.01); *C07D 413/12* (2013.01); *C07D 417/12* (2013.01); *C07D 471/04* (2013.01); *C07D 487/04* (2013.01)

(58) Field of Classification Search
CPC .......... A61P 21/00; A61P 25/14; A61P 25/00; A61P 25/16; A61P 25/28; A61P 3/10; A61P 3/00; A61P 35/00; A61P 35/04; A61P 9/00; A61P 19/02; A61P 43/00; C07D 487/04; C07D 471/04; C07D 407/09; C07D 401/12; C07D 413/12; C07D 403/12; C07D 403/14; C07D 417/12; C07D 417/14
See application file for complete search history.

(56) References Cited

U.S. PATENT DOCUMENTS 8,227,500 B2    7/2012  Shimizu et al.
10,640,498 B2 *  5/2020  Gibson ................ C07D 401/06
(Continued)

FOREIGN PATENT DOCUMENTS

WO        0177073 A1    10/2001
WO     2013030218 A1     3/2013
(Continued)

OTHER PUBLICATIONS

ALS, 2020, https://alsnewstoday.com/als-treatment/.*
Cancercure, 2020, https://www.healthline.com/health/is-there-a-cure-for-cancer.*
MissionTherapeutics, 2020, https://www.michaeljfox.org/grant/validation-usp30-therapeutic-target-parkinsons-disease-modification.*
MissionTherapeutics-2, 2020, https://missiontherapeutics.com/pipeline/usp30-inhibitor-programs/.*
Pal et al., 2014, Breast Cancer Research, 16:461,7 Pages.*
ParkinsonsCure, 2020, https://www.davisphinneyfoundation.org/blog/why-arent-we-closer-to-finding-a-cure-for-parkinsons/.*
Prasit et al., 2001, caplus an 2001:762966.*
Ward et al., "Quantitative Chemical Proteomic Profiling of Ubiquitin Specific Proteases in Intact Cancer Cells," ACS Chem. Biol. 2016, 11, 3268-3272.
(Continued)

*Primary Examiner* — Sun Jae Yoo

(57) ABSTRACT

The present invention relates to novel compounds and methods for the manufacture of inhibitors of deubiquitylating enzymes (DUBs). In particular, the invention relates to the inhibition of ubiquitin C-terminal hydrolase 30 or Ubiquitin Specific Peptidase 30 (USP30). The invention further relates to the use of DUB inhibitors in the treatment of conditions involving mitochondrial dysfunction and cancer. Compounds of the invention include compounds having the formula (I): (I) or a pharmaceutically acceptable salt thereof, wherein $R^{1a}$, $R^{1b}$, $R^{1c}$, $R^{1d}$, $R^{1e}$, $R^{1f}$, $R^{1g}$, $R^2$, X, L and A are as defined herein.

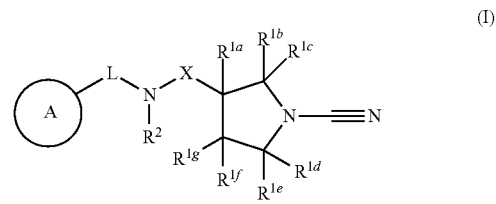

12 Claims, 1 Drawing Sheet

(51) Int. Cl.
    *C07D 207/09*     (2006.01)
    *C07D 471/04*     (2006.01)
    *C07D 401/12*     (2006.01)
    *C07D 403/12*     (2006.01)

(56) References Cited

U.S. PATENT DOCUMENTS

| | | | |
|---|---|---|---|
| 2020/0017480 A1* | 1/2020 | Stockley | A61P 9/10 |
| 2020/0172519 A1* | 6/2020 | Stockley | C07D 403/12 |

FOREIGN PATENT DOCUMENTS

| | | |
|---|---|---|
| WO | 2015179190 A1 | 11/2015 |
| WO | 2016/046530 A1 | 3/2016 |
| WO | 2016156816 A1 | 10/2016 |
| WO | 2017/009650 A1 | 1/2017 |
| WO | 2017/093718 A1 | 6/2017 |
| WO | 2017/109488 A1 | 6/2017 |
| WO | 2017/141036 A1 | 8/2017 |
| WO | 2017/149313 A1 | 9/2017 |
| WO | 2017/158381 A1 | 9/2017 |
| WO | 2017/158388 A1 | 9/2017 |
| WO | 2017/163078 A1 | 9/2017 |
| WO | 2018060689 A1 | 4/2018 |
| WO | 2018060691 A1 | 4/2018 |
| WO | 2018060742 A1 | 4/2018 |
| WO | 2018065768 A1 | 4/2018 |

OTHER PUBLICATIONS

The International Search Report and Written Opinion, dated Jan. 30, 2017, in the corresponding PCT Appl. No PCT/GB2016/053971.

Falgueyret et al., "Novel, Nonpeptidic Cyanamides as Potent and Reversible Inhibitors of Human Cathepsins K and L," J. Med. Chem. 2001, 44, 94-104.

Laine et al., "Discovery of Novel Cyanamide-Based Inhibitors of Cathepsin C," ACS Med. Chem. Lett. 2011, 2, 142-147.

Clague et al., "Deubiquitylases from genes to organism", Physiol. Rev. 93:1289-1315, 2013.

Rydzewski et al., "Peptidic 1-Cyanopyrrolidines: Synthesis and SAR of a Series of Potent, Selective Cathepsin Inhibitors", Bioorganic & Medicinal Chemistry 10 (2002) 3277-3284.

Deaton et al., "Novel and potent cyclic cyanamide-based cathepsin K inhibitors", Bioorganic & Medicinal Chemistry Letters 15 (2005) 1815-1819.

Oballa et al., "A generally applicable method for assessing the electrophilicity and reactivity of diverse nitrile-containing compounds", Bioorganic & Medicinal Chemistry Letters 17 (2007) 998-1002.

Zapf et al, "Covalent Inhibitors of Interleukin-2 Inducible T Cell Kinase (ltk) with Nanomolar Potency in a Whole-Blood Assay", J. Med. Chem. 2012, 55, 10047-10063.

Nakamura et al., "Regulation of Mitochondrial Morphology by USP30, a Deubiquitinating Enzyme Present in the Mitochondrial Outer Membrane", Molecular Biology of the Cell, vol. 19, 1903-1911, May 2008.

Bingol et al., "The mitochondrial deubiquitinase USP30 opposes parkin-mediated mitophagy", Nature vol. 510, 370-375, 2014.

Liang et al., "USP30 deubiquitylates mitochondrial Parkin substrates and restricts apoptotic cell death", EMBO Reports, 1-10, 2015; DOI 10.15252/embr.201439820.

Bedford et al., "Ubiquitin-like protein conjugation and the ubiquitin—proteasome system as drug targets," Nat Rev Drug Discov. Jan. 2011;10(1):29-46.

* cited by examiner

USP30 kinetic assay for high throughput screening of compounds using an isopeptide linked substrate
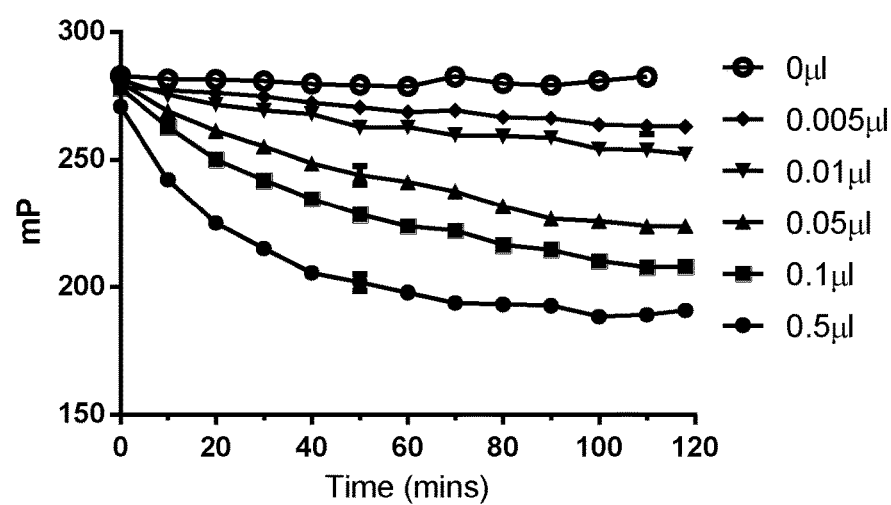

COMPOUNDS

CROSS-REFERENCE TO RELATED APPLICATIONS

This application is a National Stage Application of PCT/GB2016/053971 filed Dec. 16, 2016, which claims priority from UK Patent Application No. 1522267.2, filed on Dec. 17, 2015. The priority of said PCT and UK Patent Application are claimed. Each of the prior mentioned applications is hereby incorporated by reference herein in its entirety.

The present invention relates to novel compounds and methods for the manufacture of inhibitors of deubiquitylating enzymes (DUBs). In particular, the invention relates to the inhibition of ubiquitin C-terminal hydrolase 30 or ubiquitin specific peptidase 30 (USP30). The invention further relates to the use of DUB inhibitors in the treatment of conditions involving mitochondrial dysfunction and in the treatment of cancer.

BACKGROUND TO THE INVENTION

The listing or discussion of an apparently prior-published document in this specification should not necessarily be taken as an acknowledgement that the document is part of the state of the art or is common general knowledge.

Ubiquitin is a small protein consisting of 76 amino acids that is important for the regulation of protein function in the cell. Ubiquitylation and deubiquitylation are enzymatically mediated processes by which ubiquitin is covalently bound or cleaved from a target protein by deubiquitylating enzymes (DUBs), of which there are approximately 95 DUBs in human cells, divided into sub-families based on sequence homology. The USP family are characterised by their common Cys and His boxes which contain Cys and His residues critical for their DUB activities. The ubiquitylation and deubiquitylation processes have been implicated in the regulation of many cellular functions including cell cycle progression, apoptosis, modification of cell surface receptors, regulation of DNA transcription and DNA repair. Thus, the ubiquitin system has been implicated in the pathogenesis of numerous disease states including inflammation, viral infection, metabolic dysfunction, CNS disorders, and oncogenesis (Clague et al., Physiol Rev 93:1289-1315, 2013).

Ubiquitin is a master regulator of mitochondrial dynamics. Mitochondria are dynamic organelles whose biogenesis, fusion and fission events are regulated by the post-translational regulation via ubiquitylation of many key factors such as mitofusins. While ubiquitin ligases such as parkin are known to ubiquitylate a number of mitochondrial proteins, until recently, deubiquitylating enzymes remained elusive. USP30 is a 517 amino acid protein which is found in the mitochondrial outer membrane (Nakamura et al., Mol Biol 19:1903-11, 2008). It is the sole deubiquitylating enzyme bearing a mitochondrial addressing signal and has been shown to deubiquitylate a number of mitochondrial proteins. It has been demonstrated that USP30 opposes parkin-mediated mitophagy and that reduction of USP30 activity can rescue parkin-mediated defects in mitophagy (Bingol et al., Nature 510:370-5, 2014).

Mitochondrial dysfunction can be defined as diminished mitochondrial content (mitophagy or mitochondrial biogenesis), as a decrease in mitochondrial activity and oxidative phosphorylation, but also as modulation of reactive oxygen species (ROS) generation. Hence a role for mitochondrial dysfunctions in a very large number of aging processes and pathologies including but not limited to, neurodegenerative diseases (e.g. Parkinson's disease (PD), Alzheimer's disease, Huntington's disease, Amylotrophic Lateral Sclerosis (ALS), multiple sclerosis), cancer, diabetes, metabolic disorders, cardio-vascular diseases, psychiatric diseases (e.g. Schizophrenia), and osteoarthritis.

For example, Parkinson's disease affects around 10 million people worldwide (Parkinson's Disease Foundation) and is characterised by the loss of dopaminergic neurons in the substantia nigra. The exact mechanisms underlying PD are unclear; however mitochondrial dysfunction is increasingly appreciated as a key determinant of dopaminergic neuronal susceptibility in PD and is a feature of both familial and sporadic disease, as well as in toxin-induced Parkinsonism. Parkin is one of a number of proteins that have been implicated with early onset PD. While most PD cases are linked to defects in alpha-synuclein, 10% of Parkinson's cases are linked to specific genetic defects, one of which is in the ubiquitin E3 ligase parkin. Parkin and the protein kinase PTEN-induced putative kinase 1 (PINK1) collaborate to ubiquitylate mitochondrial membrane proteins of damaged mitochondria resulting in mitophagy. Dysregulation of mitophagy results in increased oxidative stress, which has been described as a characteristic of PD. Inhibition of USP30 could therefore be a potential strategy for the treatment of PD. For example, PD patients with parkin mutations leading to reduced activity could be therapeutically compensated by inhibition of USP30.

It has been reported that depletion of USP30 enhances mitophagic clearance of mitochondria and also enhances parkin-induced cell death (Liang et al., EMBO Reports 2015 DOI: 10.15252/embr.201439820). USP30 has also been shown to regulate BAX/BAK-dependent apoptosis independently of parkin over expression. Depletion of USP30 sensitises cancer cells to BH-3 mimetics such as ABT-737, without the need for parkin over expression. Thus, an anti-apoptotic role has been demonstrated for USP30 and USP30 is therefore a potential target for anti-cancer therapy.

The ubiquitin-proteasome system has gained interest as a target for the treatment of cancer following the approval of the proteasome inhibitor bortezomib (Velcade®) for the treatment of multiple myeloma. Extended treatment with bortezomib is limited by its associated toxicity and drug resistance. However, therapeutic strategies that target specific aspects of the ubiquitin-proteasome pathway upstream of the proteaseome, such as DUBs, are predicted to be better tolerated (Bedford et al., Nature Rev 10:29-46, 2011). Thus, there is a need for compounds and pharmaceutical compositions to inhibit DUBs such as USP30 for the treatment of indications where DUB activity is observed, including, although not limited to, conditions involving mitochondrial dysfunction and cancer.

SUMMARY OF THE INVENTION

In accordance with a first aspect of the invention there is provided a compound of formula (I)

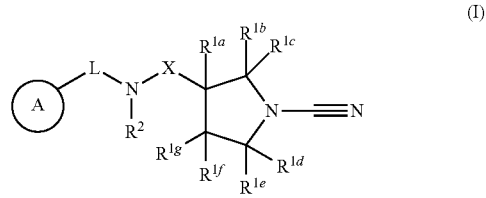

or a pharmaceutically acceptable salt thereof, wherein:
$R^{1b}$, $R^{1c}$, $R^{1d}$, $R^{1e}$ each independently represent hydrogen or an optionally substituted $C_1$-$C_6$ alkyl, or $R^{1b}$ is linked to $R^{1a}$ or $R^{1c}$ to form an optionally substituted cycloalkyl ring, or $R^{1e}$ is linked to $R^{1d}$ or $R^{1f}$ to form an optionally substituted cycloalkyl ring;

$R^{1a}$ and $R^{1g}$ each independently represent hydrogen, fluorine, cyano, hydroxyl, amino, optionally substituted $C_1$-$C_6$ alkyl or optionally substituted $C_1$-$C_6$ alkoxy, or $R^{1a}$ and $R^{1g}$ together form an optionally substituted cycloalkyl ring, or $R^{1a}$ is linked to $R^{1b}$ to form an optionally substituted cycloalkyl ring, or $R^{1g}$ is linked to $R^{1f}$ to form an optionally substituted cycloalkyl ring;

$R^{1f}$ represents hydrogen, fluorine, cyano, hydroxyl, amino, optionally substituted $C_1$-$C_6$ alkyl, optionally substituted $C_1$-$C_6$ alkoxy, or $R^{1f}$ is linked to $R^{1g}$ or $R^{1e}$ to form an optionally substituted cycloalkyl ring, or $R^{1f}$ together with $R^2$ forms an optionally further substituted heterocyclic ring;

$R^2$ represents hydrogen, optionally substituted $C_1$-$C_6$ alkyl or $R^2$ together with $R^{1f}$ forms an optionally further substituted heterocyclic ring;

X is $C(R^3)(R^4)$, wherein $R^3$ and $R^4$ each independently represent hydrogen, cyano, optionally substituted $C_1$-$C_6$ alkyl, a 5 or 6 membered heteroaryl or aryl ring or $R^3$ and $R^4$ together form an optionally substituted 3 to 6 membered heteroalkyl or cycloalkyl ring;

L represents a covalent bond, —SO—, —$SO_2$—, —C(O)—, —C(O)O—, —$CONR^5$—, —$SO_2NR^5$—, —C(O)—$C_1$-$C_6$ alkylene, —C(O)—$C_2$-$C_6$ alkenylene, $C_1$-$C_6$ alkylene-C(O)—, $C_2$-$C_6$ alkenylene-C(O)—, —$C_1$-$C_6$ alkylene-$NR^5CO$—, —$C_1$-$C_6$ alkylene-$CONR^5$—, optionally substituted $C_1$-$C_6$ alkylene or optionally substituted —$C_2$-$C_6$ alkenylene;

A represents a substituted monocyclic heteroaryl or aryl ring or an optionally substituted bicyclic heteroaryl or aryl ring;
$R^5$ represents hydrogen or optionally substituted $C_1$-$C_6$ alkyl.

In one aspect, the invention also relates to pharmaceutical compositions comprising the compounds of the present invention and one or more pharmaceutically acceptable excipients.

In another aspect, the compounds of the invention are useful for the treatment of cancer or a disease or condition involving mitochondrial dysfunction.

BRIEF DESCRIPTION OF THE FIGURES

FIG. 1 is a graph showing proteolytic activity of USP30 measured using a fluorescence polarisation assay. Various volumes of purified USP30 as indicated were incubated with a TAMRA labelled peptide linked to ubiquitin via an isopeptide bond.

DETAILED DESCRIPTION OF THE INVENTION

The definitions and explanations below are for the terms as used throughout this entire document including both the specification and the claims. Reference to compounds as described herein (e.g. a compound of formula (I)), includes reference to formula (I) including any sub-generic embodiments thereof, e.g. formula (IA).

Where any group of the compounds of formula (I) has been referred to as optionally substituted, this group may be substituted or unsubstituted. Substitution may be by one or more of the specified substituents which may be the same or different. It will be appreciated that the number and nature of substituents will be selected to avoid any sterically undesirable combinations.

In the context of the present specification, unless otherwise stated an alkyl, alkylene, alkoxy, alkenyl, or alkynyl substituent (or linker) group or an alkyl, alkenyl moiety in a substituent group may be linear or branched. Alkyl, alkylene and alkenyl chains may also include intervening heteroatoms such as oxygen.

$C_x$-$C_y$ alkyl refers to a saturated aliphatic hydrocarbon group having x-y carbon atoms which may be linear or branched. For example $C_1$-$C_6$ alkyl contains from 1 to 6 carbon atoms and includes $C_1$, $C_2$, $C_3$, $C_4$, $C_5$ and $C_6$. "Branched" means that at least one carbon branch point is present in the group. For example, tert-butyl and isopropyl are both branched groups. Examples of $C_1$-$C_6$ alkyl groups include methyl, ethyl, propyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, tert-butyl, n-pentyl, isopentyl, neopentyl and n-hexyl. $C_1$-$C_6$ alkyl, $C_1$-$C_4$ alkyl and $C_1$-$C_3$ alkyl within the definitions of $R^{1a}$, $R^{1b}$, $R^{1c}$, $R^{1d}$, $R^{1e}$, $R^{1f}$, $R^{1g}$, $R^2$, $R^3$, $R^4$, $R^5$, $R^7$, $R^8$, $R^9$, $R^{10}$, $R^{11}$, $R^{12}$, $Q^1$, and within the definition of substituents for $R^6$, may be unsubstituted or substituted with one or more of the substituents defined herein. Examples of substituted $C_1$-$C_6$ alkyl therefore include $CF_3$, $CH_2CF_3$, $CH_2CN$, $CH_2OH$ and $CH_2CH_2OH$.

A $C_x$-$C_y$ alkylene group or moiety may be linear or branched and refers to a divalent hydrocarbon group having one less hydrogen atom from $C_x$-$C_y$ alkyl as defined above. $C_1$-$C_6$ alkylene may include intervening heteroatoms such as oxygen, and therefore includes alkyleneoxy groups. Alkyleneoxy as employed herein also extends to embodiments in which the or an oxygen atom (e.g. a single oxygen atom) is located within the alkylene chain, for example $CH_2CH_2OCH_2$ or $CH_2OCH_2$. Examples of $C_1$-$C_6$ alkylene groups include methylene, methyleneoxy, ethylene, ethyleneoxy, n-propylene, n-propyleneoxy, n-butylene, n-butyleneoxy, methylmethylene and dimethylmethylene. Unless stated otherwise, $C_1$-$C_6$ alkylene, $C_1$-$C_4$ alkylene and $C_1$-$C_3$ alkylene within the definitions of $R^7$, $R^8$, $R^9$, L, $Q^1$ and $Q^2$ may be unsubstituted or substituted with one or more of the substituents defined herein.

$C_2$-$C_6$ alkenyl refers to a linear or branched hydrocarbon chain radical containing at least two carbon atoms and at least one double bond and includes $C_2$-$C_4$ alkenyl. Examples of alkenyl groups include ethenyl, propenyl, 2-propenyl, 1-butenyl, 2-butenyl, 1-hexenyl, 2-methyl-1-propenyl, 1,2-butadienyl, 1,3-pentadienyl, 1,4-pentadienyl and 1-hexadienyl. Unless stated otherwise, $C_2$-$C_6$ alkenyl within the definitions of $Q^1$ and within the definition of substituents for $R^6$, may be unsubstituted or substituted with one or more of the substituents defined herein.

$C_2$-$C_6$ alkenylene refers to linear or branched hydrocarbon group having one less hydrogen atom from $C_2$-$C_6$ alkenyl as defined above. Examples of $C_2$-$C_6$ alkenylene include ethenylene, propenylene and butenylene. Unless stated otherwise, $C_2$-$C_6$ alkenylene and $C_2$-$C_4$ alkenylene within the definition of substituents for L, $Q^1$ and $Q^2$, may be unsubstituted or substituted with one or more of the substituents defined herein.

$C_2$-$C_6$ alkynyl refers to a linear or branched hydrocarbon chain radical containing at least two carbon atoms and at least one triple bond. Examples of alkenyl groups include ethynyl, propynyl, 2-propynyl, 1-butynyl, 2-butynyl and 1-hexynyl. Unless specified otherwise, $C_2$-$C_6$ alkynyl, within the definitions of $Q^1$ and within the definition of substituents for $R^6$, may be unsubstituted or substituted with one or more of the substituents defined herein.

$C_1$-$C_6$ alkoxy refers to a group or part of a group having an —O—$C_x$-$C_y$ alkyl group according to the definition of $C_x$-$C_y$ alkyl above. $C_1$-$C_6$ alkoxy contains from 1 to 6 carbon atoms and includes $C_1$, $C_2$, $C_3$, $C_4$, $C_5$ and $C_6$. Examples of $C_1$-$C_6$ alkoxy include methoxy, ethoxy, propoxy, iso-propoxy, butoxy, pentoxy and hexoxy. Alkoxy as employed herein also extends to embodiments in which the or an oxygen atom (e.g. a single oxygen atom) is located within the alkyl chain, for example $CH_2CH_2OCH_3$ or $CH_2OCH_3$. Thus the alkoxy may be linked through carbon to the remainder of the molecule, for example, —$CH_2CH_2OCH_3$, or alternatively, the alkoxy is linked through oxygen to the remainder of the molecule, for example —$OC_{1-6}$ alkyl. In one instances, the alkoxy is linked through oxygen to the remainder of the molecule but the alkoxy group contains a further oxygen atom, for example —$OCH_2CH_2OCH_3$. Unless specified otherwise, $C_1$-$C_6$ alkoxy and $C_1$-$C_3$ alkoxy within the definitions $R^{1a}$, $R^{1f}$, $R^{1g}$, $Q^1$, and within the definition of substituents for $R^6$, may be unsubstituted or substituted with one or more of the substituents defined herein. Examples of substituted $C_1$-$C_6$ alkoxy therefore include $OCF_3$, $OCHF_2$, $OCH_2CF_3$, $CH_2CH_2OCH_3$ and $CH_2CH_2OCH_2CH_3$.

The term "halogen" or "halo" refers to chlorine, bromine, fluorine or iodine atoms, in particular chlorine or fluorine atoms.

The term "oxo" means =O.

For the avoidance of doubt it will be understood that the cycloalkyl, heterocyclyl, aryl and heteroaryl rings disclosed herein and within the definitions of $R^{1a}$, $R^{1b}$, $R^{1c}$, $R^{1d}$, $R^{1e}$, $R^{1f}$, $R^{1g}$, $R^2$, $R^3$, $R^4$, $R^6$, $R^{10}$, $R^{11}$, $R^{12}$, ring A, and within the definition of substituents for $R^6$, do not include any unstable ring structures or, in the case of heteroaryl and heterocyclic rings systems, any O—O, O—S or S—S bonds. The ring systems may be monocyclic or bicyclic. Bicyclic ring systems include bridged, fused and spiro ring systems. A substituent if present may be attached to any suitable ring atom which may be a carbon atom or, in the case of heteroaryl and heterocyclic ring systems, a heteroatom. Substitution on a ring may also include a change in the ring atom at the position of the substitution. For example, substitution on a phenyl ring may include a change in the ring atom at the position of substitution from carbon to nitrogen, resulting in a pyridine ring.

"cycloalkyl" refers to a monocyclic saturated or partially unsaturated, non-aromatic ring, wherein all of the ring atoms are carbon, and having the number of ring atoms as indicated. For example $C_3$-$C_{10}$ cycloalkyl refers to a monocyclic or bicyclic hydrocarbon ring containing 3 to 10 carbon atoms. Examples of $C_3$-$C_{10}$ cycloalkyl are cyclopropyl, cyclobutyl, cyclopentyl, cyclohexyl, cycloheptyl, cyclooctyl and decahydronaphthalenyl. Bicyclic cycloalkyl groups include bridged ring systems such as bicycloheptane and bicyclooctane. Unless specified otherwise, cycloalkyl within the definitions of $R^{1a}$, $R^{1b}$, $R^{1c}$, $R^{1d}$, $R^{1e}$, $R^{1f}$, $R^{1g}$, $R^3$, $R^4$, $R^6$, $R^{10}$, $R^{12}$, $R^{13}$, and within the definition of substituents for $R^6$, may be unsubstituted or substituted with one or more of the substituents defined herein.

An "aryl" group/moiety refers to any monocyclic or bicyclic hydrocarbon group comprising at least one aromatic group and having from 5 to 10 carbon atom ring members. Examples of aryl groups include phenyl and naphthyl. Bicyclic rings may be fused aromatic rings where both rings are aromatic, for example, naphthalenyl. Preferred aryl groups are phenyl and naphthyl, more preferably phenyl. Unless specified otherwise, aryl within the definitions of $R^3$, $R^4$, $R^6$, $R^{10}$, $R^{11}$, $R^{12}$, ring A and within the definition of substituents for $R^6$, may be unsubstituted or substituted with one or more of the substituents defined herein.

"Heteroaryl" as used herein means a polyunsaturated, monocyclic or bicyclic 5 to 10 membered aromatic moiety containing at least one and up to 5 heteroatoms, particularly 1, 2 or 3 heteroatoms selected from N, O and S, and the remaining ring atoms are carbon atoms, in stable combinations known to the skilled person. Heteroaryl ring nitrogen and sulphur atoms are optionally oxidised, and the nitrogen atom(s) are optionally quaternized. A heteroaryl ring can be a single aromatic ring or a fused bicyclic ring where the bicyclic ring system can be aromatic, or one of the fused rings is aromatic and the other is at least partially saturated. In one example, a bicyclic heteroaryl is one in which the entire fused ring system is aromatic. Examples of fused rings where one of the rings is aromatic and the other is at least partially saturated include tetrahydropyroidopyrazinyl, tetrahydroquinolinyl and tetrahydroisoquinolinyl. In such instances, attachment of the bicyclic ring to the group it is a substituent of relative to the cyanopyrrolidine core, e.g. $N(R^2)$ via L, is from the aromatic ring of the bicycle. A bicyclic heteroaryl can have the at least one heteroatom in either of the fused rings. For example, a bicyclic ring with an aromatic ring fused to a partially saturated ring may contain the at least one heteroatom in the aromatic ring or the partially saturated ring. Attachment of the bicyclic ring to the group it is a substituent of may be via either a heteroatom containing ring or a carbon only containing ring. The point of attachment of heteroaryl to the group it is a substituent of can be via a carbon atom or a heteroatom (e.g. nitrogen). In instances where ring A is a heteroaryl, the ring is an aromatic ring and may be fused to a further aromatic or partially saturated ring. Examples of heteroaryl rings include pyridinyl, pyrazinyl, pyrimidinyl, pyridazinyl, furyl, pyrrolyl, oxazolyl, thiazolyl, pyrazolyl, triazolyl, tetrazolyl, indolyl, indolizinyl, isoindolyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, triazinyl, dihydrophyridinyl, dihydropyrrolopyridinyl, isoindolinyl, benzoxazolyl, quinoxalinyl, benzomorpholinyl, tetrahydropyridopyrazinyl, tetrahydroqinolinyl and tetrahydroisoquinolinyl. Unless specified otherwise, heteroaryl within the definitions of $R^3$, $R^4$, $R^6$, $R^{10}$, $R^{11}$, $R^{12}$, ring A, and within the definition of substituents for $R^6$, may be unsubstituted or substituted with one or more of the substituents defined herein.

"Heterocyclyl" or "heterocyclic" as used herein in describing a ring means, unless otherwise stated, a monocyclic saturated or partially unsaturated, non-aromatic ring or a bicyclic saturated or partially unsaturated ring, wherein the bicyclic ring system is non-aromatic, the mono- or bicyclic ring having, for example, 3 to 10 members or 5 to 10 members, where at least one member and up to 5 members, particularly 1, 2 or 3 members of the ring are heteroatoms selected from N, O and S, and the remaining ring atoms are carbon atoms, in stable combinations known to those of skill in the art. For example, $R^2$ and $R^3$ may together form a 5 to 7 membered heterocyclic ring which incorporates the amine nitrogen. Heterocyclic ring nitrogen and sulphur atoms are optionally oxidised, and the nitrogen atoms(s) are optionally quaternized. As used herein, the heterocyclic ring may be a fused ring to another ring system to form a bicycle, i.e. one or two of the heterocyclic ring carbons is common to an additional ring system. In instances where the heterocyclcyl is a bicyclic ring, the second ring can be aromatic, e.g. a fused phenyl, pyridyl, pyrazolyl, or the like. The bicyclic heterocyclyl can have at least one heteroatom in either of the fused rings. The heterocyclyl may be linked through carbon or a heteroatom to the remainder of the molecule and in instances where the heterocylyl is a bicyclic ring, the link may be via the heteroatom containing ring or the fused ring. In instances where the heterocyclyl is a bicyclic ring where the second ring is aromatic, attachment of the bicyclic group to the group it is a substituent of relative to the cyanopyrrolidine core is from the non-aromatic ring. Examples of heterocyclyl groups include azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl, benzomorpholinyl and tetrahydroisoquinolinyl. Unless specified otherwise, heterocyclyl within the definitions of $R^{1f}$, $R^2$, $R^3$, $R^4$, $R^6$, $R^{10}$, $R^{11}$, $R^{12}$, and within the definition of substituents for $R^6$, may be unsubstituted or substituted with one or more of the substituents defined herein. Examples of substituted heterocyclyl rings include 4,5-dihydro-1H-maleimido, tetramethylenesulfoxide and hydantoinyl.

"Optionally substituted" as applied to any group means that the said group may if desired be substituted with one or more substituents (e.g., 1, 2, 3 or 4 substituents) which may be the same or different.

Examples of suitable substituents for "substituted" and "optionally substituted" $C_1$-$C_6$ alkyl (including $C_1$-$C_4$ alkyl, $C_1$-$C_3$ alkyl and $C_1$-$C_2$ alkyl) and $C_1$-$C_6$ alkoxy (including $C_1$-$C_4$ alkoxy, $C_1$-$C_3$ alkoxy and $C_1$-$C_2$ alkoxy) and $C_2$-$C_6$ alkenyl (including $C_2$-$C_4$ alkenyl) and $C_2$-$C_6$ alkynyl (including $C_2$-$C_4$ alkynyl), for example within the definitions of $R^{1a}$, $R^{1b}$, $R^{1c}$, $R^{1d}$, $R^{1e}$, $R^{1f}$, $R^{1g}$, $R^2$, $R^3$, $R^4$, $R^5$, $R^7$, $R^8$, $R^9$, $R^{10}$, $R^{11}$, $R^{12}$, $Q^1$, and within the definition of substituents for $R^6$, and $C_1$-$C_6$ alkylene (including $C_1$-$C_3$ alkylene) and $C_2$-$C_6$ alkenylene, for example within the definitions of $R^5$, $R^7$, $R^8$, $R^9$, L, $Q^1$ and $Q^2$, include halogen, hydroxyl, thiol, cyano, amino, nitro and $SF_5$ (a known mimetic of nitro), in particular, halogen (preferably fluorine or chlorine), hydroxyl and cyano.

Examples of suitable substituents for "substituted" and "optionally substituted" rings, i.e. cycloalkyl, heterocyclyl, aryl and heteroaryl rings, for example within the definitions of $R^{1a}$, $R^{1b}$, $R^{1c}$, $R^{1d}$, $R^{1e}$, $R^{1f}$, $R^{1g}$, $R^2$, $R^3$, $R^4$, $R^6$, $R^{10}$, $R^{11}$, $R^{12}$, and within the definition of substituents for $R^6$, include halogen, cyano, oxo, nitro, amino, amide, hydroxy, $C_1$-$C_6$ alkyl or $C_1$-$C_3$ alkyl, $C_1$-$C_6$ alkoxy or $C_1$-$C_3$ alkoxy, aryl, heteroaryl, heterocyclyl, $C_3$-$C_6$ cycloalkyl, $C_{1-3}$ alkylamino, $C_{2-6}$ alkenylamino, di-$C_1$-$C_3$ alkylamino, $C_1$-$C_3$ acylamino, di-$C_1$-$C_3$ acylamino, carboxy, $C_1$-$C_3$ alkoxycarbonyl, carboxamidyl, mono-$C_{1-3}$ carbamoyl, di-$C_{1-3}$ carbamoyl or any of the above in which a hydrocarbyl moiety is itself substituted by halogen, in particular fluorine, hydroxyl, cyano, amino, nitro or $SF_5$ (a known mimetic of nitro). In groups containing an oxygen atom such as hydroxy and alkoxy, the oxygen atom can be replaced with sulphur to make groups such as thio (SH) and thio-alkyl (S-alkyl). Optional substituents therefore include groups such as S-methyl. In thio-alkyl groups, the sulphur atom may be further oxidised to make a sulfoxide or sulfone, and thus optional substituents therefore includes groups such as S(O)-alkyl and $S(O)_2$-alkyl.

Examples of suitable substituents for "substituted" and "optionally substituted" rings include in particular, halogen, oxo, cyano, $C_1$-$C_3$ alkyl, $C_1$-$C_3$ alkoxy, heterocyclyl, cycloalkyl, heteroary or aryl, wherein the alkyl or alkoxy is optionally substituted with one or more (e.g. one, two or three) substituents selected from halogen, hydroxyl, thiol, cyano, amino, nitro and $SF_5$. In particular, suitable substituents for "substituted" and "optionally substituted" rings disclosed herein include fluorine, chlorine, oxo, cyano, $C_1$-$C_3$ alkyl, $C_1$-$C_3$ alkoxy, wherein the alkyl or alkoxy is optionally substituted with one or more (e.g. one, two or three) substituents selected from halogen, hydroxyl, thiol, cyano, amino, nitro and $SF_5$, in particular, one or more fluorine.

Substituted groups thus include for example Br, Cl, F, CN, Me, Et, Pr, Bu, i-Bu, OMe, OEt, OPr, $C(CH_3)_3$, $CH(CH_3)_2$, $CF_3$, $OCF_3$, $C(O)NHCH_3$, cyclopropyl, phenyl, etc. In the case of aryl groups, the substitutions may be in the form of rings from adjacent carbon atoms in the aryl ring, for example cyclic acetals such as O—$CH_2$—O.

The term "treat" or "treating" or "treatment" includes prophylaxis and means to ameliorate, alleviate symptoms, eliminate the causation of the symptoms either on a temporary or permanent basis, or to prevent or slow the appearance of symptoms of the named disorder or condition. The compounds of the invention are useful in the treatment of humans and non-human animals.

The dose of the compound is that amount effective to prevent occurrence of the symptoms of the disorder or to treat some symptoms of the disorder from which the patient suffers. By "effective amount" or "therapeutically effective amount" or "effective dose" is meant that amount sufficient to elicit the desired pharmacological or therapeutic effects, thus resulting in effective prevention or treatment of the disorder. Prevention of the disorder is manifested by delaying the onset of the symptoms of the disorder to a medically significant extent. Treatment of the disorder is manifested by a decrease in the symptoms associated with the disorder or an amelioration of the reoccurrence of the symptoms of the disorder.

Pharmaceutically acceptable salts of the compounds of the invention include but are not limited to addition salts (for example phosphates, nitrates, sulphates, borates, acetates, maleates, citrates, fumarates, succinates, methanesulphonates, benzoates, salicylates and hydrohalides), salts derived from organic bases (such as lithium, potassium and sodium), salts of amino acids (such as glycine, alanine, valine, leucine, isoleucine, cysteine, methionine and proline), inorganic bases (such as triethylamine, hydroxide, choline, thiamine and N—N'-diacetylethylenediamine). Other pharmaceutically acceptable salts include ammonium salts, substituted ammonium salts and aluminium salts. Further pharmaceutically acceptable salts include quaternary ammonium salts of the compounds of the invention.

General methods for the production of salts are well known to the person skilled in the art. Such salts may be formed by conventional means, for example by reaction of a free acid or a free base form of a compound with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound in the form of a salt with another counter-ion, for example using a suitable ion exchange resin.

Where compounds of the invention exist in different enantiomeric and/or diastereoisomeric forms, the invention relates to these compounds prepared as isomeric mixtures or racemates whether present in an optically pure form or as mixtures with other isomers. Enantiomers differ only in their ability to rotate plane-polarized light by equal amounts in opposite directions and are denoted as the (+)/(S) or (−)/(R) forms respectively. Individual enantiomers or isomers may be prepared by methods known in the art, such as optical resolution of products or intermediates (for example chiral chromatographic separation e.g. chiral HPLC, or an asymmetric synthesis approach). Similarly where compounds of the invention exist as alternative tautomeric forms e.g. keto/enol, amide/imidic acid, the invention relates to the individual tautomers in isolation, and to mixtures of the tautomers in all proportions.

Isotopes

The compounds described herein may contain one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. Examples of isotopes include $^2H$, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$ and $^{35}S$.

In an analogous manner, a reference to a particular functional group also includes within its scope isotopic variations, unless the context indicates otherwise. For example, a reference to an alkyl group such as an ethyl group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group).

The isotopes may be radioactive or non-radioactive. In one embodiment, the compounds contain no radioactive isotopes. Such compounds are preferred for therapeutic use. In another embodiment, however, the compounds may contain one or more radioisotopes. Compounds containing such radioisotopes may be useful in a diagnostic context.

Certain isotopically labelled compounds of formula (I), for example, those incorporating a radioactive isotope, are useful in drug and/or substrate tissue distribution studies. The radioactive isotopes i.e. $^3H$ and $^{14}C$ are particularly useful for this purpose in view of their ease of incorporation and ready means of detection. Substitution with heavier isotopes i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining receptor occupancy. Isotopically labelled compounds of formula (I) can generally be prepared by conventional techniques known to those skilled in the art or by processes analogous to those described in the accompanying examples and preparations using an appropriate isotopically labelled reagent in place of the non-labelled reagent previously employed.

Crystalline and Amorphous Forms

The compounds of formula (I) may exist in crystalline or amorphous form and some of the crystalline forms may exist as polymorphs, which are included within the scope of the present invention. Polymorphic forms of compounds of formula (I) may be characterised and differentiated using a number of conventional analytical techniques, including, but not limited to, infra-red spectra, Raman spectra, X-ray powder diffraction, differential scanning calorimetry, thermogravimetric analysis and solid state nuclear magnetic resonance.

Accordingly, in further embodiments, the invention provides a compound according to any described embodiments in a crystalline form. The compound may be from 50% to 100% crystalline, and more particularly is at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline. The compound may alternatively be in an amorphous form.

The invention described herein relates to all crystal forms, solvates and hydrates of any of the disclosed compounds however so prepared. To the extent that any of the compounds disclosed herein have acid or basic centres such as carboxylates or amino groups, then all salt forms of said compounds are included herein. In the case of pharmaceutical uses, the salt should be seen as being a pharmaceutically acceptable salt.

The invention relates to any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent.

Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates. Particular solvates may be hydrates, and examples of hydrates include hemihydrates, monohydrates and dihydrates. For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

The invention relates to pharmaceutically functional derivatives of compounds as defined herein including ester derivatives and/or derivatives that have, or provide for, the same biological function and/or activity as any relevant compound of the invention. Thus, for the purposes of this invention, the term also includes prodrugs of compounds as defined herein.

The term "prodrug" of a relevant compound includes any compound that, following oral or parenteral administration, is metabolised in vivo to form that compound in an experimentally-detectable amount, and within a predetermined time (e.g. within a dosing interval of between 6 and 24 hours (i.e. once to four times daily).

Prodrugs of compounds may be prepared by modifying functional groups present on the compound in such a way that the modifications are cleaved, in vivo when such prodrug is administered to a mammalian subject. The modifications typically are achieved by synthesizing the parent compound with a prodrug substituent. Prodrugs include compounds wherein a hydroxyl, amino, sulfhydryl, carboxyl or carbonyl group in a compound is bonded to any group that may be cleaved in vivo to regenerate the free hydroxyl, amino, sulfhydryl, carboxyl or carbonyl group, respectively.

Examples of prodrugs include, but are not limited to, esters and carbamates of hydroxyl functional groups, ester groups of carboxyl functional groups, N-acyl derivatives and N-Mannich bases. General information on prodrugs may be found e.g. in Bundegaard, H. "Design of Prodrugs" p. 1-92, Elsevier, New York-Oxford (1985).

Compounds of the invention may be metabolised in vivo. Metabolites of compounds of formula (I) are also within the scope of the present invention. The term 'metabolites' refers to all molecules derived from any of the compounds according to the present invention in a cell or organism, preferably mammal. Preferably the term relates to molecules which differ from any molecule which is present in any such cell or organism under physiological conditions.

A treatment defined herein may be applied as a sole therapy of may involve, in addition to the compounds of the invention, conventional surgery or radiotherapy or chemotherapy. Furthermore, compounds of formula (I) can also be used in combination with existing therapeutic agents for the treatment of conditions associated with cancer, including small molecule therapeutics or antibody based therapeutics.

The compounds described herein are characterised by a cyanopyrrolidine core with a methylamine group attached to the cyanopyrrolidine ring, wherein the methylamine group is substituted with a monocyclic heteroaryl or aryl ring, wherein the monocyclic heteroaryl or aryl ring is substituted, or an optionally substituted bicyclic heteroaryl or aryl ring, optionally via a linker.

In accordance with a first aspect of the invention there is provided a compound of formula

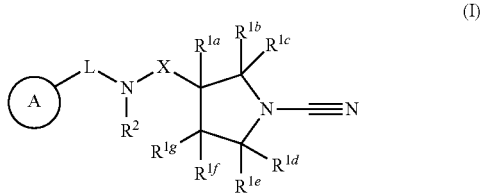

(I)

or a pharmaceutically acceptable salt thereof, wherein:
$R^{1b}$, $R^{1c}$, $R^{1d}$, $R^{1e}$ each independently represent hydrogen or an optionally substituted $C_1$-$C_6$ alkyl, or $R^{1b}$ is linked to $R^{1a}$ or $R^{1c}$ to form an optionally substituted 3 to 6 membered cycloalkyl ring, or $R^{1e}$ is linked to $R^{1d}$ or $R^{1f}$ to form an optionally substituted 3 to 6 membered cycloalkyl ring;
$R^{1a}$ and $R^{1g}$ each independently represent hydrogen, fluorine, cyano, hydroxyl, amino, optionally substituted $C_1$-$C_6$ alkyl or optionally substituted $C_1$-$C_6$ alkoxy, or $R^{1a}$ and $R^{1g}$ together form an optionally substituted $C_3$-$C_6$ cycloalkyl ring, or $R^{1a}$ is linked to $R^{1b}$ to form an optionally substituted $C_3$-$C_6$ cycloalkyl ring, or $R^{1g}$ is linked to $R^{1f}$ to form an optionally substituted $C_3$-$C_6$ cycloalkyl ring;
$R^{1f}$ represents hydrogen, fluorine, cyano, hydroxyl, amino, optionally substituted $C_1$-$C_6$ alkyl, optionally substituted $C_1$-$C_6$ alkoxy, or $R^{1f}$ is linked to $R^{1g}$ or $R^{1e}$ to form an optionally substituted 3 to 6 membered cycloalkyl ring, or $R^{1f}$ together with $R^2$ forms an optionally further substituted heterocyclic ring;
$R^2$ represents hydrogen, optionally substituted $C_1$-$C_6$ alkyl or $R^2$ together with $R^{1f}$ forms an optionally further substituted heterocyclic ring;
X is $C(R^3)(R^4)$, wherein $R^3$ and $R^4$ each independently represent hydrogen, cyano, optionally substituted $C_1$-$C_6$ alkyl, a 5 or 6 membered heteroaryl or aryl ring or $R^3$ and $R^4$ together form a 3 to 6 membered heteroalkyl or cycloalkyl ring;
L represents a covalent bond, —SO—, —$SO_2$—, —C(O)—, —C(O)O—, —$CONR^5$—, —$SO_2NR^5$—, —C(O)—$C_1$-$C_6$ alkylene, —C(O)—$C_2$-$C_6$ alkenylene, $C_1$-$C_6$ alkylene-C(O)—, $C_2$-$C_6$ alkenylene-C(O)—, —$C_1$-$C_6$ alkylene-$NR^5CO$—, —$C_1$-$C_6$ alkylene-$CONR^5$—, optionally substituted $C_1$-$C_6$ alkylene or optionally substituted —$C_2$-$C_6$ alkenylene;
A represents a substituted monocyclic heteroaryl or aryl ring or an optionally substituted bicyclic heteroaryl or aryl ring;
$R^5$ represents hydrogen or optionally substituted $C_1$-$C_6$ alkyl.

$R^{1a}$ represents hydrogen, fluorine, cyano, hydroxyl, amino, optionally substituted $C_1$-$C_6$ alkyl or optionally substituted $C_1$-$C_6$ alkoxy. $R^{1a}$ may represent hydrogen. $R^{1a}$ may represent fluorine. $R^{1a}$ may represent methyl. When $R^{1a}$ represents fluorine, cyano, hydroxyl, amino, optionally substituted $C_1$-$C_6$ alkyl or optionally substituted $C_1$-$C_6$ alkoxy, $R^{1b}$, $R^{1c}$, $R^{1d}$, $R^{1e}$, $R^{1f}$ and $R^{1g}$ may each represent hydrogen. The alkyl or alkoxy may be unsubstituted or substituted with one or more substituents selected from halogen, hydroxyl, thiol, cyano, amino, nitro and $SF_5$, in particular fluorine. Alternatively, $R^{1a}$ may be linked to $R^{1b}$ or $R^{1g}$ to form an optionally substituted cycloalkyl ring. The cycloalkyl ring can contain 3, 4, 5 or 6 atoms, in particular 3 or 4 atoms. The $C_3$-$C_6$ cycoalkyl ring may be substituted or unsubstituted.

$R^{1b}$, $R^{1c}$, $R^{1d}$, $R^{1e}$ may each independently represent hydrogen or optionally substituted $C_1$-$C_6$ alkyl. In particular, $R^{1b}$, $R^{1c}$, $R^{1d}$, $R^{1e}$ may each independently represent hydrogen or $C_1$-$C_3$ alkyl (e.g. methyl or ethyl). $R^{1b}$ may be hydrogen or $C_1$-$C_3$ alkyl and $R^{1c}$ may be hydrogen. $R^{1d}$ may be hydrogen or $C_1$-$C_3$ alkyl and $R^{1e}$ may be hydrogen. The alkyl may be unsubstituted or substituted with one or more substituents selected from halogen, hydroxyl, thiol, cyano, amino, nitro and $SF_5$. In particular $R^{1b}$, $R^{1c}$, $R^{1d}$, $R^{1e}$ each represent hydrogen.

$R^{1b}$ may represent hydrogen. $R^{1b}$ may represent $C_1$-$C_6$ alkyl. $R^{1b}$ may represent $C_1$-$C_3$ alkyl, for example, methyl or ethyl. When $R^{1b}$ represents $C_1$-$C_6$ alkyl, $R^{1a}$, $R^{1c}$, $R^{1d}$, $R^{1e}$, $R^{1f}$ and $R^{1g}$ may each represent hydrogen. The alkyl may be unsubstituted or substituted with one or more substituents selected from halogen, hydroxyl, thiol, cyano, amino, nitro and $SF_5$, in particular fluorine.

$R^{1c}$ may represent hydrogen. $R^{1c}$ may represent $C_1$-$C_6$ alkyl. $R^{1c}$ may represent $C_1$-$C_3$ alkyl, for example, methyl or ethyl. When $R^{1c}$ represents $C_1$-$C_6$ alkyl, $R^{1a}$, $R^{1b}$, $R^{1d}$, $R^{1e}$, $R^{1f}$ and $R^{1g}$ may each represent hydrogen. The alkyl may be unsubstituted or substituted with one or more substituents selected from halogen, hydroxyl, thiol, cyano, amino, nitro and $SF_5$, in particular fluorine.

$R^{1d}$ may represent hydrogen. $R^{1d}$ may represent $C_1$-$C_6$ alkyl. $R^{1d}$ may represent $C_1$-$C_3$ alkyl, for example, methyl or ethyl. When $R^{1d}$ represents $C_1$-$C_6$ alkyl, $R^{1a}$, $R^{1b}$, $R^{1c}$, $R^{1e}$, $R^{1f}$ and $R^{1g}$ may each represent hydrogen. The alkyl may be unsubstituted or substituted with one or more substituents selected from halogen, hydroxyl, thiol, cyano, amino, nitro and SF$_5$, in particular fluorine.

R$^{1e}$ may represent hydrogen. R$^{1e}$ may represent C$_1$-C$_6$ alkyl. R$^{1e}$ may represent C$_1$-C$_3$ alkyl, for example, methyl or ethyl. When R$^{1e}$ represents C$_1$-C$_6$ alkyl, R$^{1a}$, R$^{1b}$, R$^{1c}$, R$^{1d}$, R$^{1f}$ and R$^{1g}$ may each represent hydrogen. The alkyl may be unsubstituted or substituted with one or more substituents selected from halogen, hydroxyl, thiol, cyano, amino, nitro and SF$_5$, in particular fluorine.

Alternatively, R$^{1b}$ may be linked to R$^{1c}$ to form a cycloalkyl ring. In addition, or alternatively, R$^{1d}$ may be linked to R$^{1e}$ to form a cycloalkyl ring. The cycloalkyl ring can contain 3, 4, 5 or 6 atoms, in particular 3 or 4 atoms. When R$^{1b}$ and R$^{1c}$ together form a C$_3$-C$_6$ cycloalkyl ring, R$^{1a}$, R$^{1d}$, R$^{1e}$, R$^{1f}$ and R$^{1g}$ may be hydrogen. When R$^{1d}$ and R$^{1e}$ together form a cycloalkyl ring, R$^{1a}$, R$^{1b}$, R$^{1c}$, R$^{1f}$ and R$^{1g}$ may be hydrogen. The cycloalkyl ring may be substituted or unsubstituted.

R$^{1f}$ may represent hydrogen, fluorine, cyano, hydroxyl, amino, optionally substituted C$_1$-C$_6$ alkyl or optionally substituted C$_1$-C$_6$ alkoxy. The alkyl and alkoxy may be substituted with one or more substituents selected from halogen, hydroxyl, thiol, cyano, amino, nitro and SF$_5$. In particular, R$^{1f}$ can represent hydrogen, fluorine, C$_1$-C$_3$ alkyl or substituted C$_1$-C$_3$ alkoxy. R$^{1f}$ can represent fluorine. R$^{1f}$ can represent methyl. R$^{1f}$ can represent methoxy. R$^{1f}$ can represent CF$_3$. R$^{1f}$ can represent OCF$_3$. In particular examples, R$^{1f}$ represents hydrogen.

R$^{1g}$ represents hydrogen, fluorine, cyano, hydroxyl, amino, optionally substituted C$_1$-C$_6$ alkyl or optionally substituted C$_1$-C$_6$ alkoxy. R$^{1g}$ may represent hydrogen. R$^{1g}$ may represent fluorine. R$^{1g}$ may represent methyl. When R$^{1g}$ represents fluorine, cyano, hydroxyl, amino, optionally substituted C$_1$-C$_6$ alkyl or optionally substituted C$_1$-C$_6$ alkoxy, R$^{1a}$, R$^{1b}$, R$^{1c}$, R$^{1d}$, R$^{1e}$ and R$^{1f}$ may each represent hydrogen. The alkyl or alkoxy may be unsubstituted or substituted with one or more substituents selected from halogen, hydroxyl, thiol, cyano, amino, nitro and SF$_5$, in particular fluorine. Alternatively, R$^{1g}$ is linked to R$^{1a}$ or R$^{1f}$ to form an optionally substituted cycloalkyl ring. The cycloalkyl ring can contain 3, 4, 5 or 6 atoms, in particular 3 or 4 atoms. When R$^{1g}$ forms a C$_3$-C$_6$ cycloalkyl ring, R$^{1b}$, R$^{1c}$, R$^{1d}$, R$^{1e}$ and R$^{1a}$/R$^{1f}$ may each represent hydrogen. The cycloalkyl ring may be unsubstituted or substituted.

One of R$^{1a}$, R$^{1b}$, R$^{1c}$, R$^{1d}$, R$^{1e}$, R$^{1f}$ and R$^{1g}$ may be other than hydrogen, and the remaining are each hydrogen.

Two of R$^{1a}$, R$^{1b}$, R$^{1c}$, R$^{1d}$, R$^{1e}$, R$^{1f}$ and R$^{1g}$ may be other than hydrogen, and the remaining are each hydrogen.

Three of R$^{1a}$, R$^{1b}$, R$^{1c}$, R$^{1d}$, R$^{1e}$, R$^{1f}$ and R$^{1g}$ may be other than hydrogen, and the remaining are each hydrogen.

Four of R$^{1a}$, R$^{1b}$, R$^{1c}$, R$^{1d}$, R$^{1e}$, R$^{1f}$ and R$^{1g}$ may be other than hydrogen, and the remaining are each hydrogen.

Five of R$^{1a}$, R$^{1b}$, R$^{1c}$, R$^{1d}$, R$^{1e}$, R$^{1f}$ and R$^{1g}$ may be other than hydrogen, and the remaining are each hydrogen.

Six of R$^{1a}$, R$^{1b}$, R$^{1c}$, R$^{1d}$, R$^{1e}$, R$^{1f}$ and R$^{1g}$ may be other than hydrogen, and the remaining are each hydrogen.

When one, two, three, four, five or six of R$^{1a}$, R$^{1b}$, R$^{1c}$, R$^{1d}$, R$^{1e}$, R$^{1f}$ and R$^{1g}$ are other than hydrogen, the remaining R groups represent a group in accordance with the definitions above. In particular, one, two, three or four of R$^{1a}$, R$^{1b}$, R$^{1c}$, R$^{1d}$, R$^{1e}$, R$^{1f}$ and R$^{1g}$ may be other than hydrogen and the remaining each represent hydrogen. More particularly, one or two of R$^{1a}$, R$^{1b}$, R$^{1c}$, R$^{1d}$, R$^{1e}$, R$^{1f}$ and R$^{1g}$ may be other than hydrogen and the remaining each represent hydrogen.

The compounds may be in the form where R$^{1a}$, R$^{1b}$, R$^{1c}$, R$^{1d}$, R$^{1e}$, R$^{1f}$ and R$^{1g}$ are all hydrogen. In such cases the compounds may be of formula (IA):

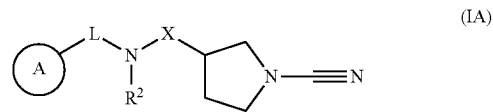

or a pharmaceutically acceptable salt thereof, wherein:
R$^2$ represents hydrogen or optionally substituted C$_1$-C$_6$ alkyl;
X is C(R$^3$)(R$^4$), wherein R$^3$ and R$^4$ each independently represent hydrogen, cyano, optionally substituted C$_1$-C$_6$ alkyl, a 5 or 6 membered heteroaryl or aryl ring or R$^3$ and R$^4$ together form a 3 to 6 membered heterocyclyl or cycloalkyl ring;
L represents a covalent bond, —SO—, —SO$_2$—, —C(O)—, —C(O)O—, —CONR$^5$—, —SO$_2$NR$^5$—, —C(O)—C$_1$-C$_6$ alkylene, —C(O)—C$_2$-C$_6$ alkenylene, —C$_1$-C$_6$ alkylene-C(O)—, —C$_2$-C$_6$ alkenylene-C(O)—, —C$_1$-C$_6$ alkylene-NR$^5$CO—, —C$_1$-C$_6$ alkylene-CONR$^5$—, optionally substituted C$_1$-C$_6$ alkylene or optionally substituted —C$_2$-C$_6$ alkenylene;
A represents a substituted monocyclic heteroaryl or aryl ring or an optionally substituted bicyclic heteroaryl or aryl ring;
R$^5$ represents hydrogen or optionally substituted C$_1$-C$_6$ alkyl.

R$^2$ represents hydrogen, C$_1$-C$_6$ alkyl or R$^2$ together with R$^{1f}$ forms an optionally further substituted heterocyclic ring, wherein the alkyl may be substituted with one or more substituents selected from halogen, hydroxyl, thiol, cyano, amino, nitro and SF$_5$. In particular, R$^2$ represents hydrogen, C$_1$-C$_3$ alkyl, or together with R$^{1f}$ forms an optionally further substituted (i.e. in addition to substitution with -L-A) 5 or 6 membered heterocyclic ring. R$^2$ may represent hydrogen. R$^2$ may represent methyl or ethyl, in particular, methyl. R$^2$ cannot link to R$^3$, R$^4$, L or ring A.

In particular examples, R$^{1f}$ represents hydrogen and R$^2$ represents hydrogen or C$_1$-C$_3$ alkyl, preferably methyl, or R$^{1f}$ and R$^2$ together form a 5 to 7 membered heterocyclic ring (which includes in the ring the amine nitrogen and X), wherein the ring is optionally further substituted with one or more fluorine, oxo, cyano, hydroxyl, amino, C$_1$-C$_6$ alkyl or C$_1$-C$_6$ alkoxy, wherein the alkyl or alkoxy may be substituted with one or more substituents selected from halogen, hydroxyl, thiol, cyano, amino, nitro and SF$_5$. When R$^{1f}$ and R$^2$ together form an optionally further substituted 5 to 7 membered heterocyclyl ring, this ring is fused to the pyrrolidine ring to form an 8 to 10 membered bicyclic ring. In particular, R$^{1f}$ and R$^2$ may together form a 5 membered heterocyclic ring which is not further substituted. Alternatively, R$^{1f}$ and R$^2$ together form a 5 membered heterocylic ring which is further substituted with one or more halogen, oxo, amino, amide, C$_1$-C$_6$ alkyl or C$_1$-C$_6$ alkoxy. In particular, the 5 membered heterocyclyl ring is further substituted with oxo. Any further substitution is in addition to the substitution with ring A, via L.

In certain instances, R$^{1a}$, R$^{1b}$, R$^{1c}$, R$^{1d}$, R$^{1e}$ and R$^{1f}$ may each be hydrogen and R$^{1f}$ may be hydrogen or together with R$^2$ may form an optionally further substituted 5 membered heterocyclyl ring.

X represents C(R$^3$)(R$^4$), wherein R$^3$ and R$^4$ each independently represent hydrogen, cyano, C$_1$-C$_6$ alkyl, an optionally substituted 5 or 6 membered heteroaryl or aryl ring or $R^3$ and $R^4$ together with the carbon to which they are attached form an optionally substituted 3 to 6 membered heterocyclyl or cycloalkyl ring, wherein the alkyl may be unsubstituted or substituted with one or more substituents selected from halogen, hydroxyl, thiol, cyano, amino, nitro and $SF_5$. The 3 to 6 membered heterocyclyl or cycloalkyl ring may be cyclopropyl or cyclobutyl. In particular, $R^3$ may represent hydrogen and $R^4$ may represent hydrogen, cyano, $C_1$-$C_6$ alkyl, an optionally substituted 5 or 6 membered heteroaryl or aryl ring or $R^3$ and $R^4$ together with the carbon to which they are attached form an optionally substituted 3 to 6 membered heterocyclyl or cycloalkyl ring, wherein the alkyl may be unsubstituted or substituted with one or more substituents selected from halogen, hydroxyl, thiol, cyano, amino, nitro and $SF_5$. $R^3$ and $R^4$ may each independently represent hydrogen, cyano, or $C_1$-$C_3$ alkyl. In particular examples, $R^3$ and $R^4$ each independently represent hydrogen, cyano or methyl, e.g. $R^3$ is hydrogen and $R^4$ is hydrogen, cyano or methyl. More particularly, X represents $CH_2$, CHCN or CHMe.

L represents a covalent bond, —SO—, —$SO_2$—, —C(O)—, —C(O)O—, —$CONR^5$—, —$SO_2NR^5$—, —C(O)—$C_1$-$C_6$ alkylene, —C(O)—$C_2$-$C_6$ alkenylene, $C_1$-$C_6$ alkylene-C(O)—, $C_2$-$C_6$ alkenylene-C(O)—, —$C_1$-$C_6$ alkylene-$NR^5CO$—, —$C_1$-$C_6$ alkylene-$CONR^5$—, optionally substituted $C_1$-$C_6$ alkylene or optionally substituted —$C_2$-$C_6$ alkenylene. The alkylene and alkenylene are optionally substituted with halogen, hydroxyl, thiol, cyano, amino, nitro and $SF_5$. $R^5$ represents hydrogen or $C_1$-$C_6$ alkyl, wherein the alkyl is optionally substituted with halogen, hydroxyl, thiol, cyano, amino, nitro and $SF_5$.

In particular examples, L represents a covalent bond, —$SO_2$—, —C(O)—, —C(O)—$C_1$-$C_6$ alkylene preferably —C(O)—$C_1$-$C_3$ alkylene, —C(O)—$C_2$-$C_6$ alkenylene preferably —C(O)—$C_2$-$C_4$ alkenylene, or —$CONR^5$— wherein $R^5$ represents hydrogen or methyl, preferably hydrogen.

In formula (I) defined herein, ring A represents a 5 to 10 membered (e.g. 5, 6, 7, 8, 9 or 10 membered) ring, wherein the ring is either a substituted monocyclic heteroaryl or aryl ring or an optionally substituted bicyclic heteroaryl or aryl ring. The heteroaryl or aryl ring may be attached directly to the amine nitrogen atom to form an N-aryl bond or may be attached via a linker, i.e. when L is not a covalent bond.

When the ring is bicyclic, the second ring (i.e. the ring not attached to the amine nitrogen, either directly or via a linker) may be aromatic or partly unsaturated and thus whilst not every atom in the 5 to 10 heteroaryl or aryl ring need be in an aryl system, there must be at least one aryl or heteroaryl ring within the 5 to 10 atoms, and it is this aryl or heteroaryl ring which is attached to the amine nitrogen, either directly or via a linker.

Ring A may represent a 5 to 10 membered heteroary or aryl ring and when substituted, may be substituted with one or more (e.g. one, two, three or four) of -$Q^1$-($R^6$)$_n$, in particular one or two of $Q^1$-($R^6$)$_n$.

In particular, ring A may represent a 5 or 6 membered heteroaryl or aryl ring which is substituted with one or more (e.g. one, two, three or four) of -Q-($R^6$)$_n$.

Alternatively, ring A may represent a 9 or 10 membered bicyclic heteroaryl or aryl ring which may be optionally substituted with one or more (e.g. one, two, three or four) of -$Q^1$-($R^6$)$_n$.

When ring A is a heteroaryl ring, the ring may comprise one or more (e.g. 1, 2 or 3) heteroatoms independently selected from nitrogen, oxygen and sulphur. In particular, the heteroaryl ring contains at least one nitrogen atom, for example, 1, 2 or 3 nitrogen atoms, preferably 1 or 2 nitrogen heteroatoms.

Ring A may be selected from the group consisting of pyridinyl, pyrazinyl, pyrimidinyl, pyridazinyl, furyl, pyrrolyl, oxazolyl, thiazolyl, pyrazolyl, triazolyl, tetrazolyl, indolyl, indolizinyl, isoindolyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, triazinyl, dihydrophyridinyl, dihydropyrrolopyridinyl, benzoxazolyl, quinoxalinyl, benzomorpholinyl, tetrahydropyridopyrazinyl, tetrahydroqinolinyl, tetrahydroisoquinolinyl, isoindolinyl, phenyl, naphthyl and naphthalenyl.

In particular, ring A is selected from the group consisting of pyridinyl, pyrazinyl, pyrimidinyl, pyridazinyl, furyl, pyrrolyl, oxazolyl, thiazolyl, pyrazolyl, triazolyl, tetrazolyl, indolyl, indolizinyl, isoindolyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, triazinyl, dihydrophyridinyl, quinoxalinyl, benzomorpholinyl, phenyl, naphthyl and naphthalenyl.

More particularly, ring A is selected from the group consisting of oxazolyl, isoxazolyl, pyrazolyl, thiazolyl, pyridinyl, quinolinyl, benzothiazolyl, isoquinolinyl, pyrimidinyl, phenyl, benzomorpholinyl, indazolyl, imidazopyridinyl, quinazolinyl, pyrazolopyridinyl, benzimidazolyl, imidazolyl and oxadiazolyl.

For example, ring A is selected from the group consisting of oxazolyl, isoxazolyl, pyrazolyl, thiazolyl, pyridinyl, quinolinyl, benzothiazolyl, isoquinolinyl, pyrimidinyl, phenyl, benzomorpholinyl, indazolyl, imidazopyridinyl, and isoindolinyl.

When ring A is monocyclic the ring is substituted. When ring A is bicyclic the ring may be either unsubstituted or substituted. When substituted, ring A may be substituted with one or more -$Q^1$-($R^6$)$_n$, in particular one or two -$Q^1$-($R^6$)$_n$, wherein each occurrence -$Q^1$-($R^6$)$_n$ is the same or different, and wherein:
n is 0 or 1;
$Q^1$ represents halogen, cyano, oxo, nitro, —$OR^7$, —$SR^7$, —$NR^7R^8$, —$CONR^7R^8$, —$NR^7COR^8$, —$NR^7CONR^8R^9$, —$COR^7$, —$C(O)OR^7$, —$SO_2R^7$, —$SO_2NR^7R^8$, —$NR^7SO_2R^8$, $NR^7SO_2NR^8R^9$, —$NR^7C(O)OR^8$, optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, a covalent bond, an oxygen atom, a sulphur atom, —SO—, —$SO_2$—, —C(O)—, —C(O)O—, —$CONR^7$—, —$NR^7$—, —$NR^7CO$—, —$NR^7CONR^8$—, —$SO_2NR^7$—, —$NR^7SO_2$—, —$NR^7SO_2NR^8$—, —$NR^7C(O)O$—, —$NR^7C(O)OR^8$—, optionally substituted $C_1$-$C_6$ alkylene or optionally substituted —$C_2$-$C_6$ alkenylene;
$R^7$, $R^8$ and $R^9$ each independently represent hydrogen, optionally substituted $C_1$-$C_6$ alkyl or optionally substituted $C_1$-$C_6$ alkylene.

When n is 1, $R^6$ represents an optionally substituted 3 to 10 membered heterocyclyl, cycloalkyl, heteroaryl or aryl ring (when n is 0, $Q^1$ is present and $R^6$ is absent).

Ring A may be unsubstituted (if a bicyclic ring) or substituted with one, two, three or four of -$Q^1$-($R^6$)$_n$. In particular, ring A is either unsubstituted (if a bicyclic ring) or substituted with one or two of -$Q^1$-($R^6$)$_n$. Each occurrence of -$Q^1$-($R^6$)$_n$ may be the same or different. More particularly, ring A is either unsubstituted (if bicyclic) or substituted with one of $Q^1$-($R^6$)$_n$. $Q^1$, $R^6$ and n are as defined herein.

In particular, $Q^1$ may be selected from halogen (e.g. fluorine, chlorine or bromine), cyano, oxo, nitro, —$OR^7$ (e.g hydroxyl), —$SR^7$ (e.g. thiol), —$NR^7R^8$ (e.g. amino or N,N-dimethylamino), —$CONR^7R^8$ (e.g. amido), —$NR^7COR^8$ (N-acetyl), —$NR^7CONR^8R^9$, —$COR^7$ (e.g. acetyl), —C(O)$OR^7$ (e.g. methoxycarbonyl or ethoxycarbonyl), —$SO_2R^7$ (e.g. methyl sulphonyl), —$SO_2NR^7R^8$ (e.g. dimethylaminosulphonyl), —$NR^7SO_2R^8$, $NR^7SO_2NR^8R^9$, —$NR^7C(O)OR^8$, optionally substituted —$C_1$-$C_4$ alkyl (e.g. propyl, isobutyl or tert butyl), optionally substituted $C_1$-$C_2$ alkyl (e.g. methyl or ethyl), optionally substituted —$C_1$-$C_6$ alkoxy, optionally substituted —$C_2$-$C_6$ alkenyl, optionally substituted —$C_2$-$C_6$ alkynyl, a covalent bond, an oxygen atom, a sulphur atom, —SO—, —$SO_2$—, —CO—, —C(O)O—, —$CONR^7$—, —$NR^7$— (e.g. methylamino), —$NR^7CO$—, —$NR^7CONR^8$—, —$SO_2NR^7$—, —$NR^7SO_2$—, —$NR^7SO_2NR^8$—, —$NR^7C(O)O$—, —$NR^7C(O)OR^8$—, optionally substituted $C_1$-$C_4$ alkylene (e.g. methylene or ethylene) or optionally substituted —$C_2$-$C_4$ alkenylene (e,g. vinyl).

When n is 0, ring A may be substituted with one or more (e.g. one, two, three or four) $Q^1$ substituents independently selected from halogen (e.g. fluorine, chlorine or bromine), cyano, oxo, nitro, —$OR^7$, —$SR^7$, —$NR^7R^8$, —$CONR^7R^8$, —$NR^7C(O)R^8$, —$NR^7C(O)NR^8R^9$, —$C(O)R^7$, —C(O)$OR^7$, —$SO_2R^7$, —$SO_2NR^7R^8$, —$NR^7SO_2R^8$, $NR^7SO_2NR^8R^9$, —$NR^7C(O)OR^8$, —$C_1$-$C_6$ alkyl, —$C_1$-$C_6$ alkoxy, —$C_2$-$C_6$ alkenyl, or —$C_2$-$C_6$ alkynyl, wherein alkyl, alkoxy, alkenyl or alkynyl, may be unsubstituted or substituted with one or more substituents selected from halogen, hydroxyl, thiol, cyano, amino, nitro and $SF_5$, and wherein $R^7$, $R^8$ and $R^9$ are as defined above.

In particular, when n is 0, $Q^1$ may represent halogen (e.g. fluorine or chlorine), cyano, oxo, —C(O)$NR^7R^8$, —$NR^7COR^8$, $C_1$-$C_6$ alkyl or $C_1$-$C_6$ alkoxy, wherein the alkyl and alkoxy may be unsubstituted or substituted with one or more halogen, in particular fluorine.

In particular examples, n is 0 and ring A represents a 5 or 6 membered heteroaryl or aryl ring which is substituted with one or more (e.g. one, two, three or four) $Q^1$ substituents independently selected from halogen, oxo, —$NR^7COR^8$, $C_1$-$C_3$ alkyl (e.g. methyl) or $C_1$-$C_3$ alkoxy (e.g. methoxy), wherein the alkyl or alkoxy is optionally substituted with one or more fluorine.

In further examples, n is 0 and ring A represents a 9 or 10 membered heteroaryl or aryl ring which is optionally substituted with one or more (e.g. one, two, three or four) $Q^1$ substituents independently selected from halogen, oxo, cyano, $C_1$-$C_3$ alkyl or —C(O)$NR^7R^8$, wherein the alkyl is optionally substituted with one or more fluorine.

When n is 1, $Q^1$ is a covalent bond or a linker selected from an oxygen atom, a sulphur atom, —SO—, —$SO_2$—, —CO—, —C(O)O—, —$CONR^7$—, —$NR^7$—, —$NR^7CO$—, —$NR^7CONR^8$—, —$SO_2NR^7$—, —$NR^7SO_2$—, —$NR^7SO_2NR^8$—, —$NR^7C(O)O$—, —$NR^7C(O)OR^8$—, $C_1$-$C_6$ alkylene or —$C_2$-$C_6$ alkenylene, wherein the alkylene or alkenylene is optionally substituted with one or more substituents selected from halogen, hydroxyl, thiol, cyano, amino, nitro and $SF_5$.

In particular, when n is 1, $Q^1$ is selected from a covalent bond, $C_1$-$C_6$ alkylene in particular $C_1$-$C_3$ alkylene, preferably methylene, or an oxygen atom.

In particular examples, ring A is substituted with a further ring either directly or via a linker, i.e., ring A is substituted with at least one -$Q^1$-($R^6$)$_n$ wherein n is 1.

$R^6$ represents a 3 to 10 membered heterocyclyl, cycloalkyl, heteroaryl or aryl ring. $R^6$ may be selected from cyclopropyl, cyclobutyl, cyclopentyl, cyclohexyl, cycloheptyl, cyclooctyl, decahydronaphthalenyl, phenyl, naphthyl, naphthalenyl, pyridinyl, pyrazinyl, pyrimidinyl, pyridazinyl, furyl, pyrrolyl, oxazolyl, thiazolyl, pyrazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, triazinyl, dihydrophyridinyl, dihydropyrrolopyridinyl, benzoxazole, quinoxalinyl, benzomorpholinyl, tetrahydropyridopyrazinyl, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl, and tetrahydroisoquinolinyl.

$R^6$ may be selected from cyclopropyl, cyclobutyl, cyclopentyl, cyclohexyl, cycloheptyl, cyclooctyl, decahydronaphthalenyl, phenyl, naphthyl, naphthalenyl, pyridinyl, pyrazinyl, pyrimidinyl, pyridazinyl, furyl, pyrrolyl, oxazolyl, thiazolyl, pyrazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, dihydrophyridinyl, quinoxalinyl, benzomorpholinyl, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl, and tetrahydroisoquinolinyl.

$R^6$ may represent an optionally substituted 5 or 6 membered heterocyclyl, cycloalkyl, heteroaryl or aryl ring.

Alternatively, $R^6$ may represent an optionally substituted 9 or 10 membered bicyclic heterocyclyl, cycloalkyl, heteroaryl or aryl ring.

In particular, $R^6$ is selected from substituted or unsubstituted phenyl, thiazolyl, pyridinyl, pyrrolidinyl pyrazolyl, isoindolyl, isoxazolyl and cycloalkyl, e.g. cyclopropyl or cyclobutyl.

More particularly, $R^6$ is selected from substituted or unsubstituted phenyl, thiazolyl, pyridinyl, pyrrolidinyl pyrazolyl, isoindolyl, isoxazolyl and cyclopropyl.

For example, $R^6$ is selected from substituted or unsubstituted phenyl, thiazolyl, pyridinyl, pyrrolidinyl, pyrazolyl and isoindolyl.

More particularly, $R^6$ is substituted or unsubstituted phenyl.

In all cases described herein, $R^6$ may be optionally substituted with one or more substituents independently selected from halogen, cyano, oxo, nitro, —$OR^{10}$, —$SR^{10}$, —$NR^{10}R^{11}$, —$CONR^{10}R^{11}$, —$NR^{10}COR^{11}$, —$NR^{10}CONR^{11}R^{12}$, —$COR^{10}$, —$C(O)OR^{10}$, —$SO_2R^{10}$, —$SO_2NR^{10}R^{11}$, —$NR^{10}SO_2R^{11}$, $NR^{10}SO_2NR^{11}R^{12}$, —$NR^{10}C(O)OR^{11}$, optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, -$Q^2$-$R^{10}$, -$Q^2$-$NR^{10}CONR^{11}R^{12}$, -$Q^2$-$NR^{10}R^{11}$, -$Q^2$-$COR^{10}$, -$Q^2$-$NR^{10}COR^{11}$, -$Q^2$-$NR^{10}C(O)OR^{11}$, -$Q^2$-$SO_2R^{10}$, $Q^2$-$CONR^{10}R^{11}$, -$Q^2$-$CO_2R^{10}$, -$Q^2$-$SO_2NR^{10}R^{11}$, -$Q^2$-$NR^{10}SO_2R^{11}$, and -$Q^2$-$NR^{10}SO_2NR^{11}R^{12}$, wherein the alkyl, alkoxy, alkenyl or alkynyl are optionally substituted with one or more substituents selected from halogen, hydroxyl, thiol, cyano, amino, nitro and $SF_5$.

$Q^2$ represents a covalent bond, an oxygen atom, a sulphur atom, —SO—, —$SO_2$—, —CO—, $C_1$-$C_6$ alkylene or optionally substituted $C_2$-$C_6$ alkenylene.

$R^{10}$, $R^{11}$, $R^{12}$ each independently represent hydrogen, optionally substituted $C_1$-$C_6$ alkyl, optionally substituted heterocyclyl, optionally substituted heteroaryl, optionally substituted aryl, or an optionally substituted cycloalkyl.

$R^6$ may be substituted with one or more (e.g. one, two, three or four), in particular one or two, substituents independently selected from halogen, cyano, oxo, nitro, —$OR^{10}$, —$SR^{10}$, —$NR^{10}R^{11}$, —$CONR^{10}R^{11}$, —$NR^{10}COR^{11}$, —$NR^{10}CONR^{11}R^{12}$, —$COR^{10}$, —$C(O)OR^{10}$, —$SO_2R^{10}$, —$SO_2NR^{10}R^{11}$, —$NR^{10}SO_2R^{11}$, $NR^{10}SO_2NR^{11}R^{12}$, —$NR^{10}C(O)OR^{11}$, optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, -$Q^2$-$R^{10}$, -$Q^2NR^{10}CONR^{11}R^{12}$, -$Q^2$-$NR^{10}R^{11}$, -$Q^2$-$COR^{10}$, -$Q^2$-$NR^{10}COR^{11}$, -$Q^2$-$NR^{10}C(O)OR^{11}$, -$Q^2$-$SO_2R^{10}$, $Q^2$-$CONR^{10}R^{11}$, -$Q^2$-$CO_2R^{10}$, -$Q^2$-$SO_2NR^{10}R^{11}$, -$Q^2$-$NR^{10}SO_2R^{11}$ and -$Q^2$-$NR^{10}SO_2NR^{11}R^{12}$, wherein $Q^2$ represents a covalent bond, an oxygen atom, a sulphur atom, —SO—, —$SO_2$—, —CO—, $C_1$-$C_6$ alkylene or optionally substituted $C_2$-$C_6$ alkenylene, and wherein $R^{10}$, $R^{11}$, $R^{12}$ each independently represent hydrogen or optionally substituted $C_1$-$C_6$ alkyl, wherein any alkyl, alkoxy, alkenyl, alkynyl, alkylene or alkenylene is optionally substituted with one or more (e.g. one, two, three or four) substituents selected from halogen, hydroxyl, thiol, cyano, amino, nitro and $SF_5$.

In particular, $R^6$ may be substituted with one or more substituents selected from halogen (for example, fluorine or chlorine), cyano, $C_1$-$C_4$ alkyl (e.g. propyl, isobutyl or tert butyl) or $C_1$-$C_2$ alkyl (e.g. methyl or ethyl), $C_1$-$C_4$ alkoxy or $C_1$-$C_2$ alkoxy (e.g. methoxy) wherein the alkyl and alkoxy may be optionally substituted with one or more fluorine.

For example, $R^6$ may be substituted with one or more substituents selected from halogen (for example, fluorine or chlorine), $C_1$-$C_4$ alkyl (e.g. propyl, isobutyl or tert butyl) or $C_1$-$C_2$ alkyl (e.g. methyl or ethyl) wherein the alkyl may be optionally substituted with one or more fluorine.

Alternatively, $R^6$ may be optionally substituted with a further optionally substituted 3 to 10 membered heterocyclyl, cycloalkyl, heteroaryl or aryl ring, either directly attached or via a linking group. The linking group may be an oxygen atom, a carbonyl or an optionally substituted $C_1$-$C_6$ alkylene. The linking group may be oxygen, —CO— or an alkylene chain, for example, methylene. The 3 to 10 membered ring may be substituted with one or more (e.g. one, two, three of four), in particular one or two, substituents selected from halogen (for example, fluorine or chlorine), $C_1$-$C_4$ alkyl (e.g. propyl, isobutyl or tert butyl) or $C_1$-$C_2$ alkyl (e.g. methyl or ethyl) wherein the alkyl may be optionally substituted with one or more fluorine.

$R^6$ may be unsubstituted, mono-substituted or di-substituted.

In certain instances, $R^6$ represents a 3 to 10 membered heterocyclyl, cycloalkyl, heteroaryl or aryl ring selected from cyclopropyl, cyclobutyl, cyclopentyl, cyclohexyl, cycloheptyl, cyclooctyl, decahydronaphthalenyl, phenyl, naphthyl, naphthalenyl, pyridinyl, pyrazinyl, pyrimidinyl, pyridazinyl, furyl, pyrrolyl, oxazolyl, thiazolyl, pyrazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, dihydrophyridinyl, dihydropyrrolopyridinyl, benzoxazolyl, quinoxalinyl, benzomorpholinyl, tetrahydropyridopyrazinyl, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl and tetrahydroisoquinolinyl which is either unsubstituted or substituted with one or more (e.g. one, two or three) substituents selected from halogen (e.g. fluorine or chlorine), cyano, oxo, nitro, —$OR^{10}$, —$SR^{10}$, —$NR^{10}R^{11}$, —$CONR^{10}R^{11}$, —$NR^{10}COR^{11}$, —$NR^{10}CONR^{11}R^{12}$, —$COR^{10}$, —$C(O)OR^{10}$, —$SO_2R^{10}$, —$SO_2NR^{10}R^{11}$, —$NR^{10}SO_2R^{11}$, $NR^{10}SO_2NR^{11}R^{12}$, —$NR^{10}C(O)OR^{11}$, optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, -$Q^2$-$R^{10}$, -$Q^2$-$NR^{10}CONR^{11}R^{12}$, -$Q^2$-$NR^{10}R^{11}$, -$Q^2$-$COR^{10}$-$Q^2$-$NR^{10}COR^{11}$, -$Q^2$-$NR^{10}C(O)OR^{11}$, -$Q^2$-$SO_2R^{10}$, $Q^2$-$CONR^{10}R^{11}$, -$Q^2$-$CO_2R^{10}$, -$Q^2$-$SO_2NR^{10}R^{11}$, -$Q^2$-$NR^{10}SO_2R^{11}$ and -$Q^2$-$NR^{10}SO_2NR^{11}R^{12}$, wherein the alkyl, alkoxy, alkenyl or alkynyl are optionally substituted with one or more substituents selected from halogen, hydroxyl, thiol, cyano, amino, nitro and $SF_5$, wherein $Q^2$ represents a covalent bond, an oxygen atom, a sulphur atom, —SO—, —$SO_2$—, —CO—, $C_1$-$C_6$ alkylene or optionally substituted $C_2$-$C_6$ alkenylene, and $R^{10}$, $R^{11}$, $R^{12}$ each independently represent hydrogen, optionally substituted $C_1$-$C_6$ alkyl, optionally substituted heterocyclyl, optionally substituted heteroaryl, optionally substituted aryl, or an optionally substituted cycloalkyl.

$R^6$ may represent a 3 to 10 membered heterocyclyl, cycloalkyl, heteroaryl or aryl ring selected from cyclopropyl, cyclobutyl, cyclopentyl, cyclohexyl, cycloheptyl, cyclooctyl, decahydronaphthalenyl, phenyl, naphthyl, naphthalenyl, pyridinyl, pyrazinyl, pyrimidinyl, pyridazinyl, furyl, pyrrolyl, oxazolyl, thiazolyl, pyrazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, dihydropyridinyl, quinoxalinyl, benzomorpholinyl, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl and tetrahydroisoquinolinyl which is either unsubstituted or substituted with one or more (e.g. one, two or three) substituents selected from halogen (e.g. fluorine or chlorine), cyano, oxo, nitro, $-OR^{10}$, $-SR^{10}$, $-NR^{10}R^{11}$, $-CONR^{10}R^{11}$, $-NR^{10}COR^{11}$, $-NR^{10}CONR^{11}R^{12}$, $-COR^{10}$, $-C(O)OR^{10}$, $-SO_2R^{10}$, $-SO_2NR^{10}R^{11}$, $-NR^{10}SO_2R^{11}$, $NR^{10}SO_2NR^{11}R^{12}$, $-NR^{10}C(O)OR^{11}$, optionally substituted $-C_1-C_6$ alkyl, optionally substituted $-C_1-C_6$ alkoxy, optionally substituted $-C_2-C_6$ alkenyl, optionally substituted $-C_2-C_6$ alkynyl, $-Q^2-R^{10}$, $-Q^2-NR^{10}CONR^{11}R^{12}$, $-Q^2-NR^{10}R^{11}$, $-Q^2-COR^{10}$, $-Q^2-NR^{10}COR^{11}$, $-Q^2-NR^{10}C(O)OR^{11}$, $-Q^2-SO_2R^{10}$, $Q^2-CONR^{10}R^{11}$, $-Q^2-CO_2R^{10}$, $-Q^2-SO_2NR^{10}R^{11}$, $-Q^2-NR^{10}SO_2R^{11}$ and $-Q^2-NR^{10}SO_2NR^{11}R^{12}$, wherein the alkyl, alkoxy, alkenyl or alkynyl are optionally substituted with one or more substituents selected from halogen, hydroxyl, thiol, cyano, amino, nitro and $SF_5$, wherein $Q^2$ represents a covalent bond, an oxygen atom, a sulphur atom, $-SO-$, $-SO_2-$, $-CO-$, $C_1-C_6$ alkylene or optionally substituted $C_2-C_6$ alkenylene, and $R^{10}$, $R^{11}$, $R^{12}$ each independently represent hydrogen, optionally substituted $C_1-C_6$ alkyl, optionally substituted heterocyclyl, optionally substituted heteroaryl, optionally substituted aryl, or an optionally substituted cycloalkyl.

$R^6$ may represent a ring selected from phenyl, thiazolyl, pyridinyl, pyrrolidinyl pyrazolyl, isoindolyl, isoxazolyl and cycloalkyl, wherein the ring is unsubstituted or substituted with one or more, in particular one or two, substituents selected from halogen (e.g. fluorine or chlorine), cyano, oxo, nitro, $-OR^{10}$, $-SR^{10}$, $-NR^{10}R^{11}$, $-CONR^{10}R^{11}$, $-NR^{10}COR^{11}$, $-NR^{10}CONR^{11}R^{12}$, $-COR^{10}$, $-C(O)OR^{10}$, $-SO_2R^{10}$, $-SO_2NR^{10}R^{11}$, $-NR^{10}SO_2R^{11}$, $NR^{10}SO_2NR^{11}R^{12}$, $-NR^{10}C(O)OR^{11}$, optionally substituted $-C_1-C_6$ alkyl, optionally substituted $-C_1-C_6$ alkoxy, optionally substituted $-C_2-C_6$ alkenyl, optionally substituted $-C_2-C_6$ alkynyl, $-Q^2-R^{10}$, $-Q^2-NR^{10}CONR^{11}R^{12}$, $-Q^2-NR^{10}R^{11}$, $-Q^2-COR^{10}$, $-Q^2-NR^{10}COR^{11}$, $-Q^2-NR^{10}C(O)OR^{11}$, $-Q^2-SO_2R^{10}$, $Q^2-CONR^{10}R^{11}$, $-Q^2-CO_2R^{10}$, $-Q^2-SO_2NR^{10}R^{11}$, $-Q^2-NR^{10}SO_2R^{11}$ and $-Q^2-NR^{10}SO_2NR^{11}R^{12}$, wherein the alkyl, alkoxy, alkenyl or alkynyl are optionally substituted with one or more substituents selected from halogen, hydroxyl, thiol, cyano, amino, nitro and $SF_5$, wherein $Q^2$ represents a covalent bond, an oxygen atom, a sulphur atom, $-SO-$, $-SO_2-$, $-CO-$, $C_1-C_6$ alkylene or optionally substituted $C_2-C_6$ alkenylene, and $R^{10}$, $R^{11}$, $R^{12}$ each independently represent hydrogen, optionally substituted $C_1-C_6$ alkyl, optionally substituted heterocyclyl, optionally substituted heteroaryl, optionally substituted aryl, or an optionally substituted cycloalkyl.

$R^6$ may represent a ring selected from phenyl, thiazolyl, pyridinyl, pyrrolidinyl pyrazolyl, isoindolyl and isoxazolyl, wherein the ring is unsubstituted or substituted with one or more, in particular one or two, substituents selected from halogen (e.g. fluorine or chlorine), cyano, oxo, nitro, $-OR^{10}$, $-SR^{10}$, $-NR^{10}R^{11}$, $-CONR^{10}R^{11}$, $-NR^{10}COR^{11}$, $-NR^{10}CONR^{11}R^{12}$, $-COR^{10}$, $-C(O)OR^{10}$, $-SO_2R^{10}$, $-SO_2NR^{10}R^{11}$, $-NR^{10}SO_2R^{11}$, $NR^{10}SO_2NR^{11}R^{12}$, $-NR^{10}C(O)OR^{11}$, optionally substituted $-C_1-C_6$ alkyl, optionally substituted $-C_1-C_6$ alkoxy, optionally substituted $-C_2-C_6$ alkenyl, optionally substituted $-C_2-C_6$ alkynyl, $-Q^2-R^{10}$, $-Q^2-NR^{10}CONR^{11}R^{12}$, $-Q^2-NR^{10}R^{11}$, $-Q^2-COR^{10}-Q^2-NR^{10}COR^{11}$, $-Q^2-NR^{10}C(O)OR^{11}$, $-Q^2-SO_2R^{10}$, $Q^2-CONR^{10}R^{11}$, $-Q^2-CO_2R^{10}$, $-Q^2-SO_2NR^{10}R^{11}$, $-Q^2-NR^{10}SO_2R^{11}$ and $-Q^2-NR^{10}SO_2NR^{11}R^{12}$, wherein the alkyl, alkoxy, alkenyl or alkynyl are optionally substituted with one or more substituents selected from halogen, hydroxyl, thiol, cyano, amino, nitro and $SF_5$, wherein $Q^2$ represents a covalent bond, an oxygen atom, a sulphur atom, $-SO-$, $-SO_2-$, $-CO-$, $C_1-C_6$ alkylene or optionally substituted $C_2-C_6$ alkenylene, and $R^{10}$, $R^{11}$, $R^{12}$ each independently represent hydrogen, optionally substituted $C_1-C_6$ alkyl, optionally substituted heterocyclyl, optionally substituted heteroaryl, optionally substituted aryl, or an optionally substituted cycloalkyl.

$R^6$ may represent a ring selected from cyclopropyl, cyclobutyl, cyclopentyl, cyclohexyl, cycloheptyl, cyclooctyl, decahydronaphthalenyl, phenyl, naphthyl, naphthalenyl, pyridinyl, pyrazinyl, pyrimidinyl, pyridazinyl, furyl, pyrrolyl, oxazolyl, thiazolyl, pyrazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, dihydropyridinyl, dihydropyrrolopyridinyl, benzoxazolyl, quinoxalinyl, benzomorpholinyl, tetrahydropyridopyrazinyl, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl and tetrahydroisoquinolinyl, wherein the ring is unsubstituted or substituted with one or more (e.g. one, two or three) substituents selected from halogen (for example, fluorine or chlorine), cyano, $C_1-C_4$ alkyl (e.g. propyl, isobutyl or tert butyl) or $C_1-C_2$ alkyl (e.g. methyl or ethyl), $C_1-C_4$ alkoxy or $C_1-C_2$ alkoxy (e.g. methoxy) wherein the alkyl and alkoxy may be optionally substituted with one or more fluorine, wherein the alkyl and alkoxy may be optionally substituted with one or more fluorine.

$R^6$ may represent a ring selected from cyclopropyl, cyclobutyl, cyclopentyl, cyclohexyl, cycloheptyl, cyclooctyl, decahydronaphthalenyl, phenyl, naphthyl, naphthalenyl, pyridinyl, pyrazinyl, pyrimidinyl, pyridazinyl, furyl, pyrrolyl, oxazolyl, thiazolyl, pyrazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, dihydropyridinyl, quinoxalinyl, benzomorpholinyl, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl and tetrahydroisoquinolinyl, wherein the ring is unsubstituted or substituted with one or more (e.g. one, two or three) substituents selected from halogen (for example, fluorine or chlorine), $C_1$-$C_4$ alkyl (e.g. propyl, isobutyl or tert butyl) or $C_1$-$C_2$ alkyl (e.g. methyl or ethyl), wherein the alkyl may be optionally substituted with one or more fluorine, wherein the alkyl and alkoxy may be optionally substituted with one or more fluorine.

In particular, $R^6$ may be selected from phenyl, thiazolyl, pyridinyl, pyrrolidinyl pyrazolyl, isoindolyl isoxazolyl and cyclopropyl, wherein the ring is unsubstituted or substituted with one or more (e.g. one, two or three) substituents selected from halogen (for example, fluorine or chlorine), cyano, $C_1$-$C_4$ alkyl (e.g. propyl, isobutyl or tert butyl) or $C_1$-$C_2$ alkyl (e.g. methyl or ethyl), $C_1$-$C_4$ alkoxy or $C_1$-$C_2$ alkoxy (e.g. methoxy), wherein the alkyl and alkoxy may be optionally substituted with one or more fluorine.

For example, $R^6$ may be selected from phenyl, thiazolyl, pyridinyl, pyrrolidinyl pyrazolyl, isoindolyl and isoxazolyl, wherein the ring is unsubstituted or substituted with one or more (e.g. one, two or three) substituents selected from halogen (for example, fluorine or chlorine), $C_1$-$C_4$ alkyl (e.g. propyl, isobutyl or tert butyl) or $C_1$-$C_2$ alkyl (e.g. methyl or ethyl), wherein the alkyl may be optionally substituted with one or more fluorine.

The present invention further relates to compounds of formula (I), or a pharmaceutically acceptable salt thereof, wherein:
$R^{1b}$, $R^{1c}$, $R^{1d}$ and $R^{1e}$ each independently represent $C_1$-$C_3$ alkyl which may be optionally substituted with one or more fluorine;
$R^{1a}$ and $R^{1g}$ each independently represent hydrogen, fluorine or $C_1$-$C_3$ alkyl which may be optionally substituted with one or more fluorine;
$R^{1f}$ is hydrogen, fluorine, $C_1$-$C_3$ alkyl which may be optionally substituted with one or more fluorine or together with $R^2$ forms a 5 membered heterocyclic ring which is optionally further substituted with fluorine, oxo, cyano, hydroxyl, amino, $C_1$-$C_6$ alkyl or $C_1$-$C_6$ alkoxy;
$R^2$ is hydrogen or $C_1$-$C_3$ alkyl or together with $R^{1f}$ forms a 5 membered heterocyclic ring which is optionally further substituted with fluorine, oxo, cyano, hydroxyl, amino, $C_1$-$C_6$ alkyl or $C_1$-$C_6$ alkoxy;
X represents $C(R^3)(R^4)$, wherein $R^3$ and $R^4$ each independently represent hydrogen, cyano or $C_1$-$C_3$ alkyl which may be optionally substituted with one or more halogen;
L is a covalent bond, —C(O)—, —$SO_2$—, —$CONR^5$—, —CO—$C_1$-$C_6$ alkylene or —CO—$C_2$-$C_6$ alkenylene wherein $R^5$ represents hydrogen or methyl;
A represents a 5 or 6 membered monocyclic heteroaryl or aryl which is substituted with one, two or three of -$Q^1$-$(R^6)_n$, or a 9 or 10 membered bicyclic heteroaryl or aryl which is optionally substituted with one, two or three of -$Q^1$-$(R^6)_n$, wherein each -$Q^1$-$(R^6)_n$ is the same or different;
n is 0 or 1;
$Q^1$, $R^6$ and n are as defined herein.

In particular, $Q^1$ is selected from halogen (e.g. fluorine, chlorine or bromine), cyano, oxo, nitro, —$OR^7$ (e.g hydroxyl), —$SR^7$ (e.g. thiol), —$NR^7R^8$ (e.g. amino or N,N-dimethylamino), —$CONR^7R^8$ (e.g. amido), —$NR^7COR^8$ (N-acetyl), —$NR^7CONR^8R^9$, —$COR^7$ (e.g. acetyl), —C(O)$OR^7$ (e.g. methoxycarbonyl or ethoxycarbonyl), —$SO_2R^7$ (e.g. methyl sulphonyl), —$SO_2NR^7R^8$ (e.g. dimethylaminosulphonyl), —$NR^7SO_2R^8$, $NR^7SO_2NR^8R^9$, —$NR^7C(O)OR^8$, optionally substituted —$C_1$-$C_4$ alkyl (e.g. propyl, isobutyl or tert butyl), optionally substituted $C_1$-$C_2$ alkyl (e.g. methyl or ethyl), optionally substituted —$C_1$-$C_6$ alkoxy, optionally substituted —$C_2$-$C_6$ alkenyl, optionally substituted —$C_2$-$C_6$ alkynyl, a covalent bond, an oxygen atom, a sulphur atom, —SO—, —$SO_2$—, —CO—, —C(O)O—, —$CONR^7$—, —$NR^7$— (e.g. methylamino), —$NR^7CO$—, —$NR^7CONR^8$—, —$SO_2NR^7$—, —$NR^7SO_2$—, —$NR^7SO_2NR^8$—, —$NR^7C(O)O$—, —$NR^7C(O)OR^8$—, optionally substituted $C_1$-$C_4$ alkylene (e.g. methylene or ethylene) or optionally substituted —$C_2$-$C_4$ alkenylene (e,g. vinyl), and $R^6$ is a 5 or 6 membered heteroaryl, heterocyclyl or aryl ring optionally substituted with one or two substituents independently selected from halogen, cyano, oxo, nitro, —$OR^{10}$, —$SR^{10}$, —$NR^{10}R^{11}$, —$CONR^{10}R^{11}$, —$NR^{10}COR^{11}$, —$NR^{10}CONR^{11}R^{12}$, —$COR^{10}$, —C(O)$OR^{10}$, —$SO_2R^{10}$, —$SO_2NR^{10}R^{11}$, —$NR^{10}SO_2R^{11}$, $NR^{10}SO_2NR^{11}R^{12}$, —$NR^{10}C(O)OR^{11}$, optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, -$Q^2$-$R^{10}$, -$Q^2NR^{10}CONR^{11}R^{12}$, -$Q^2$-$NR^{10}R^{11}$, $Q^2$-$COR^{10}$, -$Q^2NR^{10}COR^{11}$, $Q^2$-$NR^{10}C(O)OR^{11}$, -$Q^2$-$SO_2R^{10}$, $Q^2$-$CONR^{10}R^{11}$, -$Q^2$-$CO_2R^{10}$, -$Q^2$-$SO_2NR^{10}R^{11}$, -$Q^2$-$NR^{10}SO_2R$ and -$Q^2$-$NR^{10}SO_2NR^{11}R^{12}$, wherein $Q^2$ represents a covalent bond, an oxygen atom, a sulphur atom, —SO—, —$SO_2$—, —CO—, $C_1$-$C_6$ alkylene or optionally substituted $C_2$-$C_6$ alkenylene, and wherein $R^{10}$, $R^{11}$, $R^{12}$ each independently represent hydrogen or optionally substituted $C_1$-$C_6$ alkyl, wherein any alkyl, alkoxy, alkenyl, alkynyl, alkylene or alkenylene is optionally substituted with one or more (e.g. one, two, three or four) substituents selected from halogen, hydroxyl, thiol, cyano, amino, nitro and $SF_5$.

The present invention further relates to compounds of formula (I), or a pharmaceutically acceptable salt thereof, wherein:
$R^{1a}$. $R^{1b}$, $R^{1c}$, $R^{1d}$, $R^{1e}$ and $R^{1g}$ are each hydrogen;
$R^{1f}$ is hydrogen or together with $R^2$ forms a 5 membered heterocyclic ring which is optionally further substituted with one substituent;
$R^2$ is hydrogen or methyl or together with $R^{1f}$ forms a 5 membered heterocyclic ring which is optionally substituted with one further substituent;
X represents $C(R^3)(R^4)$, wherein $R^3$ represents hydrogen and $R^4$ represent hydrogen, cyano or $C_1$-$C_3$ alkyl;
L is a covalent bond, —C(O)—, —$SO_2$—, —CONH—, —CO—$C_1$-$C_3$ alkylene, in particular —C(O)—, —CO—methylene, or —CO-ethenylene;
A represents a 5 or 6 membered monocyclic heteroaryl or aryl which is substituted with one or two of -$Q^1$-$(R^6)_n$, or a 9 or 10 membered bicyclic heteroaryl or aryl which is unsubstituted or substituted with one or two of -$Q^1$-$(R^6)_n$;
each occurrence of -$Q^1$-$(R^6)_n$ is the same or different, wherein:
n is 0 or 1;
$Q^1$ represents halogen, in particular fluorine or chlorine, oxo, cyano, —$CONR^7$, —$NR^7COR^8$, $C_1$-$C_3$ alkyl optionally substituted with one or more fluorine, for example $CF_3$, —SO$_2$NH—, C$_1$-C$_3$ alkoxy for example methoxy, a covalent bond, an oxygen atom or C$_1$-C$_3$ alkylene for example methylene;

R$^6$ represents a 3 to 6 membered heterocyclyl, cycloalkyl, heteroaryl or aryl ring, in particular, R$^6$ represents phenyl, thiazolyl, pyridinyl, pyrrolidinyl, pyrazolyl, isoindolyl, isoxazolyl or cyclopropyl, wherein R$^6$ is unsubstituted or substituted with one or more substituents selected from halogen, cyano, C$_1$-C$_3$ alkyl for example methyl or C$_1$-C$_3$ alkoxy, for example methoxy;

R$^7$ and R$^8$ each independently represent hydrogen or C$_1$-C$_3$ alkyl.

The present invention further relates to compounds of formula (I), or a pharmaceutically acceptable salt thereof, wherein:

R$^{1a}$, R$^{1b}$, R$^{1c}$, R$^{1d}$, R$^{1e}$ and R$^{1g}$ are each hydrogen;
R$^{1f}$ is hydrogen or together with R$^2$ forms a 5 membered heterocyclic ring which is optionally further substituted with one substituent;
R$^2$ is hydrogen or methyl or together with R$^{1f}$ forms a 5 membered heterocyclic ring which is optionally substituted with one further substituent;
X represents C(R$^3$)(R$^4$), wherein R$^3$ represents hydrogen and R$^4$ represent hydrogen, cyano or C$_1$-C$_3$ alkyl;
L is a covalent bond, —C(O)—, —SO$_2$—, —CONH—, —CO—C$_1$-C$_3$ alkylene, in particular —CO-methylene, or —CO-ethenylene;
A represents a 5 or 6 membered monocyclic heteroaryl or aryl which is substituted with one or two of -Q$^1$-(R$^6$)$_n$, or a 9 or 10 membered bicyclic heteroaryl or aryl which is unsubstituted or substituted with one or two of -Q$^1$-(R$^6$)$_n$; each occurrence of -Q$^1$-(R$^6$)$_n$ is the same or different, wherein:
n is 0 or 1;
Q$^1$ represents halogen, in particular fluorine or chlorine, oxo, cyano, —CONR$^7$, —NR$^7$COR$^8$, C$_1$-C$_3$ alkyl optionally substituted with one or more fluorine, for example CF$_3$, —SO$_2$NH—, C$_1$-C$_3$ alkoxy for example methoxy, a covalent bond, an oxygen atom or C$_1$-C$_3$ alkylene for example methylene;
R$^6$ represents a 5 or 6 membered heterocyclyl, cycloalkyl, heteroaryl or aryl ring, in particular, R$^6$ represents phenyl, thiazolyl, pyridinyl, pyrrolidinyl or pyrazolyl, wherein R$^6$ is unsubstituted or substituted with one or more substituents selected from halogen or C$_1$-C$_3$ alkyl, for example, methyl;
R$^7$ and R$^8$ each independently represent hydrogen or C$_1$-C$_3$ alkyl.

Examples of ring A include those shown below:

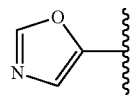
A

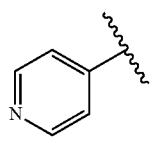
B

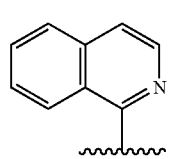
C

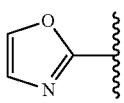
D

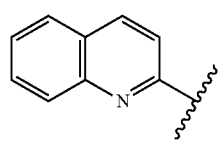
E

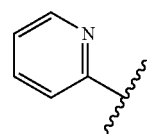
F

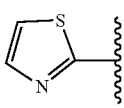
G

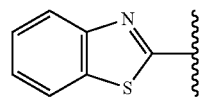
H

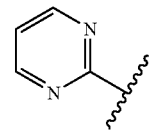
I

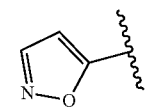
J

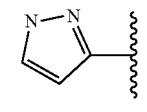
K

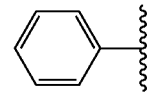
L

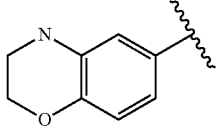
M

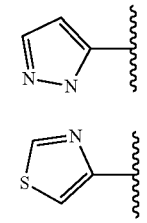
N

O

-continued

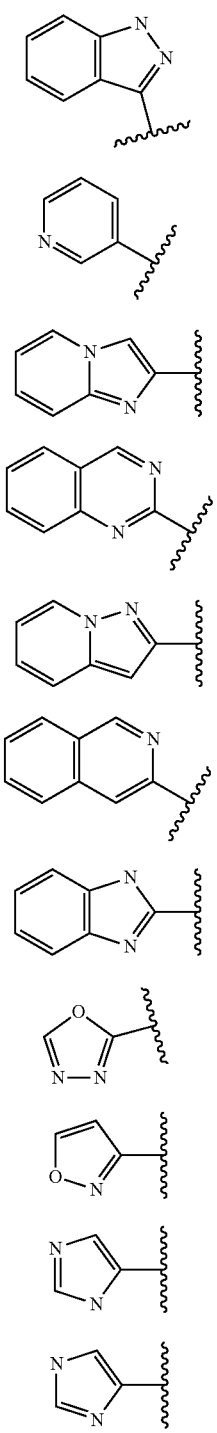

P

Q

R

S

T

U

V

W

X

Y

Z wherein ⸽ represents the point of attachment to the remainder of the molecule, i.e. to the amine nitrogen via L, and wherein the monocyclic rings are substituted with one or more of -Q$^1$-(R$^6$)$_n$ and wherein the bicyclic rings are optionally substituted with one or more of -Q$^1$-(R$^6$)$_n$. Hydrogen atoms attached to the ring nitrogen atoms have not been shown. It will be understood by the skilled person which ring nitrogen atoms are suitable for substitution and where not substituted the nitrogen may be bound to a hydrogen atom to complete its valency, where appropriate.

Examples of novel compounds of formula (I) include:
3-((quinolin-2-ylamino)methyl)pyrrolidine-1-carbonitrile
3-(((6-fluorobenzo[d]thiazol-2-yl)amino)methyl)pyrrolidine-1-carbonitrile
3-((isoquinolin-1-ylamino)methyl)pyrrolidine-1-carbonitrile
3-(((3-phenylpyridin-2-yl)amino)methyl)pyrrolidine-1-carbonitrile
3-(((4-phenylpyridin-2-yl)amino)methyl)pyrrolidine-1-carbonitrile
3-(((5-phenylpyridin-2-yl)amino)methyl)pyrrolidine-1-carbonitrile
3-(((6-phenylpyridin-2-yl)amino)methyl)pyrrolidine-1-carbonitrile
3-(((4-phenylpyrimidin-2-yl)amino)methyl)pyrrolidine-1-carbonitrile
(R)-3-(((5-phenylthiazol-2-yl)amino)methyl)pyrrolidine-1-carbonitrile
(S)-3-(((5-phenylthiazol-2-yl)amino)methyl)pyrrolidine-1-carbonitrile
3-(((6-(1H-pyrazol-4-yl)benzo[d]thiazol-2-yl)amino)methyl)pyrrolidine-1-carbonitrile
(R)-3-(((7-(1H-pyrazol-4-yl)quinazolin-2-yl)amino)methyl)pyrrolidine-1-carbonitrile
3-(((3-(1,3-dimethyl-1H-pyrazol-4-yl)phenyl)amino)methyl)pyrrolidine-1-carbonitrile
3-(((4-(1,3-dimethyl-1H-pyrazol-4-yl)phenyl)amino)methyl)pyrrolidine-1-carbonitrile
3-(((4-(1,3-dimethyl-1H-pyrazol-4-yl)-2-fluorophenyl)amino)methyl)pyrrolidine-1-carbonitrile
3-(((1-cyanopyrrolidin-3-yl)methyl)amino)isoquinoline-6-carbonitrile
3-(((1-cyanopyrrolidin-3-yl)methyl)amino)-N-methylisoquinoline-6-carboxamide
3-(((2-(isoindolin-2-yl)pyridin-4-yl)amino)methyl)pyrrolidine-1-carbonitrile
(S)-3-(((4-phenylpyrimidin-2-yl)amino)methyl)pyrrolidine-1-carbonitrile
N-((1-cyanopyrrolidin-3-yl)methyl)-2-phenyloxazole-5-carboxamide
N-((1-cyanopyrrolidin-3-yl)methyl)-3-phenylisoxazole-5-carboxamide
N-((1-cyanopyrrolidin-3-yl)methyl)-5-phenyl-1H-pyrazole-3-carboxamide
N-((1-cyanopyrrolidin-3-yl)methyl)-4-methyl-3-oxo-3,4-dihydro-2H-benzo[b][1,4]oxazine-6-carboxamide
N-((1-cyanopyrrolidin-3-yl)methyl)-4-(pyridin-4-yl)benzamide
N-((1-cyanopyrrolidin-3-yl)methyl)-3-(o-tolyl)-1H-pyrazole-5-carboxamide
N-((1-cyanopyrrolidin-3-yl)methyl)-2-phenylthiazole-4-carboxamide
N-((1-cyanopyrrolidin-3-yl)methyl)-4-(pyrrolidin-1-yl)picolinamide
N-((1-cyanopyrrolidin-3-yl)methyl)-1-(2,4-dichlorobenzyl)-1H-indazole-3-carboxamide
1-benzyl-N-((1-cyanopyrrolidin-3-yl)methyl)-1H-indazole-3-carboxamide
N-((1-cyanopyrrolidin-3-yl)methyl)-4-(N-phenylsulfamoyl)benzamide
N-((1-cyanopyrrolidin-3-yl)methyl)-3-(2-fluorophenyl)-1H-pyrazole-5-carboxamide
(E)-N-((1-cyanopyrrolidin-3-yl)methyl)-3-(2-fluoro-4-methoxyphenyl)acrylamide
N-((1-cyanopyrrolidin-3-yl)methyl)-5-(4-fluorophenyl)nicotinamide (S)—N-((1-cyanopyrrolidin-3-yl)methyl)-3-oxo-3,4-dihydro-2H-benzo[b][1,4]oxazine-6-carboxamide
(R)-6-chloro-N-((1-cyanopyrrolidin-3-yl)methyl)imidazo[1,2-a]pyridine-2-carboxamide
(R)—N-((1-cyanopyrrolidin-3-yl)methyl)pyrazolo[1,5-a]pyridine-2-carboxamide
2-([1,1'-biphenyl]-4-yl)-N-((1-cyanopyrrolidin-3-yl)methyl)-N-methylacetamide
N-((1-cyanopyrrolidin-3-yl)methyl)-5-phenyloxazole-2-carboxamide
N-((1-cyanopyrrolidin-3-yl)methyl)-6-(1-methyl-1H-pyrazol-4-yl)imidazo[1,2-a]pyridine-2-carboxamide
1-benzyl-N-((1-cyanopyrrolidin-3-yl)methyl)-5-methyl-1H-pyrazole-3-carboxamide
1-(3-chlorophenyl)-3-((1-cyanopyrrolidin-3-yl)methyl)urea
1-((1-cyanopyrrolidin-3-yl)methyl)-3-(2-fluoro-5-methylphenyl)urea
1-(3-benzylphenyl)-3-((1-cyanopyrrolidin-3-yl)methyl)urea
1-((1-cyanopyrrolidin-3-yl)methyl)-3-(2,4-dichlorophenyl)urea
1-((1-cyanopyrrolidin-3-yl)methyl)-3-(4-(trifluoromethyl)phenyl)urea
N-((1-cyanopyrrolidin-3-yl)methyl)-N-methyl-3-(2-methylthiazol-4-yl)benzenesulfonamide
N-((1-cyanopyrrolidin-3-yl)methyl)-N-methyl-4-((5-(trifluoromethyl)pyridin-2-yl)oxy)benzenesulfonamide
3-(1-((6-(5-methylisoxazol-4-yl)benzo[d]thiazol-2-yl)amino)ethyl)pyrrolidine-1-carbonitrile
3-(1-((6-(1H-pyrazol-4-yl)benzo[d]thiazol-2-yl)amino)ethyl)pyrrolidine-1-carbonitrile
3-(1-(isoquinolin-3-ylamino)ethyl)pyrrolidine-1-carbonitrile
3-((1-(1-cyanopyrrolidin-3-yl)ethyl)amino)isoquinoline-6-carbonitrile
3-((benzo[d]thiazol-2-ylamino)(cyano)methyl)pyrrolidine-1-carbonitrile
2-((1-(1-cyanopyrrolidin-3-yl)ethyl)amino)benzo[d]thiazole-6-carbonitrile
(3aR,6aS)-4-oxo-5-(5-phenylthiazol-2-yl)hexahydropyrrolo[3,4-c]pyrrole-2(1H)-carbonitrile
(R)-3-(3-chlorophenyl)-N-((1-cyanopyrrolidin-3-yl)methyl)isoxazole-5-carboxamide
(R)—N-((1-cyanopyrrolidin-3-yl)methyl)-1H-benzo[d]imidazole-2-carboxamide
(R)—N-((1-cyanopyrrolidin-3-yl)methyl)isoquinoline-3-carboxamide
(R)—N-((1-cyanopyrrolidin-3-yl)methyl)-5-phenylisoxazole-3-carboxamide
(R)—N-((1-cyanopyrrolidin-3-yl)methyl)-4-phenylpicolinamide
(R)—N-((1-cyanopyrrolidin-3-yl)methyl)-5-phenylpicolinamide
(R)—N-((1-cyanopyrrolidin-3-yl)methyl)-5-phenylthiazole-2-carboxamide
(R)—N-((1-cyanopyrrolidin-3-yl)methyl)-4-phenylthiazole-2-carboxamide
(R)—N-((1-cyanopyrrolidin-3-yl)methyl)-1-phenyl-1H-pyrazole-3-carboxamide
(R)—N-((1-cyanopyrrolidin-3-yl)methyl)-2-phenyl-1H-imidazole-5-carboxamide
(R)-7-chloro-N-((1-cyanopyrrolidin-3-yl)methyl)imidazo[1,2-a]pyridine-2-carboxamide
(R)-3-(2-chlorophenyl)-N-((1-cyanopyrrolidin-3-yl)methyl)isoxazole-5-carboxamide
(R)-3-(4-chlorophenyl)-N-((1-cyanopyrrolidin-3-yl)methyl)isoxazole-5-carboxamide
(R)-5-(3-cyanophenyl)-N-((1-cyanopyrrolidin-3-yl)methyl)-1,3,4-oxadiazole-2-carboxamide
(S)-5-(3-cyanophenyl)-N-((1-cyanopyrrolidin-3-yl)methyl)-1,3,4-oxadiazole-2-carboxamide
(R)—N-((1-cyanopyrrolidin-3-yl)methyl)-1-phenyl-1H-imidazole-4-carboxamide
(R)-1-(3-cyanophenyl)-N-((1-cyanopyrrolidin-3-yl)methyl)-1H-imidazole-4-carboxamide
(R)-1-(4-cyanophenyl)-N-((1-cyanopyrrolidin-3-yl)methyl)-1H-imidazole-4-carboxamide
(R)—N-((1-cyanopyrrolidin-3-yl)methyl)-1-(2-methoxyphenyl)-1H-imidazole-4-carboxamide
(R)—N-((1-cyanopyrrolidin-3-yl)methyl)-1-(3-methoxyphenyl)-1H-imidazole-4-carboxamide
(R)—N-((1-cyanopyrrolidin-3-yl)methyl)-6-(1H-pyrazol-4-yl)imidazo[1,2-a]pyridine-2-carboxamide
(R)—N-((1-cyanopyrrolidin-3-yl)methyl)-6-(1H-pyrazol-3-yl)imidazo[1,2-a]pyridine-2-carboxamide
(R)—N-((1-cyanopyrrolidin-3-yl)methyl)-7-cyclopropylimidazo[1,2-a]pyridine-2-carboxamide
(R)-1-benzyl-N-((1-cyanopyrrolidin-3-yl)methyl)-1H-imidazole-4-carboxamide
(R)—N-((1-cyanopyrrolidin-3-yl)methyl)-1-(cyclopropylmethyl)-1H-imidazole-4-carboxamide or pharmaceutically acceptable salts thereof.

It should be noted that each of the chemical compounds listed above represents a particular and independent aspect of the invention.

According to a further aspect of the invention there is provided a process for the preparation of a compound of formula (I) or a pharmaceutically acceptable salt thereof comprising the steps of reacting an amine of formula (II) with a compound A-L-LG to form a compound of formula (III):

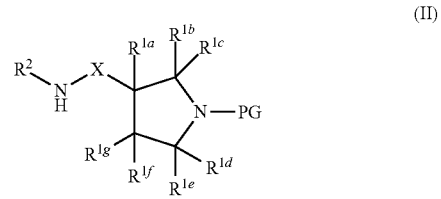

(II)

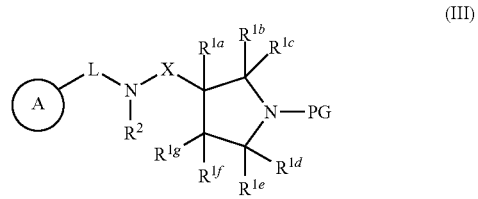

(III)

wherein $R^{1a}$, $R^{1b}$, $R^{1c}$, $R^{1d}$, $R^{1e}$, $R^{1f}$, $R^{1g}$, $R^2$, A, X, L and m, are as defined elsewhere, PG is an amine protecting group and LG is a suitable leaving group. The protecting group may be but is not limited to BOC. It is clear to a person skilled in the art to combine or adjust such a protecting chemical group. The leaving group may be but is not limited to halogen. It is clear to a person skilled in the art to combine or adjust such a chemical leaving group. The protecting group may be removed to leave the free amine according to formula (IV) which can then be treated with cyanogen bromide to form compounds according to formula (I):

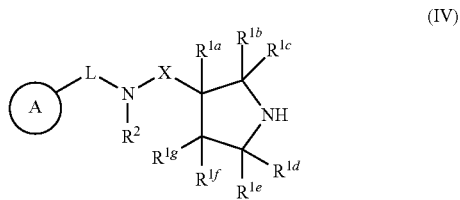

(IV)

wherein $R^{1a}$, $R^{1b}$, $R^{1c}$, $R^{1d}$, $R^{1e}$, $R^{1f}$, $R^{1g}$, $R^2$, A, X, L and m are as defined elsewhere.

According to a further aspect of the invention there is provided a process for the preparation of a compound of formula (I) or a pharmaceutically acceptable salt thereof comprising the steps of reacting an amine of formula (IV) with cyanogen bromide to form N—CN compounds:

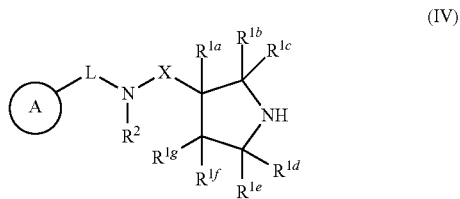

(IV)

wherein $R^{1a}$, $R^{1b}$, $R^{1c}$, $R^{1d}$, $R^{1e}$, $R^{1f}$, $R^{1g}$, $R^2$, A, X, L and m are as defined elsewhere.

According to a further aspect of the invention there is provided a pharmaceutical composition comprising a compound of the invention.

Pharmaceutical compositions of this invention comprise any of the compounds of the invention combined with any pharmaceutically acceptable carrier, adjuvant or vehicle. Examples of pharmaceutically acceptable carriers, are known to those skilled in the art and include but are not limited to preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may be in the form of, for example, tablets, capsules, powders, granules, elixirs, lozenges, suppositories, syrups and liquid preparations including suspensions and solutions. The term "pharmaceutical composition" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms.

The compounds of the invention can be used in the treatment of disorders and diseases related to USP30 inhibition.

Conditions Involving Mitochondrial Dysfunction

The compounds of the invention can be used in the treatment of disorders or diseases having a component relating to mitochondrial dysfunction, particularly disorders or diseases linked to DUB activity. More particularly, disorders or diseases link to USP30 activity.

The compounds described herein may be used in the manufacture of a medicament for the treatment of conditions involving mitochondrial dysfunction.

In a further aspect of the invention there is provided a method of treatment or prevention of a condition involving mitochondrial dysfunction, the method comprising administering a pharmaceutically effective amount of a compound of the invention or a pharmaceutical composition thereof to an individual diagnosed with a condition involving mitochondrial dysfunction.

Mitochondrial dysfunctions result from defects of the mitochondria, which are specialized compartments present in every cell of the body except red blood cells. When mitochondria fail, less and less energy is generated within the cell and cell injury or even cell death will follow. If this process is repeated throughout the body the life of the subject in whom this is happening is severely compromised. Diseases of the mitochondria appear most often in organs that are very energy demanding such as the brain, heart, liver, skeletal muscles, kidney and the endocrine and respiratory system.

The condition involving mitochondrial dysfunction may be selected from a condition involving a mitophagy defect, a condition involving a mutation in mitochondrial DNA, a condition involving mitochondrial oxidative stress, a condition involving a defect in mitochondrial membrane potential, mitochondrial biogenesis, a condition involving a defect in mitochondrial shape or morphology, and a condition involving a lysosomal storage defect.

In particular, the condition involving mitochondrial dysfunction may be selected from a neurodegenerative disease; multiple sclerosis (MS), mitochondrial myopathy, encephalopathy, lactic acidosis, and stroke-like episodes (MELAS) syndrome; Leber's hereditary optic neuropathy (LHON); cancer; neuropathy, ataxia, retinitis pigmentosa-maternally inherited Leigh syndrome (NARP-MILS); Danon disease; diabetes; diabetic nephropathy; metabolic disorders; heart failure; ischemic heart disease leading to myocardial infarction; psychiatric diseases, for example schizophrenia; multiple sulfatase deficiency (MSD); mucolipidosis II (ML II); mucolipidosis III (ML III); mucolipidosis IV (ML IV); GM1-gangliosidosis (GM1); neuronal ceroid-lipofuscinoses (NCL1); Alpers disease; Barth syndrome; Beta-oxidation defects; carnitine-acyl-carnitine deficiency; carnitine deficiency; creatine deficiency syndromes; co-enzyme Q10 deficiency; complex I deficiency; complex II deficiency; complex III deficiency; complex IV deficiency; complex V deficiency; COX deficiency; chronic progressive external ophthalmoplegia syndrome (CPEO); CPT I deficiency; CPT II deficiency; glutaric aciduria type II; Kearns-Sayre syndrome; lactic acidosis; long-chain acyl-CoA dehydrogenase deficiency (LCHAD); Leigh disease or syndrome; lethal infantile cardiomyopathy (LIC); Luft disease; glutaric aciduria type II; medium-chain acyl-CoA dehydrogenase deficiency (MCAD); myoclonic epilepsy and ragged-red fiber (MERRF) syndrome; mitochondrial cytopathy; mitochondrial recessive ataxia syndrome; mitochondrial DNA depletion syndrome; myoneurogastointestinal disorder and encephalopathy; Pearson syndrome; pyruvate dehydrogenase deficiency; pyruvate carboxylase deficiency; POLG mutations; medium/short-chain 3-hydroxyacyl-CoA dehydrogenase (M/SCHAD) deficiency; and very long-chain acyl-CoA dehydrogenase (VLCAD) deficiency; and age-dependent decline in cognitive function and muscle strength.

The condition involving mitochondrial dysfunction may be a CNS disorder, for example a neurodegenerative disease.

Neurodegenerative diseases include, but are not limited to, Parkinson's disease, Alzheimer's disease, amyotrophic lateral sclerosis (ALS), Huntington's disease, ischemia, stroke, dementia with Lewy bodies, and frontotemperal dementia.

In a particular embodiment, the compounds of the invention are useful in the treatment of Parkinson's disease, including, but not limited to, PD related to mutations in α-synuclein, parkin and PINK1, autosomal recessive juvenile Parkinson's disease (AR-JP) where parkin is mutated.

The compounds of the invention or pharmaceutical compositions thereof as described herein may be combined with one or more additional agents when used for the treatment of conditions involving mitochondrial dysfunction. The compounds may be combined with one or more additional agents selected from levodopa, a dopamine agonist, a monoamino oxygenase (MAO) B inhibitor, a catechol O-methyltransferase (COMT) inhibitor, an anticholinergic, riluzole, amantadine, a cholinesterase inhibitor, memantine, tetrabenazine, an antipsychotic, diazepam, clonazepam, an antidepressant, and an anti-convulsant.

Cancer

Compounds of the invention also have use in the treatment of cancer and more particularly in the treatment of cancer linked to DUB activity, especially USP30 activity.

The compounds as described herein may also be used in the manufacture of a medicament for the treatment of a cancer. In a further aspect of the invention there is provided a method of treatment or prevention of a cancer, the method comprising administering a pharmaceutically effective amount of a compound of the invention or a pharmaceutical composition thereof to an individual suffering from a cancer.

The compounds of the invention also have use in the treatment of cancer linked to mitochondrial dysfunction.

In one embodiment, the compounds of the invention have use in the treatment of cancer where apoptotic pathways are dysregulated and more particularly where proteins of the BCL-2 family are mutated, or over or under expressed.

References to "cancer" or "tumour" include but are not limited to breast, ovarian, prostate, lung, kidney, gastric, colon, testicular, head and neck, pancreas, brain, melanoma, bone or other cancers of tissue organs and cancers of the blood cells such as lymphomas and leukaemias. Particular cancers include lymphoma, multiple myeloma, colorectal cancer, and non-small cell lung carcinoma.

The compounds of the invention or pharmaceutical compositions thereof as described herein may be combined with one or more additional agents when used for the treatment of cancer. The compounds may be combined with an additional anti-tumour therapeutic agent, for example chemotherapeutic drugs or inhibitors of other regulatory proteins. In one embodiment the additional anti-tumour therapeutic agent is a BH-3 mimetic. In a further embodiment BH-3 mimetics may be selected from but not limited to one or more of ABT-737, ABT-199, ABT-263, and Obatoclax. In a further embodiment the additional anti-tumour agent is a chemotherapeutic agent. Chemotherapeutic agents may be selected from but not limited to, olaparib, mitomycin C, cisplatin, carboplatin, oxaliplatin, ionizing radiation (IR), camptothecin, irinotecan, topotecan, temozolomide, taxanes, 5-fluoropyrimidines, gemcitabine, and doxorubicin.

Dosage Forms

For treating a mitochondrial dysfunction disorder, the pharmaceutical compositions of the invention may be designed for administration by the oral, parenteral or mucosal route and the choice or the specific form of composition is dependent on the administration route. Thus for oral administration the composition may be in the form, for example, of tablets, lozenges, dragees, films, powders, elixirs, syrups, liquid preparations including dispersions, suspensions, emulsions, solutions or sprays, cachets, granules, capsules, etc. For administration to mucosa the composition may be in the form of sprays, inhalants, dispersions, suspensions, emulsions, solutions, gels, patches, films, ointments, creams, lotions, suppositories etc. For parenteral administration the composition is in the form of a liquid preparation such as a solution, dispersion, emulsion or suspension including liposome compositions.

For treating a CNS disorder, the compounds of the invention must have the ability to pass across the blood-brain barrier. As such, such compounds have the ability to enter the central nervous system of a patient. Alternatively, the pharmaceutical compositions of the present invention can bypass the blood brain barrier through use of compositions and methods known in the art for bypassing the blood brain barrier or can be injected directly into the brain. Suitable areas for injection include the cerebral cortex, cerebellum, midbrain, brainstem, hypothalamus, spinal cord and ventricular tissue, and areas of the PNS including the carotid body and the adrenal medulla. Further dosage forms include those suitable for oral delivery including, but not limited to tablets, dragees, powders, elixirs, syrups, liquid preparations including suspensions, sprays, inhalants, tablets, lozenges, emulsions, solutions, cachets, granules and capsules. For parenteral administration, preparations include sterile aqueous, aqueous-organic, and organic solutions, suspensions and emulsions.

For treating a cancer, the pharmaceutical compositions of the invention may be administered in any effective manner suitable for targeting cancer cells, for example orally in any orally acceptable dosage form including, but not limited to tablets, dragees, powders, elixirs, syrups, liquid preparations including suspensions, sprays, inhalants, tablets, lozenges, emulsions, solutions, cachets, granules and capsules. Preparations according to the invention for parenteral administration include sterile aqueous, aqueous-organic, and organic solutions, suspensions and emulsions.

Such dosage forms are prepared according to techniques known in the art of pharmaceutical formulation. When in the form of sprays or inhalants the pharmaceutical compositions may be administered nasally. Suitable formulations for this purpose are known to those skilled in the art.

The pharmaceutical compositions of the invention may be administered by injection and may be in the form of a sterile liquid preparation for injection, including liposome preparations. The pharmaceutical compositions of the invention may also be in the form of suppositories for rectal administration. These are formulated so that the pharmaceutical composition is solid at room temperature and liquid at body temperature to allow release of the active compound.

The dosages may be varied depending upon the requirements of the patient, the severity of the condition being treated, and the compound being employed. Determination of the proper dosage for a particular situation is within the remit of the person skilled in the skill of the art. Generally, treatment is initiated with smaller dosages which are less than the optimal dose of the compound. Thereafter the dosage is increased by small increments until the optimum effect under the circumstances is reached.

The magnitude of an effective dose of a compound will, of course, vary with the nature of the severity of the condition to be treated and with the particular compound and its route of administration. The selection of appropriate dosages is within the ability of one of ordinary skill in this art, without undue burden. The daily dose range is about 10 μg to about 100 mg per kg body weight of a human and non-human animal and in general may be around 10 μg to 30 mg per kg body weight per dose. The above dose may be given from one to three times per day.

Synthetic Methodologies

Compounds of the invention may be prepared via a variety of synthetic routes. Exemplary routes to certain compounds of the invention are shown below. Representative compounds of the present invention can be synthesized in accordance with the general synthetic methods described below and are illustrated more particularly in the schemes that follow. Since the schemes are an illustration, the invention should not be construed as being limited by the chemical reactions and conditions expressed. The preparation of the various starting materials used in the schemes is well within the skill of persons versed in the art. Those skilled in the art appreciate that, where appropriate, the individual transformations within a scheme can be completed in a different order. The following schemes describe general synthetic methods whereby intermediate and target compounds of the present invention may be prepared. Additional representative compounds and stereoisomers, racemic mixtures, diastereomers and enantiomers thereof can be synthesized using the intermediates prepared in accordance to the general schemes and other materials, compounds and reagents known to those skilled in the art. All such compounds, stereoisomers, racemic mixtures, diastereomers and enantiomers thereof are intended to be encompassed within the scope of the present invention.

All the compounds were characterised by liquid chromatography-mass spectroscopy (LCMS) and $^1$H NMR.

ABBREVIATIONS

BINAP 2,2'-Bis(diphenylphosphino)-1,1'-binaphthyl
Boc Tert-butoxycarbonyl
br Broad (NMR signal)
CDI 1,1-Carbonyldiimidazole
d Doublet (NMR signal)
dba dibenzylideneacetone
DBU 1,8-Diazabicyclo[5.4.0]undec-7-ene
DCM Dichloromethane
DIPEA Diisopropylethylamine
DMA Dimethylacetamide
DMF N,N-Dimethylformamide
DMSO Dimethylsulphoxide
dppf 1,1'-Bis(diphenylphosphino)ferrocene
ES Electrospray
EtOAc Ethyl acetate
EtOH Ethanol
h Hour(s)
Hal Halogen, e.g. F, Cl, Br, I
HATU 1-[Bis(dimethylamino)methylene]-1H-1,2,3-triazolo[4,5-b]pyridinium3-oxid hexafluorophosphate
m Multiplet (NMR signal)
MeCN Acetonitrile
Me-Dalphos Di(1-adamantyl)-2-dimethylaminophenylphosphine
MeOH Methanol
MTBE Methyl tert-butyl ether
NMP N-methyl-2-pyrrolidone
PE Petroleum ether
rt Room temperature
Ruphos 2-Dicyclohexylphosphino-2',6'-diisopropoxybiphenyl
s Singlet (NMR signal)
t Triplet (NMR signal)
T3P Propylphosphonic anhydride
TBD 1,5,7-triazabicyclo[4.4.0]dec-5-ene
TEA Triethylamine
TFA Trifluoroacetic acid
THF Tetrahydrofuran
TLC Thin Layer Chromatography
TMA Trimethylaluminium LCMS Methods

| Method A | | |
|---|---|---|
| Column | X-bridge C18, 50 × 4.6 mm, 3.5 μm or equivalent | |
| Mobile Phase | (A) 0.1% Ammonia in water | |
| | (B) 0.1% Ammonia in MeCN | |
| Flow Rate | 1.0 mL/min | |
| Gradient | Time | % B |
| | 0.01 | 5 |
| | 5.00 | 90 |
| | 5.80 | 95 |
| | 7.20 | 95 |
| | 7.21 | 5 |
| | 10.00 | 5 |

| Method B | | |
|---|---|---|
| Column | BEH C18, 50 × 2.1 mm, 1.7 μm or equivalent | |
| Mobile Phase | (A) 5 mM Ammonium acetate + 0.1% formic acid in water | |
| | (B) 0.1% Formic acid in MeCN | |
| Flow Rate | 0.45 mL/min | |
| Gradient | Time | % B |
| | 0.01 | 2 |
| | 0.50 | 2 |
| | 5.00 | 90 |
| | 6.00 | 95 |
| | 7.00 | 95 |
| | 7.01 | 2 |
| | 8.00 | 2 |

| Method C | | |
|---|---|---|
| Column | BEH C18, 50 × 2.1 mm, 1.7 μm or equivalent | |
| Mobile Phase | (A) 5 mM Ammonium acetate + 0.1% formic acid in water | |
| | (B) 0.1% Formic acid in MeCN | |
| Flow Rate | 0.55 mL/min | |
| Gradient | Time | % B |
| | 0.01 | 5 |
| | 0.40 | 5 |
| | 0.80 | 35 |
| | 1.20 | 55 |
| | 2.50 | 100 |
| | 3.30 | 100 |
| | 3.31 | 5 |
| | 4.00 | 5 |

| Method D | | |
|---|---|---|
| Column | Agilent TC-C18, 50 × 2.1 mm, 51 μm | |
| Mobile Phase | (A) 0.04% TFA in water | |
| | (B) 0.02% TFA in MeCN | |
| Flow Rate | 0.8 mL/min | |
| Gradient | Time | % B |
| | 0 | 0 |
| | 0.4 | 0 |
| | 3.4 | 100 |
| | 4 | 100 |
| Temperature | 40° C. | |

| Method E | | |
|---|---|---|
| Column | Agilent TC-C18, 50 × 2.1 mm, 5 μm | |
| Mobile Phase | (A) 0.04% TFA in water | |
| | (B) 0.02% TFA in MeCN | |
| Flow Rate | 0.8 mL/min | |
| Gradient | Time | % B |
| | 0 | 0 |
| | 0.4 | 1 |
| | 3.4 | 100 |
| | 4 | 100 |
| Temperature | 50° C. | |

Method F

| Column | XBridge ShieldRP18, 2.1 × 50 mm, 5 μm |
|---|---|
| Mobile Phase | (A) 0.05% Ammonia in water |
| | (B) MeCN |
| Flow Rate | 0.8 mL/min |

| Gradient | Time | % B |
|---|---|---|
| | 0 | 0 |
| | 0.4 | 5 |
| | 3.4 | 100 |
| | 4 | 100 |

Temperature 40° C.

Method G

| Column | X-bridge C18, 250 × 4.6 mm, 5 μm or equivalent |
|---|---|
| Mobile Phase | (A) 0.1% Ammonia in water |
| | (B) 0.1% Ammonia in MeCN |
| Flow Rate | 1.0 mL/min |

| Gradient | Time | % B |
|---|---|---|
| | 0.01 | 5 |
| | 5.00 | 5 |
| | 10.00 | 30 |
| | 15.00 | 30 |
| | 25.00 | 60 |
| | 30.00 | 90 |
| | 35.00 | 90 |
| | 35.01 | 5 |
| | 40.00 | 5 |

Example 1 3-((Quinolin-2-ylamino)methyl)pyrrolidine-1-carbonitrile

Step a. To a solution of tert-butyl 3-(aminomethyl)pyrrolidine-1-carboxylate (0.2 mmol), 2-chloroquinoline (0.2 mmol) and sodium tert-butoxide (0.6 mmol) in toluene (1 ml) were added catalytic amounts of allyl palladium and Me-Dalphos at rt under nitrogen. The reaction mixture was stirred at 65° C. for 16 h. The resulting mixture was concentrated under reduced pressure. The resulting residue was purified by prep-TLC (PE:EtOAc 1:1) yielding tert-butyl 3-((quinolin-2-ylamino)methyl)-pyrrolidine-1-carboxylate. MS: ES+ 328.4.

Step b. To a solution of tert-butyl tert-butyl 3-((quinolin-2-ylamino)methyl)pyrrolidine-1-carboxylate in EtOAc (1 mL) was added 4 M HCl in EtOAc (1 ml). The reaction mixture was stirred at rt for 2 h. The resulting mixture was concentrated under reduced pressure. The residue N-(pyrrolidin-3-ylmethyl)-quinolin-2-amine was used directly in the next step without further purification. MS: ES+ 228.1.

Step c. To a solution of N-(pyrrolidin-3-ylmethyl)quinolin-2-amine in EtOH (2 mL) was added cyanogen bromide (0.2 mmol) and NaHCO₃ (0.6 mmol). The reaction mixture was stirred at rt for 16 h. The resulting mixture was concentrated under reduced pressure. The crude was purified by preparative reverse phase HPLC (A: 0.078% ammonium acetate in water, B: MeCN) yielding the title compound (1.5 mg, 0.005 mmol). LCMS: Method E, retention time 1.98 min, MS: ES+ 254.1.

Compounds in Table 1 were synthesised using a procedure similar to that described for Example 1.

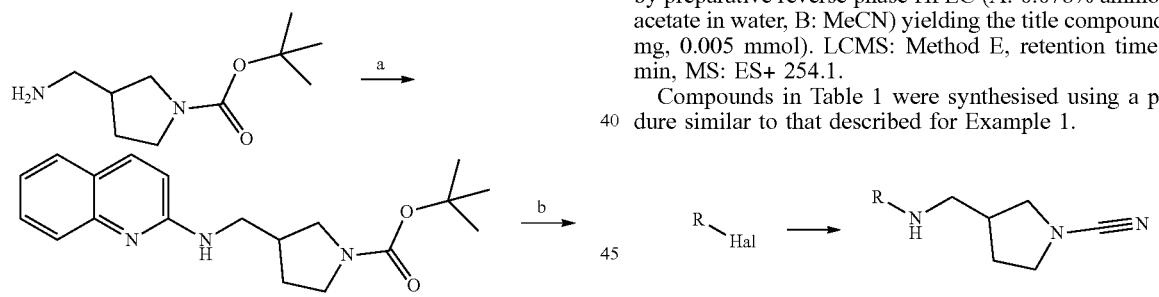

TABLE 1

| Ex | R | Name | LCMS Method | LCMS RT (min) | MS ES+ |
|---|---|---|---|---|---|
| 2 | 6-Fluorobenzo[d]thiazol-2-yl | 3-(((6-Fluorobenzo[d]thiazol-2-yl)amino)methyl)pyrrolidine-1-carbonitrile | E | 2.18 | 277.1 |
| 3 | Isoquinolin-1-yl | 3-((Isoquinolin-1-ylamino)methyl)pyrrolidine-1-carbonitrile | E | 1.775 | 253.1 |

TABLE 1-continued

| Ex | R | Name | LCMS Method | LCMS RT (min) | MS ES+ |
|---|---|---|---|---|---|
| 4 | | 3-(((3-Phenylpyridin-2-yl)amino)methyl)pyrrolidine-1-carbonitrile | E | 1.915 | 279.2 |
| 5 | | 3-(((4-Phenylpyridin-2-yl)amino)methyl)pyrrolidine-1-carbonitrile | E | 2.239 | 279.0 |
| 6 | | 3-(((5-Phenylpyridin-2-yl)amino)methyl)pyrrolidine-1-carbonitrile | E | 2.225 | 279.0 |
| 7 | | 3-(((6-Phenylpyridin-2-yl)amino)methyl)pyrrolidine-1-carbonitrile | E | 2.16 | 279.0 |
| 8 | | 3-(((4-Phenylpyrimidin-2-yl)amino)methyl)pyrrolidine-1-carbonitrile | E | 2.35 | 280.0 |

Example 9 (R)-3-(((5-Phenylthiazol-2-yl)amino)methyl)pyrrolidine-1-carbonitrile

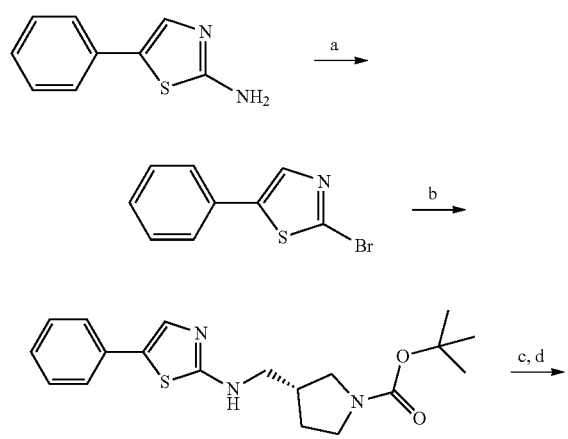

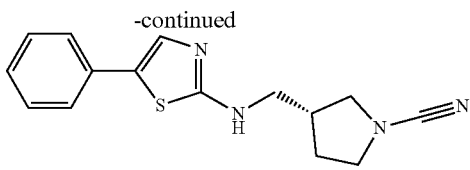

Step a. To a solution of 5-phenylthiazol-2-amine (10.0 g, 56.8 mmol) in MeCN (200 ml) was added CuBr$_2$ (15.2 g, 68.18 mmol) at 0° C. and stirred for 10 min. Tert-butyl nitrite (8.10 ml, 68.2 mmol) was added drop wise to the reaction mixture at 0° C. The reaction mixture was stirred at rt for 2 h. The resulting reaction mixture filtered through celite hyflow. The celite cake was washed with MeCN (2×100 ml). The filtrate was concentrated under reduced pressure and diluted with water (100 ml). The resulting mixture was extracted with EtOAc (3×80 ml). The combined organic phase was collected, dried over Na$_2$SO$_4$, filtered and concentrated under reduced pressure. The resulting residue was purified by column chromatography (30% EtOAc in hexane) yielding 2-bromo-5-phenylthiazole (2.00 g, 8.33 mmol).

LCMS: Method B, 4.78 min, MS: ES+ 240.20; ¹H NMR (400 MHz, DMSO-d₆) δ ppm 8.13 (s, 1H), 7.65-7.67 (m, 2H), 7.45-7.49 (m, 2H), 7.39-7.43 (m, 1H).

Step b. To a solution of 2-bromo-5-phenylthiazole (0.30 g, 1.24 mmol) in EtOH (5 ml) was added tert-butyl (R)-3-(aminomethyl)pyrrolidine-1-carboxylate (0.274 g, 1.36 mmol) at rt. The reaction mixture was heated at 100° C. for 120 h. The resulting reaction mixture was cooled to rt and concentrated under reduced pressure. The crude residue was purified by column chromatography (40% EtOAc in hexane) yielding tert-butyl (R)-3-(((5-phenylthiazol-2-yl)amino)methyl)pyrrolidine-1-carboxylate (0.12 g, 0.33 mmol). LCMS: Method B, 4.27 min, MS: ES+ 360.43.

Step c. To a solution of tert-butyl (R)-3-(((5-phenylthiazol-2-yl)amino)methyl)pyrrolidine-1-carboxylate (0.11 g, 0.30 mmol) in DCM (8 ml) was added TFA (0.5 ml) at 0° C. The reaction mixture was stirred at rt for 1 h. The resulting reaction mixture was concentrated under reduced pressure. The obtained residue was redistilled using DCM (2×5 ml). The obtained residue was triturated with diethyl ether (2×5 ml) yielding (R)-5-phenyl-N-(pyrrolidin-3-ylmethyl)thiazol-2-amine TFA salt (0.095 g, 0.25 mmol). This material was directly used for the next step without further purification.

Step d. To a solution of (R)-5-phenyl-N-(pyrrolidin-3-ylmethyl)thiazol-2-amine TFA salt (0.09 g, 0.34 mmol) in THF (10 ml) was added K₂CO₃ (0.143 g, 1.00 mmol) at 0° C. The reaction mixture was stirred at 0° C. for 10 min. Cyanogen bromide (0.044 g, 0.41 mmol) was added to the reaction mixture at 0° C. The reaction mixture was stirred at rt for 30 min. The resulting reaction mixture was poured into water (20 ml) and extracted with EtOAc (2×25 ml). The combined organic phase was collected, dried over Na₂SO₄, filtered and concentrated under reduced pressure. The resulting residue was purified by column chromatography (70% EtOAc in hexane) yielding title compound (0.038 g, 0.13 mmol). LCMS: Method B, 3.37 min, MS: ES+ 285.33; ¹H NMR (400 MHz, DMSO-d₆) δ ppm 7.94 (m, 1H), 7.33-7.49 (m, 5H), 7.16-7.22 (m, 1H), 3.39-3.51 (m, 2H), 3.27-3.36 (m, 3H), 3.12-3.18 (m, 1H), 2.53-2.59 (m, 1H), 1.94-2.04 (m, 1H), 1.64-1.72 (m, 1H).

Example 10 (S)-3-(((5-Phenylthiazol-2-yl)amino)methyl)pyrrolidine-1-carbonitrile

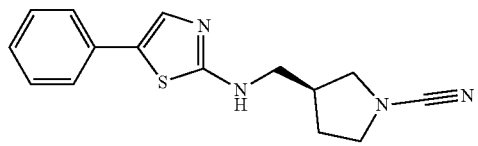

The title compound was synthesised by a procedure similar to Example 9 using tert-butyl (S)-3-(aminomethyl)pyrrolidine-1-carboxylate. LCMS: Method B, 3.40 min, MS: ES+ 285.68; ¹H NMR (400 MHz, DMSO-d₆) δ ppm 7.94 (br t, J=5.2 Hz, 1H), 7.47 (s, 1H), 7.42-7.44 (m, 2H), 7.32-7.35 (m, 2H), 7.17-7.21 (m, 1H), 3.42-3.49 (m, 2H), 3.34-3.39 (m, 1H), 3.26-3.29 (m, 2H), 3.13-3.17 (m, 1H), 2.53-2.59 (m, 1H), 1.95-2.03 (m, 1H), 1.62-1.71 (m, 1H).

Example 11 3-(((6-(1H-Pyrazol-4-yl)benzo[d]thiazol-2-yl)amino)methyl)pyrrolidine-1-carbonitrile

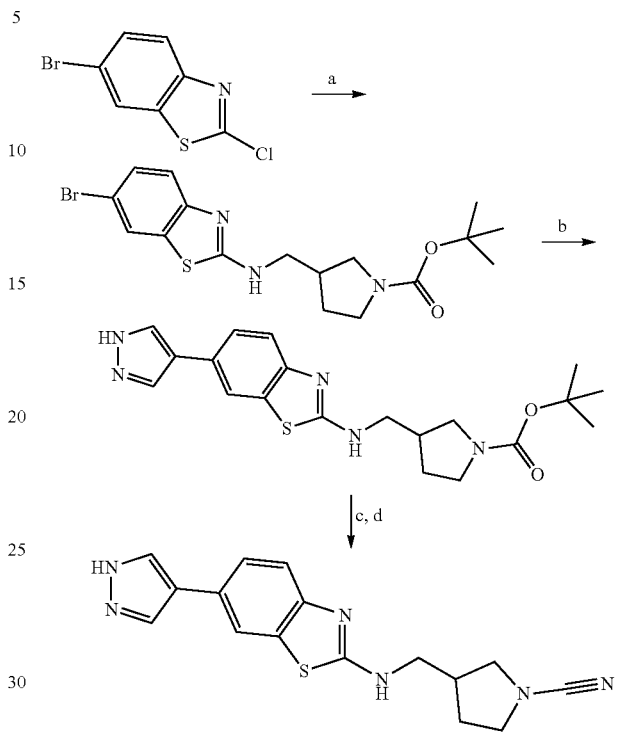

Step a. To a solution of 6-bromo-2-chloro-1,3-benzothiazole (0.1 g, 0.40 mmol) and tert-butyl 3-(aminomethyl)pyrrolidine-1-carboxylate (0.08 g, 0.40 mmol) in THF (2.5 ml) was added TEA (0.11 ml, 0.80 mmol) at rt. The reaction mixture was heated at 90° C. for 16 h, before cooling to rt and concentrating under reduced pressure. The residue was purified by column chromatography (40-50% EtOAc in hexane) yielding tert-butyl 3-(((6-bromobenzo[d]thiazol-2-yl)amino)methyl)pyrrolidine-1-carboxylate (0.105 g, 0.25 mmol). LCMS: Method C, 2.66 min, MS: ES+ 412.30.

Step b. A solution of tert-butyl 3-(((6-bromobenzo[d]thiazol-2-yl)amino)methyl)pyrrolidine-1-carboxylate (0.25 g, 0.60 mmol) and 4-(4,4,5,5-tetramethyl-1,3,2-dioxaborolan-2-yl)-1H-pyrazole (0.12 g, 0.60 mmol) in DMF:water (9:1, 5 ml) was prepared in a microwaveable glass vial and treated with NaHCO₃ (0.105 g, 1.21 mmol). The reaction mixture was degassed for 10 min at rt before addition of Pd(dppf)Cl₂ (0.022 g, 0.03 mmol). The reaction mixture was subjected to microwave heating at 140° C. for 1.5 h. The resulting mixture was poured into water (100 ml) and extracted with EtOAc (3×30 ml). The combined organic phase was washed with brine solution (2×25 ml), dried over Na₂SO₄, filtered and concentrated under reduced pressure. The residue was purified by column chromatography (7-8% MeOH in DCM) yielding tert-butyl 3-(((6-(1H-pyrazol-4-yl)benzo[d]thiazol-2-yl)amino)-methyl)pyrrolidine-1-carboxylate (0.12 g, 0.30 mmol). LCMS: Method C, 1.98 min, MS: ES+ 400.30.

Step c. To a solution of tert-butyl 3-(((6-(1H-pyrazol-4-yl)benzo[d]thiazol-2-yl)amino)methyl) pyrrolidine-1-carboxylate (0.12 g, 0.30 mmol) in DCM (3 ml) was added TFA (1.2 ml) at 0° C. The reaction mixture was stirred at rt for 1 h. The resulting reaction mixture was concentrated under reduced pressure yielding 6-(1H-pyrazol-4-yl)-N-(pyrrolidin-3-ylmethyl)benzo[d]thiazol-2-amine TFA salt (0.10 g, 0.24 mmol). This material was directly used for the next step without further purification. LCMS: Method C, 1.37 min, MS: ES+ 300.39.

Step d. To a solution of 6-(1H-pyrazol-4-yl)-N-(pyrrolidin-3-ylmethyl)benzo[d]thiazol-2-amine TFA salt (0.10 g, 0.24 mmol) in DMF (2.5 ml) was added K$_2$CO$_3$ (0.085 g, 0.60 mmol) at 0° C. Cyanogen bromide (0.03 g, 0.29 mmol) was added to the reaction mixture at 0° C. The reaction mixture was stirred at 10° C. for 45 min. The resulting reaction mixture was poured into ice cold water (40 ml) and extracted with EtOAc (3×20 ml). The combined organic phase was washed with brine solution (20 ml), dried over Na$_2$SO$_4$, filtered and concentrated under reduced pressure. The resulting residue was purified by column chromatography (3-6% MeOH in DCM) yielding the title compound (0.03 g, 0.09 mmol). LCMS: Method A, 3.21 min, MS: ES+ 324.96; $^1$H NMR (400 MHz, DMSO-d$_6$) δ ppm 12.86 (s, 1H), 8.11-8.13 (m, 2H), 7.88-7.92 (m, 2H), 7.47 (dd, J=8.40, 1.60 Hz, 1H), 7.35 (d, J=8.40 Hz, 1H), 3.43-3.51 (m, 2H), 3.33-3.40 (m, 3H), 3.15-3.19 (m, 1H), 2.55-2.62 (m, 1H), 1.98-2.03 (m, 1H), 1.67-1.72 (m, 1H).

Example 12 (R)-3-(((7-(1H-Pyrazol-4-yl)quinazolin-2-yl)amino)methyl)pyrrolidine-1-carbonitrile (1.44 ml, 10.50 mmol) was added drop wise to the reaction mixture at rt. The reaction mixture was heated at 80° C. for 4 h. The resulting reaction mixture was poured into water (100 ml) and extracted with EtOAc (3×30 ml). The combined organic phase was collected, filtered through celite hyflow. The obtained filtrate was dried over Na$_2$SO$_4$, filtered and concentrated under reduced pressure. The resulting residue was purified by column chromatography (15% EtOAc in hexane) yielding 7-bromo-2-iodoquinazoline (0.34 g, 1.01 mmol). LCMS: Method C, 2.25 min, MS: ES+ 335.20; H NMR (400 MHz, DMSO-d$_6$) δ ppm 9.38 (s, 1H), 8.24 (d, J=2 Hz, 1H), 8.13 (d, J=8.8 Hz, 1H), 7.96 (dd, J=8.8, 2 Hz, 1H).

Step c. A solution of 7-bromo-2-iodoquinazoline (0.33 g, 0.98 mmol) and tert-butyl (R)-3-(aminomethyl) pyrrolidine-1-carboxylate (0.198 g, 0.98 mmol) in NMP (10 ml) was prepared in a microwaveable glass vial. DIPEA (0.34 ml, 1.96 mmol) was added to the reaction mixture at rt. The glass vial was sealed and subjected to microwave irradiation at 70° C. for 30 min. The resulting reaction mixture was poured into brine solution (100 ml) and extracted with EtOAc (3×20 ml). The combined organic phase was collected, dried over Na$_2$SO$_4$, filtered and concentrated under reduced pressure. The resulting residue was purified by column chromatogra-

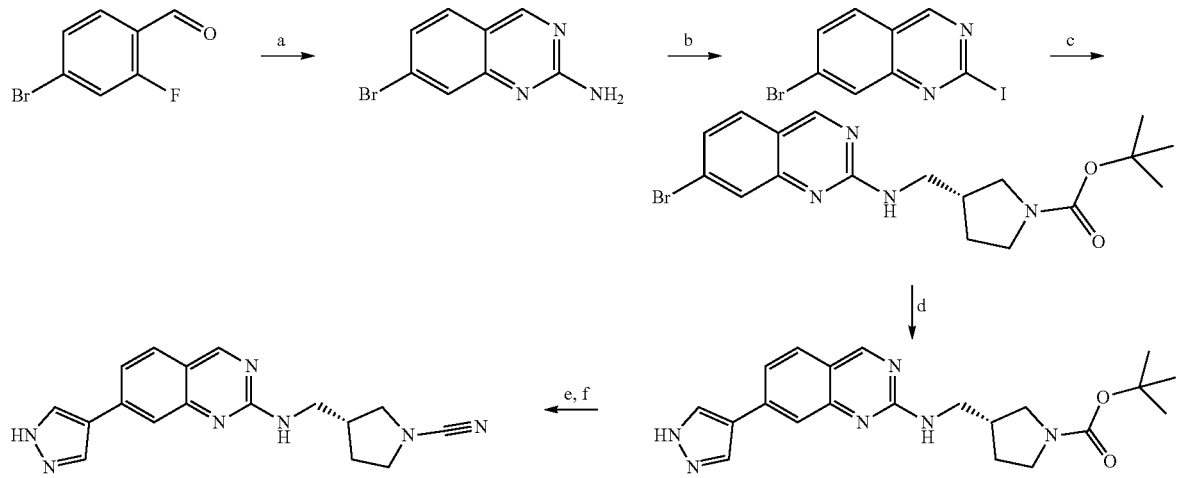

Step a. To a solution of 2-fluoro-4-bromobenzaldehyde (5.0 g, 24.63 mmol) in DMA (50 ml) was added guanidine carbonate (6.65 g, 36.94 mmol) at rt. The reaction mixture was heated at 140° C. for 2 h. The resulting reaction mixture was poured into ice cold water (500 ml). The resultant white precipitate was collected by filtration and then suspended in 2 M HCl (150 ml). The suspension was stirred well to obtain a hazy suspension, before filtering to remove un-dissolved solids. The clear filtrate was collected and washed with diethyl ether (3×50 ml). The obtained aqueous layer was basified using 2 M NaOH solution (100 ml). The obtained white precipitates were collected by filtration, washed with pentane (3×10 ml) and dried under vacuum yielding 7-bromoquinazolin-2-amine (0.80 g, 3.57 mmol). LCMS: Method C, 1.62 min, MS: ES+ 224.11; $^1$H NMR (400 MHz, DMSO-d$_6$) δ ppm 9.13 (s, 1H), 7.75 (d, J=8.4 Hz, 1H), 7.59 (d, J=2.0 Hz, 1H), 7.36 (dd, J=8.4, 2.0 Hz, 1H), 7.08 (s, 2H).

Step b. To a solution of 7-bromoquinazolin-2-amine (0.80 g, 3.57 mmol) in THF (15 ml) was added CuI (0.34 g, 1.70 mmol) and CH$_2$I$_2$ (0.94 g, 3.50 mmol) at rt. Isoamyl nitrite phy (30% EtOAc in hexane) yielding tert-butyl (R)-3-(((7-bromoquinazolin-2-yl)amino)methyl)pyrrolidine-1-carboxylate (0.80 g, quantitative). LCMS: Method C, 2.59 min, MS: ES+ 407.50.

Step d. A solution of tert-butyl (R)-3-(((7-bromoquinazolin-2-yl)amino)methyl)pyrrolidine-1-carboxylate (0.75 g, 1.84 mmol) and 4-(4,4,5,5-tetramethyl-1,3,2-dioxaborolan-2-yl)-1H-pyrazole (0.39 g, 2.00 mmol) in DMF:water (4:1, 10 ml) was prepared in a microwaveable glass vial. NaHCO$_3$ (0.30 g, 3.60 mmol) was added to the reaction mixture at rt. The mixture was degassed for 10 min at rt before addition of Pd(dppf)Cl$_2$ (0.065 g, 0.09 mmol). The reaction mixture was subjected to microwave heating at 150° C. for 30 min. The resulting reaction mixture was poured into brine solution (100 ml) and extracted with EtOAc (3×20 ml). The combined organic phase was dried over Na$_2$SO$_4$, filtered and concentrated under reduced pressure. The resulting residue was purified by column chromatography (4% MeOH in DCM) yielding tert-butyl (R)-3-(((7-(1H-pyrazol-4-yl)quinazolin-2-yl)amino)methyl)pyrrolidine-1-carboxylate (0.205 g, 0.52 mmol). LCMS: Method C, 1.80 min, MS: ES+ 395.65; ¹H NMR (400 MHz, DMSO-d₆) δ ppm 13.10 (s, 1H), 9.00 (s, 1H), 8.44 (s, 1H), 8.12 (s, 1H), 7.75 (d, J=8.40 Hz, 1H), 7.70 (s, 1H), 7.53 (dd, J=8.40, 1.60 Hz, 2H), 3.34-3.39 (m, 3H), 3.16-3.24 (m, 1H), 3.03-3.07 (m, 1H), 2.51-2.62 (m, 2H), 1.94-1.97 (m, 1H), 1.61-1.66 (m, 1H), 1.39 (s, 9H).

Steps e, f. The title compound was synthesised following the procedure in Example 9, steps c, d. LCMS: Method A, 3.23 min, MS: ES+ 320.04; ¹H NMR (400 MHz, DMSO-d₆) δ ppm 13.10 (s, 1H), 9.09 (s, 1H), 8.44 (s, 1H), 8.12 (s, 1H), 7.76 (d, J=8.40 Hz, 1H), 7.70 (s, 1H), 7.54 (dd, J=8.00, 1.20 Hz, 2H), 3.44-3.50 (m, 2H), 3.36-3.40 (m, 3H), 3.20-3.24 (m, 1H), 2.61-2.67 (m, 1H), 1.95-2.02 (m, 1H), 1.70-1.76 (m, 1H).

Example 13 Tert-butyl 3-(((3-(1,3-dimethyl-1H-pyrazol-4-yl) phenyl) amino) methyl) pyrrolidine-1-carboxylate

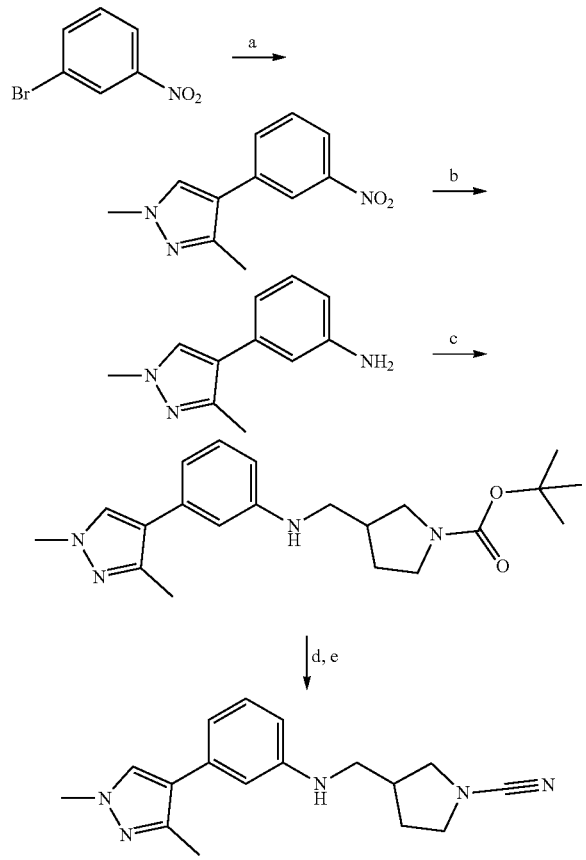

Step a. To a solution of 1-bromo-3-nitrobenzene (0.25 g, 1.23 mmol) and 1,3-dimethyl-4-(4,4,5,5-tetramethyl-1,3,2-dioxaborolan-2-yl)-1H-pyrazole (0.33 g, 1.48 mmol) in DMF:water (1:1; 4 ml) was added NaHCO₃ (0.319 g, 3.70 mmol) at rt. The mixture was degassed for 15 min before addition of PdCl₂(dppf) (0.09 g, 0.12 mmol). The reaction mixture was heated at 100° C. for 2 h. The resulting mixture was poured into water (150 ml) and extracted with EtOAc (3×100 ml). The organic phase was collected, dried over Na₂SO₄, filtered and concentrated under reduced pressure to yielding 1,3-dimethyl-4-(3-nitrophenyl)-1H-pyrazole (0.28 g, 1.28 mmol). LCMS: Method C, 2.12 min, MS: ES+218.53. The crude material was used for next step without purification.

Step b. To a solution of 1,3-dimethyl-4-(3-nitrophenyl)-1H-pyrazole (0.28 g, 1.28 mmol) in methanol:THF (1:1; 6 ml) was added 20% Pd(OH)₂ (50% moisture, 0.3 g) at rt. The reaction mixture was purged with H₂ gas at rt for 2 h. The resulting reaction mixture was carefully filtered through celite hyflow and concentrated under reduced pressure to yielding 3-(1,3-dimethyl-1H-pyrazol-4-yl)aniline (0.2 g, 1.06 mmol). LCMS: Method C, 1.52 min, MS: ES+ 188.39. The crude material was used for next step without purification.

Step c. To a solution of 3-(1,3-dimethyl-1H-pyrazol-4-yl) aniline (0.2 g, 1.06 mmol) and tert-butyl 3-formylpyrrolidine-1-carboxylate (0.27 g, 1.39 mmol) in DCM (5 ml) was added TEA (0.13 g, 1.28 mmol) at rt. The reaction mixture was stirred at 70° C. for 16 hrs. Sodium triacetoxyborohydride (0.45 g, 2.12 mmol) was added to the reaction mixture at 0° C. and stirred at rt for 16 h. The resulting reaction mixture was poured into water (100 ml) and extracted with DCM (3×100 ml). The combined organic layer was washed with saturated solution of NaHCO₃ (100 ml), dried over Na₂SO₄, filtered and concentrated under reduced pressure to yielding tert-butyl 3-(((3-(1,3-dimethyl-1H-pyrazol-4-yl) phenyl)amino)methyl)pyrrolidine-1-carboxylate (0.3 g, 0.8 mmol). LCMS: Method C, 2.38 min, MS: ES+ 371.53

Steps d, e. The title compound was synthesised following the procedure in Example 9, steps c, d. LCMS: Method B, 3.65 min, MS: ES+ 296.38; ¹H NMR (400 MHz, DMSO-d₆) δ ppm 7.77 (s, 1H), 7.06 (t, J=7.6 Hz, 1H), 6.57-6.60 (m, 2H), 6.44 (dd, J=1.6, 8.4 Hz, 1H), 5.76 (t, J=11.2 Hz, 1H), 3.76 (s, 3H), 3.34-3.52 (m, 4H), 3.13-3.17 (m, 1H), 3.03 (t, J=12.8 Hz, 2H), 2.26 (s, 3H), 1.99-2.04 (m, 1H), 1.65-1.70 (m, 1H).

Compounds in Table 2 were synthesised using a procedure similar to that described for Example 12.

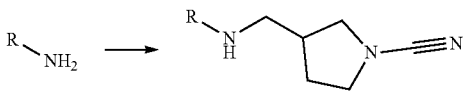

TABLE 2

| Ex | R | Name | ¹H NMR: (400 MHz, DMSO-d₆) δ ppm | LCMS Method | LCMS RT (min) | MS (ES+) |
|---|---|---|---|---|---|---|
| 14 | ![pyrazole] | 3-(((4-(1,3-Dimethyl-1H-pyrazol-4-yl) phenyl)amino)methyl) pyrrolidine-1-carbonitrile | 7.64 (s, 1 H), 7.11 (d, J = 8 Hz, 2 H), 6.59 (d, J = 8 Hz, 2 H), 5.73 (bs, 1 H), 3.73 (s, 3 H), 3.44-3.56 (m, 3 H), 3.33-3.39 (m, 1 H), 3.14 (t, J = 9.2 Hz, 1 H), 3.02 (t, J = 6 Hz, 2 H), 2.21 (s, 3 H), 1.98-2.04 (m, 1H), 1.62-1.71 (m, 1H) | B | 3.45 | 296.47 |

TABLE 2-continued

| Ex | R | Name | $^1$H NMR: (400 MHz, DMSO-d$_6$) δ ppm | LCMS Method | LCMS RT (min) | MS (ES+) |
|---|---|---|---|---|---|---|
| 15 | (3-methyl-1-methyl-1H-pyrazol-4-yl, 2-fluorophenyl group) | 3-(((4-(1,3-Dimethyl-1H-pyrazol-4-yl)-2-fluorophenyl)amino) methyl)pyrrolidine-1-carbonitrile | 7.74 (s, 1 H), 7.06 (dd, J = 2, 13.6 Hz, 1 H), 7.04 (dd, J = 1.6, 8.4 Hz, 1 H), 6.76 (t, J = 8.8 Hz, 1 H), 5.63 (bs, 1 H), 3.77 (s, 3 H), 3.42-3.49 (m, 2 H), 3.36-3.39 (m, 1 H), 3.15-3.18 (m, 1 H), 3.09 (t, 5.2 Hz, 2 H), 2.53-2.57 (m, 1 H), 2.24 (s, 3 H) 1.96-2.01 (m, 1 H), 1.63-1.70 (m, 1 H) | B | 3.81 | 314.20 |
| 16 | (6-cyanoisoquinolin-3-yl) | 3-(((1-Cyano-pyrrolidin-3-yl) methyl)amino) isoquinoline-6-carbonitrile | 9.00 (s, 1 H), 8.18 (s, 1 H), 7.97 (d, J = 8.40 Hz, 1 H), 7.35 (d, J = 8.40 Hz, 1 H), 7.05 (t, J = 5.60, 1 H), 6.71 (s, 1 H), 3.43-3.51 (m, 2 H), 3.37-3.39 (m, 1 H), 3.26-3.30 (m, 2 H), 3.16-3.20 (m, 1 H), 2.54-2.59 (m, 1 H), 1.97-2.03 (m, 1 H), 1.67-1.74 (m, 1 H). | A | 3.97 | 278 |
| 17 | (N-methylcarboxamide isoquinolinyl) | 3-(((1-Cyano-pyrrolidin-3-yl) methyl)amino)-N-methylisoquinoline-6-carboxamide | 8.91 (s, 1 H), 8.56 (d, J = 4.40 Hz, 1 H), 8.01 (s, 1 H), 7.85 (d, J = 8.40 Hz, 1 H), 7.51 (dd, J = 8.40, 1.20 Hz, 1 H), 6.82 (t, J = 5.60, 1 H), 6.96 (s, 1 H), 3.44-3.52 (m, 2 H), 3.36-3.40 (m, 1 H), 3.27-3.30 (m, 2 H), 3.17-3.21 (m, 1 H), 2.81 (d, J = 4.40 Hz, 3 H), 2.55-2.59 (m, 1 H), 1.97-2.03 (m, 1 H), 1.67-1.75 (m, 1 H). | A | 3.10 | 310.19 |

Example 18 Tert-butyl 3-(((3-(1,3-dimethyl-1H-pyrazol-4-yl) phenyl) amino) methyl) pyrrolidine-1-carboxylate

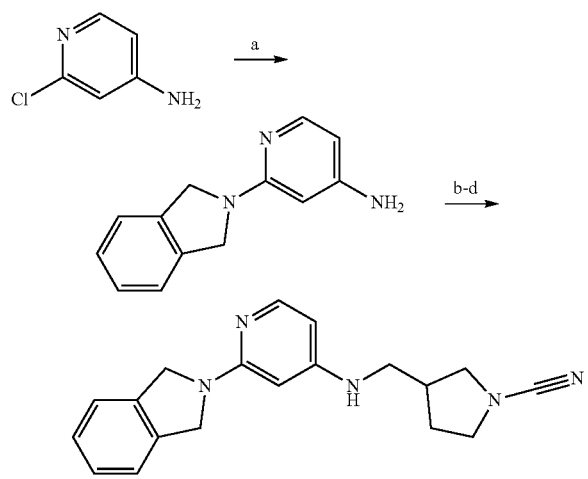

Step a. To a solution of 2-chloropyridin-4-amine (0.5 g, 3.90 mmol) in toluene (12 ml) were added isoindoline hydrochloride (0.91 g, 5.85 mmol), BINAP (0.24 g, 0.39 mmol) and potassium tert-butoxide (2.07 g, 9.76 mmol) at rt. The mixture was degassed for 10 min before addition of Pd$_2$(dba)$_3$ (0.178 g, 0.19 mmol). The reaction mixture was at 110° C. for 4 hrs. The resulting mixture was poured into cold water (200 ml) and combined with two other batches prepared by an identical method on the same scale. The resulting mixture was extracted with DCM (3×100 ml). The organic phase was collected, dried over Na$_2$SO$_4$, filtered and concentrated under reduced pressure. The resulting residue was purified by column chromatography (3% MeOH in DCM) yielding 2-(isoindolin-2-yl)pyridin-4-amine (1.2 g, 5.67 mmol). LCMS: Method C, 1.57 min, MS: ES+ 212.29.

Steps b-d. The title compound was synthesised following the procedure in Example 12, steps c-e. LCMS: Method A, 4.22 min, MS: ES+ 320.10; $^1$H NMR (400 MHz, DMSO-d$_6$) δ ppm 7.67 (d, J=6 Hz, 1H), 7.38-7.40 (m, 2H), 7.29-7.32 (m, 2H), 6.37 (t, J=5.2 Hz, 1H), 5.98 (dd, J=1.6, 5.6 Hz, 1H), 5.62 (d, J=1.6 Hz, 1H), 4.66 (s, 4H), 3.44-3.52 (m, 2H), 3.34-3.40 (m, 2H), 3.08-3.16 (m, 3H), 1.98-2.06 (m, 1H), 1.65-1.70 (m, 1H).

Example 19 (S)-3-(((4-Phenylpyrimidin-2-yl)amino) methyl)pyrrolidine-1-carbonitrile

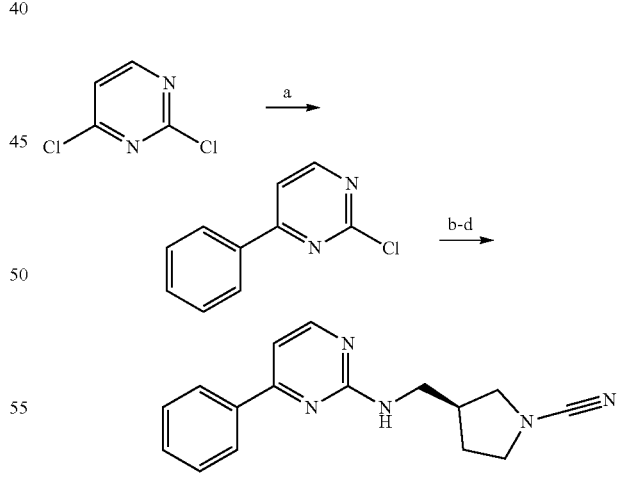

Step a. A solution of 2,4-dichloropyrimidine (1.00 g, 6.71 mmol), phenylboronic acid (0.90 g, 7.38 mmol) in 1,4-dioxane:water (8:2; 15 ml) was stirred at rt. The reaction mixture was degassed for 15 min before addition of Cs$_2$CO$_3$ (6.56 g, 20.13 mmol) and Pd(PPh$_3$)$_4$ (0.39 g, 0.335 mmol). The reaction mixture was heated at 110° C. for 14 h. The resulting reaction mixture was cooled to rt and poured into saturated NaHCO$_3$ solution (40 ml). The obtained mixture was extracted with EtOAc (2×25 ml). The combined organic phase was washed with brine solution (20 ml), dried over Na$_2$SO$_4$, filtered and concentrated under reduced pressure. The resulting residue was purified by flash chromatography (8% EtOAc in hexane) yielding 2-chloro-4-phenylpyrimidine (0.45 g, 2.37 mmol). LCMS: Method C, 2.23 min, MS: ES+ 191.57; H NMR (400 MHz, CDCl$_3$) δ ppm 8.67 (d, J=5.2 Hz, 1H), 8.11-8.13 (m, 2H), 7.68 (d, J=5.6 Hz, 1H), 7.54-7.58 (m, 3H).

Steps b-d. The title compound was synthesised following the procedure in Example 9, steps b-d, using tert-butyl (S)-3-(aminomethyl)pyrrolidine-1-carboxylate. LCMS: Method A, 4.20 min, MS: ES+ 280.13; H NMR (400 MHz, DMSO-d$_6$) δ ppm 8.35-8.36 (m, 1H), 8.02-8.17 (m, 2H), 7.40-7.54 (m, 3H), 7.15-7.16 (d, J=4.8 Hz, 1H), 3.30-3.49 (m, 6H), 3.18-3.21 (m, 1H), 1.95-2.00 (m, 1H), 1.68-1.72 (m, 1H).

Example 20 N-((1-Cyanopyrrolidin-3-yl)methyl)-2-phenyloxazole-5-carboxamide

Step a. To a solution of 2-phenyloxazole-5-carboxylic (0.20 g, 1.06 mmol) in THF (5 ml) was added DIPEA (0.41 g, 3.17 mmol) and T3P (50% in EtOAc; 1.00 g, 1.58 mmol) at rt and stirred for 30 min. The reaction mixture was treated with tert-butyl 3-(aminomethyl)pyrrolidine-1-carboxylate (0.26 g, 1.32 mmol) and stirred at rt for 3 h. The resulting reaction mixture was poured into saturated NaHCO$_3$ solution (20 ml) and extracted with EtOAc (2×10 ml). The combined organic phase was collected and washed with 10% citric acid solution (5 ml), dried over Na$_2$SO$_4$, filtered and concentrated under reduced pressure yielding tert-butyl 3-((2-phenyloxazole-5-carboxamido)methyl)pyrrolidine-1-carboxylate (0.25 g, 0.67 mmol). LCMS: Method C, 2.14 min, MS: ES+ 372.33.

Step b, c. The title compound was synthesised following the procedure in Example 9, steps c, d and purified by flash chromatography (60% EtOAc in hexane) yielding the title compound (0.050 g, 0.168 mmol). LCMS: Method B, 3.33 min, MS: ES+ 297.18; $^1$H NMR (400 MHz, DMSO-d$_6$) δ ppm 8.86 (t, J=5.6 Hz, 1H), 8.12-8.14 (m, 2H), 7.87 (d J=0.8 Hz, 1H), 7.58-7.61 (m, 3H), 3.25-3.48 (m, 6H), 3.16-3.20 (m, 2H), 1.91-2.01 (m, 1H), 1.66-1.73 (m, 1H).

Compounds in Table 3.1 were synthesised using a procedure similar to that described for Example 20.

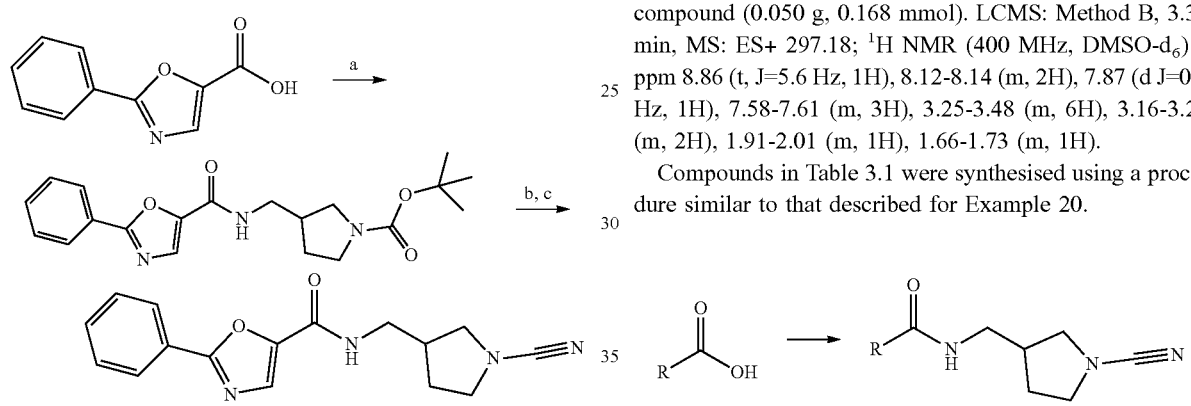

TABLE 3.1

| Ex | R | Name | LCMS Method | LCMS RT (min) | MS ES+ |
|---|---|---|---|---|---|
| 21 | | N-((1-Cyanopyrrolidin-3-yl)methyl)-3-phenylisoxazole-5-carboxamide | E | 2.59 | 297.1 |
| 22 | | N-((1-Cyanopyrrolidin-3-yl)methyl)-5-phenyl-1H-pyrazole-3-carboxamide | E | 2.29 | 296.2 |
| 23 | | N-((1-Cyanopyrrolidin-3-yl)methyl)-4-methyl-3-oxo-3,4-dihydro-2H-benzo[b][1,4]oxazine-6-carboxamide | F | 1.91 | 315.2 |

TABLE 3.1-continued

| Ex | R | Name | LCMS Method | LCMS RT (min) | MS ES+ |
|---|---|---|---|---|---|
| 24 | (pyridin-4-yl)phenyl | N-((1-Cyanopyrrolidin-3-yl)methyl)-4-(pyridin-4-yl)benzamide | F | 2.14 | 307.1 |
| 25 | 3-(o-tolyl)-1H-pyrazol-5-yl | N-((1-Cyanopyrrolidin-3-yl)methyl)-3-(o-tolyl)-1H-pyrazole-5-carboxamide | D | 3.27 | 310.2 |
| 26 | 2-phenylthiazol-4-yl | N-((1-Cyanopyrrolidin-3-yl)methyl)-2-phenylthiazole-4-carboxamide | D | 3.52 | 313.1 |
| 27 | 4-(pyrrolidin-1-yl)pyridin-2-yl | N-((1-Cyanopyrrolidin-3-yl)methyl)-4-(pyrrolidin-1-yl)picolinamide | D | 2.54 | 300.3 |
| 28 | 1-(2,4-dichlorobenzyl)-1H-indazol-3-yl | N-((1-Cyanopyrrolidin-3-yl)methyl)-1-(2,4-dichlorobenzyl)-1H-indazole-3-carboxamide | E | 2.83 | 428.1 |
| 29 | 1-benzyl-1H-indazol-3-yl | 1-Benzyl-N-((1-cyanopyrrolidin-3-yl)methyl)-1H-indazole-3-carboxamide | E | 2.52 | 360.2 |
| 30 | 4-(N-phenylsulfamoyl)phenyl | N-((1-Cyanopyrrolidin-3-yl)methyl)-4-(N-phenylsulfamoyl)benzamide | D | 3.30 | 385.2 |
| 31 | 3-(2-fluorophenyl)-1H-pyrazol-5-yl | N-((1-Cyanopyrrolidin-3-yl)methyl)-3-(2-fluorophenyl)-1H-pyrazole-5-carboxamide | E | 2.37 | 314.0 |

TABLE 3.1-continued

| Ex | R | Name | LCMS Method | LCMS RT (min) | MS ES+ |
|---|---|---|---|---|---|
| 32 | | (E)-N-((1-Cyanopyrrolidin-3-yl)methyl)-3-(2-fluoro-4-methoxyphenyl)acrylamide | E | 2.59 | 304.0 |
| 33 | | N-((1-Cyanopyrrolidin-3-yl)methyl)-5-(4-fluorophenyl)nicotinamide | D | 2.87 | 325.1 |

Example 34 (S)—N-((1-Cyanopyrrolidin-3-yl)methyl)-3-oxo-3,4-dihydro-2H-benzo[b][1,4]oxazine-6-carboxamide

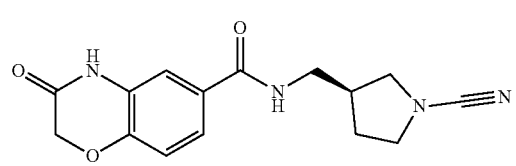 [SMILES: N#CN1CC[C@@H](CNC(=O)c2ccc3c(c2)NC(=O)CO3)C1]

The title compound was synthesised by a procedure similar to Example 20. LCMS: Method B, 2.80 min, MS: ES+ 301.27; H NMR (400 MHz, DMSO-d$_6$) δ ppm 10.85 (s, 1H), 8.52 (t, J=5.6 Hz 1H), 7.40-7.44 (m, 2H), 7.00 (d, J=8.0 Hz, 1H), 4.63 (s, 2H), 3.36-3.44 (m, 3H), 3.23-3.28 (m, 2H), 3.13-3.21 (m, 1H), 2.51-2.54 (m, 1H), 1.91-1.95 (m, 1H), 1.63-1.67 (m, 1H).

Example 35 (R)-6-Chloro-N-((1-cyanopyrrolidin-3-yl)methyl)imidazo[1,2-a]pyridine-2-carboxamide

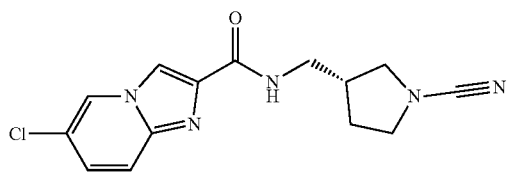 [SMILES: N#CN1CC[C@H](CNC(=O)c2cn3cc(Cl)ccc3n2)C1]

The title compound was synthesised by a procedure similar to Example 20. LCMS: Method A, 3.23 min, MS: ES+ 303.94; $^1$H NMR (400 MHz, DMSO-d$_6$) δ ppm 8.88 (m, 1H), 8.72 (t, J=6.0 Hz, 1H), 8.33 (s, 1H), 7.64 (d, J=9.6 Hz, 1H), 7.41 (dd, J=2.0 Hz, 9.6 Hz, 1H), 3.39-3.46 (m, 2H), 3.26-3.31 (m, 2H), 3.16-3.19 (m, 1H), 2.53-2.54 (m, 2H), 1.87-1.96 (m, 1H), 1.65-1.71 (m, 1H).

Example 36 (R)—N-((1-Cyanopyrrolidin-3-yl)methyl)pyrazolo[1,5-a]pyridine-2-carboxamide

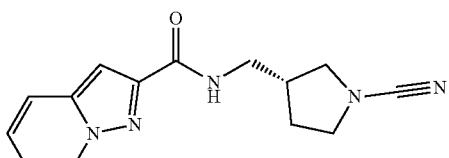

The title compound was synthesised by a procedure similar to Example 20. LCMS: Method A, 3.07 min, MS: ES+ 270.09; $^1$H NMR (400 MHz, DMSO-d$_6$) δ ppm 8.70 (t, J=6.0 Hz, 1H), 8.67 (dd, J=0.8 Hz, 6.8 Hz, 1H), 7.77 (d, J=8.8 Hz, 1H), 7.27-7.32 (m, 1H), 7.02-7.05 (m, 1H), 6.99 (s, 1H), 3.40-3.46 (m, 2H), 3.28-3.32 (m, 2H), 3.17-3.20 (m, 1H), 2.52-2.55 (m, 2H), 1.89-1.97 (m, 1H), 1.64-1.72 (m, 1H).

Example 55 (R)-3-(3-Chlorophenyl)-N-((1-cyanopyrrolidin-3-yl)methyl)isoxazole-5-carboxamide

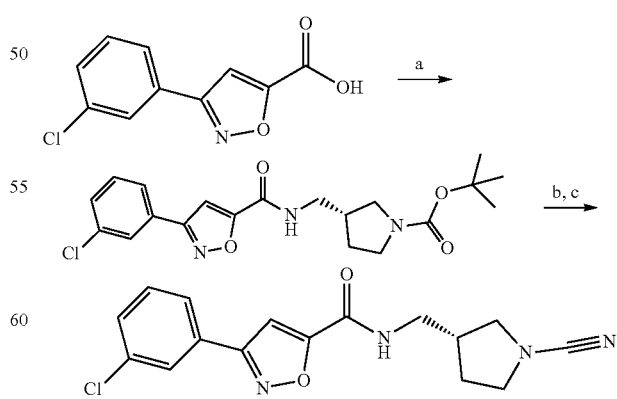

Step a. To a stirred solution of 3-(3-chlorophenyl)isoxazole-5-carboxylic acid (CAS Number 100517-43-9; 0.200 g, 0.894 mmol) and tert-butyl (R)-3-(aminomethyl)pyrrolidine-1-carboxylate (CAS Number 199174-29-3; 0.179 g, 0.894 mmol) in THF (2 ml) was added HATU (0.510 g, 1.34 mmol) and DIPEA (0.45 ml, 2.68 mmol) at rt. The reaction mixture was stirred at rt for 16 h. The resulting reaction mixture was diluted with water (50 ml) and extracted with EtOAc (2×50 ml). The combined organic layer was dried over Na₂SO₄, filtered and concentrated under reduced pressure. The residue was purified by flash column chromatography (35% EtOAc in hexane) yielding tert-butyl (R)-3-((3-(3-chlorophenyl)isoxazole-5-carboxamido)methyl)pyrrolidine-1-carboxylate (0.250 g, 0.615 mmol). LCMS: Method C, 2.312 min, MS: ES+ 406.42

Steps b, c. The title compound was synthesised following the procedure described in Example 9, steps c, d. LCMS: Method A, 4.165 min, MS: ES+ 331.15; ¹H NMR (400 MHz, DMSO-d₆) δ ppm 9.21 (t, J=1.6 Hz, 1H), 8.00 (t, J=1.6 Hz, 1H), 7.90-7.93 (m, 1H), 7.73 (s, 1H), 7.56-7.64 (m, 2H), 3.39-3.46 (m, 2H), 3.35-3.38 (m, 1H), 3.30-3.33 (m, 3H), 3.15-3.28 (m, 1H), 1.85-2.01 (m, 1H), 1.62-1.71 (m, 1H).

Compounds in Table 3.2 were synthesised using a procedure similar to that described for Example 55.

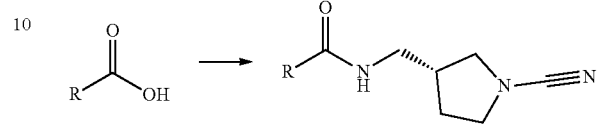

TABLE 3.2

| Ex | R | Name | ¹H NMR (400 MHz) δ ppm | LCMS Method | LCMS RT (min) | MS (ES+) |
|---|---|---|---|---|---|---|
| 56 | benzimidazol-2-yl | (R)-N-((1-Cyano-pyrrolidin-3-yl)methyl)-1H-benzo[d]imidazole-2-carboxamide | (CDCl₃) 10.73 (s, 1 H), 7.80-7.82 (m, 2 H), 7.55-7.57 (m, 1 H), 7.36-7.44 (m, 2 H), 3.50-3.63 (m, 4 H), 3.44-3.48 (m, 1 H), 3.26-3.30 (m, 1 H), 2.62-2.69 (m, 1 H), 2.12-2.16 (m, 1 H), 1.79-1.86 (m, 1 H). | A | 2.921 | 270.11 |
| 57 | isoquinolin-3-yl | (R)-N-((1-Cyano-pyrrolidin-3-yl)methyl)isoquinoline-3-carboxamide | (DMSO-d₆) 9.39 (s, 1 H), 9.20 (t, J = 2.4 Hz, 1 H), 8.57 (s, 1 H), 8.26 (d, J = 8.0 Hz, 1 H), 8.20 (d, J = 8.0 Hz, 1 H), 7.86-7.90 (m, 1 H), 7.79-7.83 (m, 1 H), 3.41-3.48 (m, 2 H), 3.35-3.39 (m, 3 H), 3.20-3.23 (m, 1 H), 2.54-2.61 (m, 1 H), 1.90-1.98 (m, 1 H), 1.68-1.75 (m, 1 H) | A | 3.686 | 281.02 |
| 58 | 5-phenylisoxazol-3-yl | (R)-N-((1-Cyano-pyrrolidin-3-yl)methyl)-5-phenyl-isoxazole-3-carboxamide | (CDCl₃) 7.81-7.83 (m, 2 H), 7.51-7.52 (m, 3 H), 7.05 (br s, 1 H), 6.98 (s, 1 H), 3.44-3.62 (m, 5 H), 3.22-3.26 (m, 1 H), 2.60-2.67 (m, 1 H), 2.08-2.14 (m, 1 H), 1.74-1.81 (m, 1 H). | A | 4.061 | 297.04 |
| 59 | 4-phenylpyridin-2-yl | (R)-N-((1-Cyano-pyrrolidin-3-yl)methyl)-4-phenyl-picolinamide | (DMSO-d₆) 9.12 (t, J = 2.0 Hz, 1 H), 8.71 (d, J = 5.2 Hz, 1 H), 8.29 (s, 1 H), 7.93-7.94 (m, 1 H), 7.85-7.87 (m, 2 H), 7.51-7.58 (m, 3 H), 3.39-3.47 (m, 4 H), 3.29-3.33 (m, 1 H), 3.17-3.21 (m, 1 H), 2.55-2.58 (m, 1 H), 1.91-1.96 (m, 1H), 1.66-1.71 (m, 1 H). | A | 4.056 | 307.01 |
| 60 | 5-phenylpyridin-2-yl | (R)-N-((1-Cyano-pyrrolidin-3-yl)methyl)-5-phenyl-picolinamide | (DMSO-d₆) 9.10 (t, J = 2.4 Hz, 1 H), 8.95 (d, J = 1.6 Hz, 1 H), 8.28 (dd, J = 8.0, 2.0 Hz, 1 H), 8.11 (d, J = 8.0 Hz, 1 H), 7.80-7.82 (m, 2 H), 7.53-7.57 (m, 2 H), 7.46-7.50 (m, 1 H), 3.40-3.47 (m, 4 H), 3.34-3.38 (m, 1 H), 3.17-3.21 (m, 1 H), 2.55-2.58 (m, 1 H), 1.89-1.97 (m, 1 H), 1.64-1.73 (m, 1 H). | A | 4.099 | 307.08 |
| 61 | 5-phenylthiazol-2-yl | (R)-N-((1-Cyano-pyrrolidin-3-yl)methyl)-5-phenyl-thiazole-2-carboxamide | (DMSO-d₆) 9.03 (t, J = 5.6 Hz, 1 H), 8.40 (s, 1 H), 7.74-7.76 (m, 2 H), 7.38-7.48 (m, 3 H), 3.38-3.42 (m, 2 H), 3.25-3.33 (m, 2 H), 3.13-3.17 (m, 1 H), 2.51-2.53 (m, 2 H), 1.87-1.95 (m, 1 H), 1.61-1.69 (m, 1 H) | A | 3.993 | 313.05 |
| 62 | 4-phenylthiazol-2-yl | (R)-N-((1-Cyano-pyrrolidin-3-yl)methyl)-4-phenyl-thiazole-2-carboxamide | (DMSO-d₆) 9.09 (t, J = 6.0 Hz, 1 H), 8.42 (s, 1 H), 8.08-8.10 (m, 2 H), 7.47-7.51 (m, 2 H), 7.38-7.42 (m, 2 H), 3.37-3.43 (m, 2 H), 3.32-3.36 (m, 2 H), 3.19-3.23 (m, 1 H), 2.53-2.59 (m, 2 H), 1.92-2.00 (m, 1 H), 1.66-1.75 (m, 1H) | A | 4.402 | 313.10 |

TABLE 3.2-continued

| Ex | R | Name | $^1$H NMR (400 MHz) δ ppm | LCMS Method | LCMS RT (min) | MS (ES+) |
|---|---|---|---|---|---|---|
| 63 | | (R)-N-((1-Cyano-pyrrolidin-3-yl)methyl)-1-phenyl-1H-pyrazole-3-carboxamide | (DMSO-$d_6$) 8.55-8.58 (m, 2 H), 7.93-7.95 (m, 2 H), 7.53-7.57 (m, 2 H), 7.36-7.40 (m, 1 H), 6.90 (d, J = 2.4 Hz, 1 H), 3.37-3.47 (m, 2 H), 3.24-3.31 (m, 2 H), 3.17-3.21 (m, 1 H), 2.51-2.53 (m, 2 H), 1.90-1.96 (m, 1 H), 1.66-1.71 (m, 1 H) | A | 3.155 | 296.15 |
| 64 | | (R)-N-((1-Cyano-pyrrolidin-3-yl)methyl)-2-phenyl-1H-imidazole-5-carboxamide | (DMSO-$d_6$) 12.97-13.04 (m, 1 H), 8.18-8.21 (m, 1 H), 7.95-8.01 (m, 2 H), 7.76 (s, 1 H), 7.41-7.50 (m, 3 H), 3.41-3.47 (m, 2 H), 3.25-3.31 (m, 2 H), 3.16-3.20 (m, 1 H), 2.51-2.53 (m, 2 H), 1.88-1.97 (m, 1 H), 1.64-1.72 (m, 1 H) | A | 2.711 | 295.95 |
| 65 | | (R)-7-Chloro-N-((1-cyano-pyrrolidin-3-yl)methyl) imidazo[1,2-a] pyridine-2-carboxamide | (DMSO-$d_6$) 8.68 (s, 1 H), 8.61 (d, J = 6.4 Hz, 1 H), 8.38 (s, 1 H), 7.73 (s, 1 H), 7.08 (d, J = 6.4 Hz, 1 H), 3.35-3.42 (m, 2 H), 3.27-3.33 (m, 3 H), 3.14-3.16 (m, 1 H), 2.89-2.92 (m, 1 H), 1.90-1.93 (m, 1 H), 1.64-1.70 (m, 1 H) | A | 3.352 | 304.02 |

Example 37 2-([1,1'-Biphenyl]-4-yl)-N-methyl-N-(pyrrolidin-3-ylmethyl)acetamide

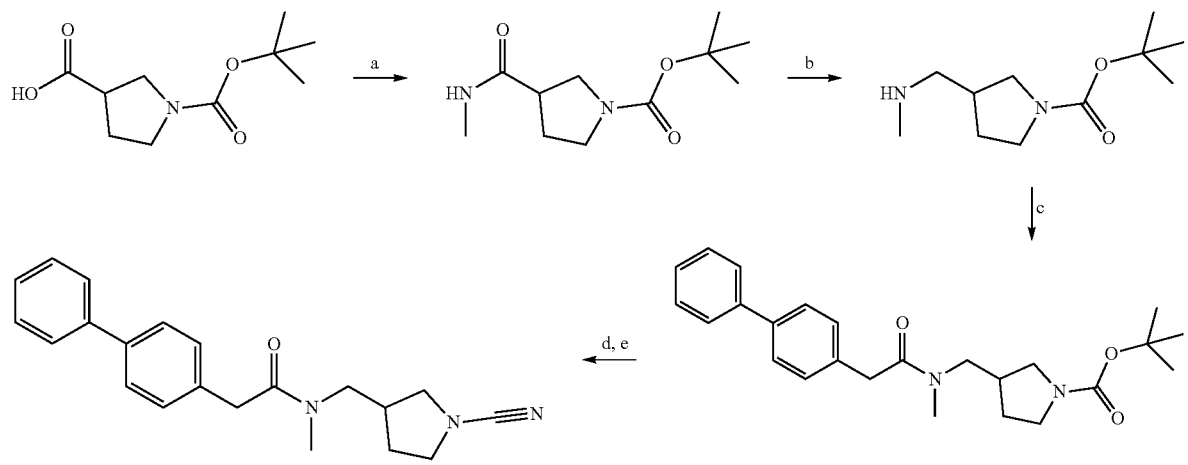

Step a. To a solution of 1-tert-butoxycarbonylpyrrolidine-3-carboxylic acid (70 mmol) in DCM (200 ml) was added CDI (140 mmol). The reaction mixture was stirred at 0° C. for 20 min. Methylamine hydrochloride (84.5 mmol) and DIPEA (210 mmol) were added to the reaction mixture at rt. The reaction mixture was stirred at rt for 12 h. The resulting mixture was poured into saturated NaHCO$_3$ solution (120 ml) and extracted with EtOAc (2×150 mL). The organic layer was washed with 1 M HCl (40 ml), dried over Na$_2$SO$_4$, filtered and concentrated under reduced pressure. The resulting mixture was purified by column chromatography (SiO$_2$, PE:EtOAc 50:1 to 5:1) yielding tert-butyl 3-(methylcarbamoyl)pyrrolidine-1-carboxylate (33.0 mmol). $^1$H NMR (400 MHz, DMSO-$d_6$) δ 7.85 (s, 1H), 3.30-3.45 (m, 3H), 3.11-3.49 (m, 2H), 2.78-2.93 (m, 1H), 2.56 (s, 3H), 1.78-1.99 (m, 2H), 1.37 (s, 9H).

Step b. To a solution of tert-butyl 3-(methylcarbamoyl) pyrrolidine-1-carboxylate (33.0 mmol) in THF (75 ml) was added BH$_3$.THF (99.0 mmol) at 0° C. The reaction was stirred at 0° C. for 3 h. The resulting mixture was quenched by addition MeOH 20 ml. The resulting mixture was concentrated under reduced pressure, and then the residue was purified by column chromatography (SiO$_2$, DCM:MeOH 100:0 to 10:1) yielding tert-butyl 3-(methylcarbamoyl)pyrrolidine-1-carboxylate (12 mmol). $^1$H NMR (400 MHz, DMSO-$d_6$) δ 3.45-3.8 (s, 2H), 3.25-3.42 (m, 2H), 3.12-3.25 (m, 1H), 2.85-2.91 (m, 1H), 2.41-2.49 (m, 2H), 2.12-2.35 (m, 3H), 1.78-1.95 (s, 1H), 1.45-1.61 (m, 2H), 1.39 (s, 9H).

Step c. To a solution of 2-([1,1'-biphenyl]-4-yl)acetic acid (0.2 mmol) in DCM (1 ml) was added HATU (0.2 mmol). The reaction mixture was stirred at 0° C. for 20 min. Tert-butyl 3-((methylamino) methyl)pyrrolidine-1-carboxylate (0.2 mmol) and DIPEA (0.6 mmol) were added to the reaction mixture at rt and stirred for 16 h. The resulting mixture was concentrated under reduced pressure. The resulting residue was purified by prep-TLC (PE:EtOAc 1:2) yielding tert-butyl 3-((2-([1,1'-biphenyl]-4-yl)-N-methylac-etamido)methyl)pyrrolidine-1-carboxylate. MS: ES+ 409.5.

Steps d, e. The title compound was synthesised from the intermediate above using a procedure similar to that described for Example 1, steps b, c to provide the title compound (46.60 mg, 0.139 mmol). LCMS: Method E, 2.90 min, MS: ES+ 334.2.

Example 38 N-((1-Cyanopyrrolidin-3-yl)methyl)-5-phenyloxazole-2-carboxamide

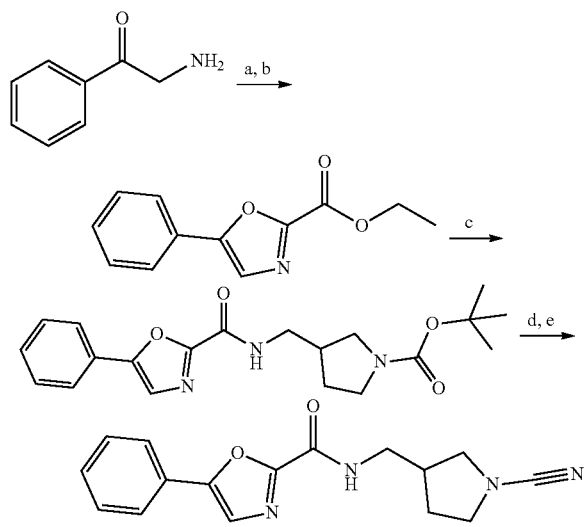

Step a. To a solution of 2-amino-1-phenylethanone hydrochloride (0.50 g, 2.91 mmol) in DCM (5 ml) was added TEA (0.58 g, 5.83 mmol) at 0° C. The reaction mixture was stirred at 0° C. for 15 min. Ethyl chlorooxoacetate (0.44 g, 3.21 mmol) was added slowly to the reaction mixture at 0° C. The reaction mixture was stirred at rt for 36 h. The resulting reaction mixture was poured into saturated NaHCO$_3$ solution (10 ml) and extracted with DCM (2×10 ml). The combined organic phase was collected and washed with brine (10 ml), dried over Na$_2$SO$_4$, filtered and concentrated under reduced pressure yielding ethyl 2-oxo-2-((2-oxo-2-phenylethyl)amino)acetate (0.58 g, 2.46 mmol). LCMS: Method C, 1.79 min, MS: ES+ 236.33.

Step b. A solution of ethyl 2-oxo-2-((2-oxo-2-phenylethyl)amino)acetate (0.58 g, 2.47 mmol) in POCl$_3$ (5 ml) was refluxed at 105° C. for 2 h. The resulting reaction mixture was concentrated under reduced pressure. The obtained residue was carefully treated with saturated Na$_2$CO$_3$ solution (20 ml) and the mixture was extracted with DCM (2×15 ml). The combined organic phase was collected and washed with brine (10 ml), dried over Na$_2$SO$_4$, filtered and concentrated under reduced pressure yielding ethyl 5-phenyloxazole-2-carboxylate (0.48 g, 2.211 mmol). LCMS: Method C, 2.09 min, MS: ES+ 218.18.

Step c. To a solution of ethyl 5-phenyloxazole-2-carboxylate (0.46 g, 2.12 mmol) in THF (5 ml) was added DIPEA (0.82 g, 6.35 mmol) at 0° C. and stirred for 15 min. Tert-butyl 3-(aminomethyl)pyrrolidine-1-carboxylate (0.53 g, 2.64 mmol) was added to the reaction mixture at 0° C. followed by slow addition of TMA (2 M in toluene; 5.29 ml, 10.6 mmol) at 0° C. The resulting reaction mixture was heated at 70° C. for 5 hr. The resulting reaction mixture was quickly poured into ice cold water (25 ml) and filtered through celite hyflow. The filtrate was extracted with EtOAc (3×15 ml). The combined organic phase was collected and washed with brine (10 ml), dried over Na$_2$SO$_4$, filtered and concentrated under reduced pressure yielding tert-butyl 3-((5-phenyloxazole-2-carboxamido)methyl)-pyrrolidine-1-carboxylate (0.25 g, 0.673 mmol). LCMS: Method C, 2.28 min, MS: ES+ 372.4.

Steps d, e. The title compound was synthesised from the intermediate above using a procedure similar to that described for Example 9, steps c, d and purified by flash chromatography (35%-40% EtOAc in hexane). The obtained sticky residue was triturated with pentane:diethyl ether (2:1; 2 ml) and dried to yield the title compound (0.013 g, 0.044 mmol). LCMS: Method B, 3.49 min, MS: ES+ 297.23; $^1$H NMR (400 MHz, DMSO-d$_6$) δ ppm 9.17 (t, 5.6 Hz, 1H), 7.92 (s, 1H), 7.83 (d, J=7.6 Hz, 2H), 7.53 (t, J=7.2 Hz, 2H), 7.43-7.47 (m, 1H), 3.41-3.46 (m, 2H), 3.34-3.38 (m, 2H), 3.27-3.30 (m, 2H), 3.16-3.20 (m, 1H), 1.91-1.99 (m, 1H), 1.65-1.70 (m, 1H).

Example 66 (R)-3-(2-Chlorophenyl)-N-((1-cyanopyrrolidin-3-yl)methyl)isoxazole-5-carboxamide

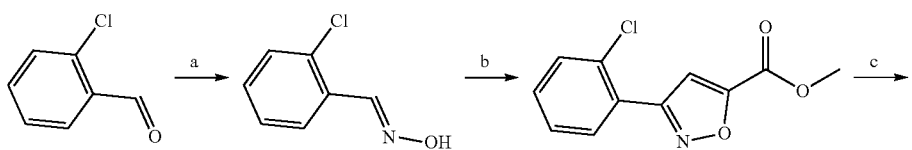

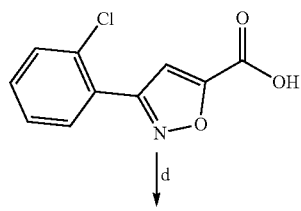

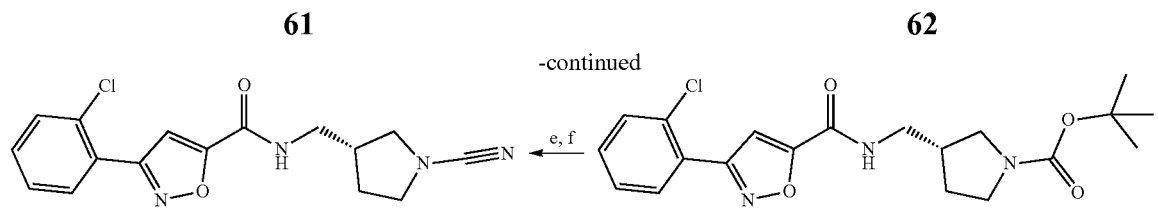

Step a. To a stirred solution of 2-chlorobenzaldehyde (1.500 g, 10.67 mmol) in MeOH (10 ml) was added TEA (3.23 g, 32.0 mmol) at rt. Hydroxylamine hydrochloride (0.889 g, 12.8 mmol) was added portion wise to the reaction mixture at rt. The reaction mixture was stirred at rt for 4 h. The resulting mixture was concentrated under reduced pressure and the obtained residue was diluted with ice cold water (50 ml). The obtained precipitates were collected by filtration and washed with chilled water (20 ml). The resulting solid material was dried under vacuum yielding 2-chlorobenzaldehyde oxime (1.250 g 8.062 mmol). This material was directly used for next step without any further purification. LCMS: Method C, 1.803 min, MS: ES+ 156.24.

Step b. To a stirred solution of methyl propiolate (1.085 g 12.90 mmol) in water (10 ml) was added KCl (0.384 g, 5.16 mmol) and 2-chlorobenzaldehyde oxime (0.800 g 5.16 mmol) at rt. The reaction mixture was stirred at rt for 30 min. Oxone (2.376 g, 7.74 mmol) was added to the reaction mixture at rt. The reaction mixture was stirred at rt for 4 h. The resulting mixture was diluted with water (25 ml) and extracted with DCM (2×25 ml). The combined organic layer was washed with brine solution (10 ml), dried over $Na_2SO_4$, filtered and concentrated under reduced pressure. The resulting residue was purified by flash column chromatography (5% EtOAc in hexane) yielding methyl 3-(2-chlorophenyl)isoxazole-5-carboxylate (0.750 g, 3.164 mmol). LCMS: Method C, 2.139 min, MS: ES-236.00.

Step c. To a stirred solution of methyl 3-(2-chlorophenyl)isoxazole-5-carboxylate (0.750 g, 3.16 mmol) in THF:water (1:1; 6 ml) was added $LiOH.H_2O$ (0.398 g, 9.49 mmol) at rt. The reaction mixture was stirred at rt for 1 h. The resulting reaction mixture concentrated under vacuum, diluted with ice cold water (10 ml) and acidified using 1 M HCl solution. The resulting precipitates were collected by filtration. The obtained solid material was dried under high vacuum yielding 3-(2-chloro-phenyl)isoxazole-5-carboxylic acid (0.420 g, 1.88 mmol). This material was directly used for next step without any further purification. LCMS: Method C, 1.475 min, MS: ES-222.21.

Step d. To a stirred solution of 3-(2-chlorophenyl)isoxazole-5-carboxylic acid (0.220 g, 0.986 mmol) and tert-butyl (R)-3-(aminomethyl)pyrrolidine-1-carboxylate (CAS Number 199174-29-3; 0.197 g, 0.986 mmol) in DCM (3 ml) was added pyridine (0.778 g, 0.986 mmol) at 0° C., followed by dropwise addition of $POCl_3$ (0.226 g, 1.48 mmol) at 0° C. The reaction mixture was stirred at 0° C. for 30 min. The resulting mixture was diluted with ice cold $NaHCO_3$ solution (30 ml) and extracted with DCM (2×20 ml). The combined organic layer was dried over $Na_2SO_4$, filtered and concentrated under reduced pressure. The resulting residue was purified by flash column chromatography (1-2% MeOH in DCM) yielding tert-butyl (R)-3-((3-(2-chlorophenyl)isoxazole-5-carboxamido)methyl)pyrrolidine-1-carboxylate (0.180 g, 0.443 mmol). LCMS: Method C, 2.179 min, MS: ES-404.43.

Steps e, f. The title compound was synthesised from the intermediate above using a procedure similar to that described for Example 9, steps c, d. LCMS: Method A, 3.979 min, MS: ES+ 330.95; $^1$H NMR (400 MHz, $CDCl_3$) δ ppm 7.73-7.75 (m, 1H), 7.53-7.56 (m, 1H), 7.44-7.48 (m, 1H), 7.39-7.43 (m, 2H), 6.88 (br s, 1H), 3.45-3.63 (m, 5H), 3.23-3.28 (m, 1H), 2.61-2.69 (m, 1H), 2.09-2.16 (m, 1H), 1.77-1.84 (m, 1H).

Example 67 (R)-3-(4-Chlorophenyl)-N-((1-cyanopyrrolidin-3-yl)methyl)isoxazole-5-carboxamide

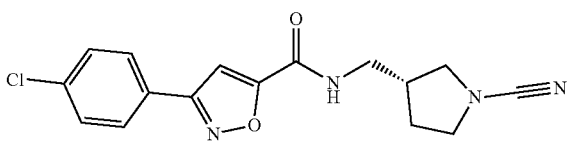 [SMILES: N#CN1CC[C@H](CNC(=O)c2cc(-c3ccc(Cl)cc3)no2)C1]

The title compound was synthesised by a procedure similar to Example 66. LCMS: Method A, 4.200 min, MS: ES+ 331.02; $^1$H NMR (400 MHz, $CDCl_3$) δ ppm 7.73-7.75 (m, 1H), 7.53-7.56 (m, 1H), 7.44-7.48 (m, 1H), 7.39-7.43 (m, 2H), 6.88 (br s, 1H), 3.45-3.63 (m, 5H), 3.23-3.28 (m, 1H), 2.61-2.69 (m, 1H), 2.09-2.16 (m, 1H), 1.77-1.84 (m, 1H).

Example 68 (R)-5-(3-Cyanophenyl)-N-((1-cyanopyrrolidin-3-yl)methyl)-1,3,4-oxadiazole-2-carboxamide

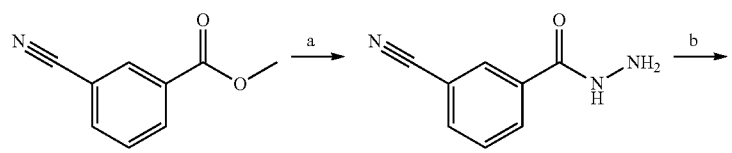

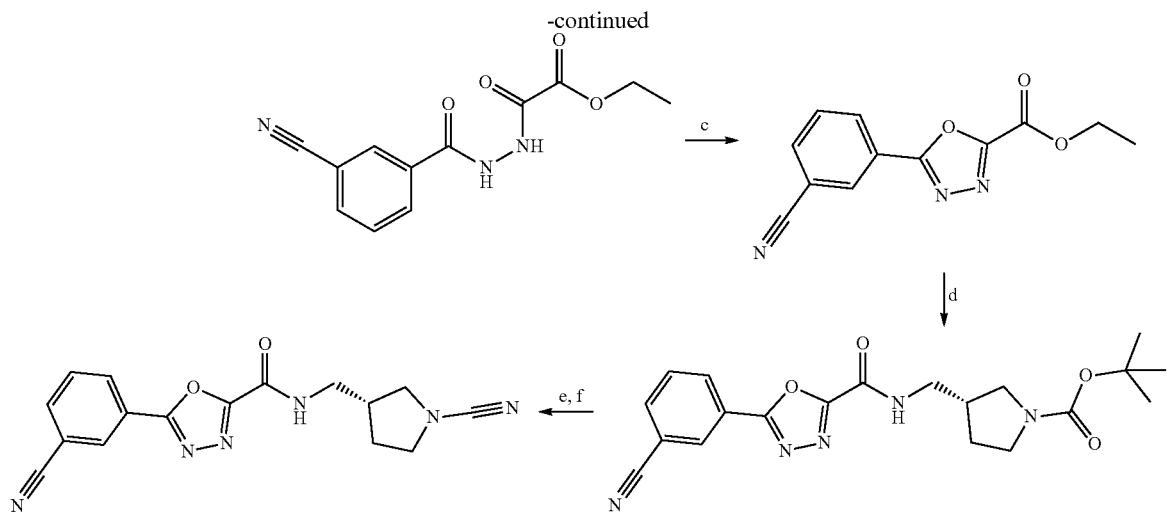

-continued

Step a. To a stirred solution of methyl 3-cyanobenzoate (CAS Number 13531-48-1; 4.000 g, 24.84 mmol) in MeOH (40 ml) was added hydrazine hydrate (3.1 ml, 62.0 mmol) at 0° C. The reaction mixture was stirred at rt for 16 h. The resulting reaction mixture was concentrated under vacuum, diluted with water (200 ml) and extracted with DCM (2×200 ml). The combined organic layer was dried over $Na_2SO_4$, filtered and concentrated under reduced pressure. The resulting residue was purified by flash column chromatography (70% EtOAc in hexane) yielding 3-cyanobenzohydrazide (3.200 g, 19.87 mmol). LCMS: Method C, 0.934 min, MS: ES+ 162.36; $^1$H NMR (400 MHz, DMSO-$d_6$) δ ppm 9.99 (s, 1H), 8.21 (s, 1H), 8.13 (d, J=7.6 Hz, 1H), 8.00 (d, J=7.6 Hz, 1H), 7.69 (t, J=8.0 Hz, 1H), 4.58 (s, 2H).

Step b. To a stirred solution of 3-cyanobenzohydrazide (2.500 g, 15.52 mmol) in DCM (50 ml) was added TEA (13.1 ml, 93.2 mmol) at 0° C. The reaction mixture was stirred at 0° C. for 5 min before dropwise addition of ethyl chlorooxoacetate (3.8 ml, 34.2 mmol) at 0° C. The reaction mixture was stirred at rt for 2 h. The resulting reaction mixture was diluted with water (200 ml) and extracted with DCM (2×200 ml). The combined organic layer was dried over $Na_2SO_4$, filtered and concentrated under reduced pressure yielding ethyl 2-(2-(3-cyanobenzoyl)hydrazinyl)-2-oxoacetate (4.000 g, 15.32 mmol). This material was directly used for next step without any further purification. LCMS: Method C, 1.405 min, MS: ES-260.40.

Step c. To a stirred solution of ethyl 2-(2-(3-cyanobenzoyl)hydrazinyl)-2-oxoacetate (4.00 g, 15.32 mmol) in DCM (50 ml) was added TEA (6.8 ml, 48.6 mmol) at 0° C. The reaction mixture was stirred at 0° C. for 5 min before addition of 4-toluenesulfonyl chloride (4.60 g, 34.2 mmol) at 0° C. The reaction mixture was stirred at rt for 2 h. The resulting reaction mixture was diluted with water (200 ml) and extracted with DCM (2×200 ml). The combined organic layer was dried over $Na_2SO_4$, filtered and concentrated under reduced pressure. The resulting residue was purified by flash column chromatography (25% EtOAc in hexane) yielding ethyl 5-(3-cyanophenyl)-1,3,4-oxadiazole-2-carboxylate (2.20 g, 9.05 mmol). LCMS: Method C, 1.738 min, MS: ES+ 244.32.

Step d. To a stirred solution of 5-(3-cyanophenyl)-1,3,4-oxadiazole-2-carboxylate (0.280 g, 1.152 mmol) and tert-butyl (R)-3-(aminomethyl)pyrrolidine-1-carboxylate (CAS Number 199174-29-3; 0.345 g, 1.728 mmol) in THF (2.5 ml) was drop wise added a solution of TBD (0.313 mg, 2.304 mmol) in THF (2.5 ml) at 0° C. The reaction mixture was stirred at rt for 3 h. The resulting reaction mixture was diluted with water (100 ml) and extracted with EtOAc (2×100 ml). The combined organic layer was dried over $Na_2SO_4$, filtered and concentrated under reduced pressure. The resulting residue was purified by flash column chromatography (55% EtOAc in hexane) yielding tert-butyl (R)-3-((5-(3-cyanophenyl)-1,3,4-oxadiazole-2-carboxamido)-methyl)pyrrolidine-1-carboxylate (0.305 g, 0.768 mmol). LCMS: Method C, 1.890 min, MS: ES+ 398.50.

Step e. A stirred solution of tert-butyl (R)-3-((5-(3-cyanophenyl)-1,3,4-oxadiazole-2-carboxamido)-methyl)pyrrolidine-1-carboxylate (0.305 g, 0.768 mmol) in DCM (7 ml) was added TFA (0.91 ml) at rt. The reaction mixture was stirred at rt for 40 min. The resulting reaction mixture was concentrated under reduced pressure. The obtained residue was re-distilled with DCM (3×5 ml) and dried under high vacuum yielding (R)-5-(3-cyanophenyl)-N-(pyrrolidin-3-ylmethyl)-1,3,4-oxadiazole-2-carboxamide TFA salt (0.290 g, 0.705 mmol). LCMS: Method C, 1.345 min, MS: ES+ 298.46.

Step f. To a solution of (R)-5-(3-cyanophenyl)-N-(pyrrolidin-3-ylmethyl)-1,3,4-oxadiazole-2-carboxamide TFA salt (0.290 g, 0.705 mmol) in THF (7 ml) was added $K_2CO_3$ (0.292 g, 2.12 mmol) at rt. The reaction mixture was stirred at rt for 10 min. Cyanogen bromide (0.074 g, 0.705 mmol) was added to the reaction mixture at 0° C. The reaction mixture was stirred at rt for 45 min. The resulting mixture was poured into water (25 ml) and the obtained precipitates were collected by filtration and wash with water (25 ml). The obtained solid material was triturated using pentane (2×6 ml) and dried under vacuum yielded title compound (0.160 g, 0.480 mmol). LCMS: Method A, 2.965 min, MS: ES+340.10 [M+18+H$^+$]; $^1$H NMR (400 MHz, DMSO-$d_6$) δ ppm 9.55 (t, J=6.0 Hz, 1H), 8.50 (s, 1H), 8.40 (d, J=8.0 Hz, 1H), 8.16 (d, J=8.0 Hz, 1H), 7.86 (t, J=6.0 Hz, 1H), 3.42-3.48 (m, 3H), 3.33-3.39 (m, 2H), 3.17-3.21 (m, 1H), 2.52-2.55 (m, 1H), 1.95-2.01 (m, 1H), 1.67-1.74 (m, 1H).

Example 69 (S)-5-(3-Cyanophenyl)-N-((1-cyanopyrrolidin-3-yl)methyl)-1,3,4-oxadiazole-2-carboxamide

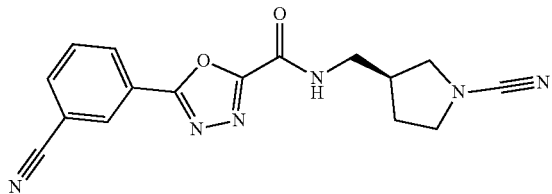 [SMILES: N#Cc1cccc(-c2nnc(C(=O)NC[C@@H]3CCN(C#N)C3)o2)c1]

The title compound was synthesised by a procedure similar to Example 68. LCMS: Method A, 3.071 min, MS: ES+ 340.10 [M+18+H⁺]; ¹H NMR (400 MHz, DMSO-d₆) δ ppm 9.55 (t, J=6.0 Hz, 1H), 8.50 (s, 1H), 8.40 (d, J=8.0 Hz, 1H), 8.16 (d, J=8.0 Hz, 1H), 7.86 (t, J=6.0 Hz, 1H), 3.42-3.48 (m, 3H), 3.33-3.39 (m, 2H), 3.17-3.21 (m, 1H), 2.52-2.55 (m, 1H), 1.95-2.01 (m, 1H), 1.67-1.74 (m, 1H).

Example 70 (R)—N-((1-Cyanopyrrolidin-3-yl)methyl)-1-phenyl-1H-imidazole-4-carboxamide

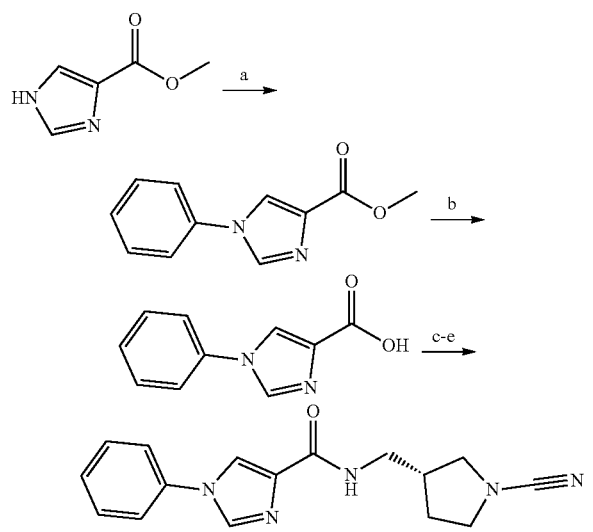

Step a. To a stirred solution of methyl 4-imidazolecarboxylate (CAS Number 17325-26-7; 0.500 g, 3.97 mmol) and 1,10-phenanthroline (1.400 g, 7.94 mmol) in DMSO (5 ml) was added iodobenzene (1.600 g, 7.94 mmol), Cs₂CO₃ (3.800 g, 11.9 mmol) and Cu₂O (0.567 g, 3.97 mmol) at rt in a microwave tube. The reaction mixture was heated at 100° C. for 15 min in microwave. The resulting reaction mixture was cooled to rt and filtered. The obtained filtrate was diluted with water (60 ml) and extracted with EtOAc (3×60 ml). The combined organic layer was dried over Na₂SO₄, filtered and concentrated under reduced pressure yielding methyl 1-phenyl-1H-imidazole-4-carboxylate (0.450 g, 2.23 mmol). This material was directly used for next step without any further purification. LCMS: Method C, 2.066 min, MS: ES+ 203.00.

Step b. To a stirred solution of methyl 1-phenyl-1H-imidazole-4-carboxylate (0.450 g, 2.23 mmol) in THF:water (9:1; 10 ml) was portion wise added NaOH (0.267 g, 6.68 mmol) at 0° C. The reaction mixture was stirred at rt for 16 h. The resulting mixture was diluted with ice cold water (60 ml) and acidified using 1 M HCl solution. The resulting mixture was extracted with EtOAc (3×60 ml). The combined organic layer was dried over Na₂SO₄, filtered and concentrated under reduced pressure yielding 1-phenyl-1H-imidazole-4-carboxylic acid (0.230 g, 1.22 mmol). This material was directly used in the next step without further purification. LCMS: Method C, 1.357 min, MS: ES+ 189.20.

Steps c-e. The title compound was synthesised from the intermediate above using a procedure similar to that described for Example 55. LCMS: Method B, 3.155 min, MS: ES+ 296.43; ¹H NMR (400 MHz, DMSO-d₆) δ ppm 8.40 (s, 1H), 8.37 (s, 1H), 8.25 (s, 1H), 7.73-7.75 (m, 2H), 7.52-7.56 (m, 2H), 7.41-7.43 (m, 1H), 3.37-3.44 (m, 4H), 3.24-3.28 (m, 2H), 3.15-3.19 (m, 1H), 1.89-1.94 (m, 1H), 1.64-1.69 (m, 1H).

Example 71 (R)-1-(3-Cyanophenyl)-N-((1-cyanopyrrolidin-3-yl)methyl)-1H-imidazole-4-carboxamide

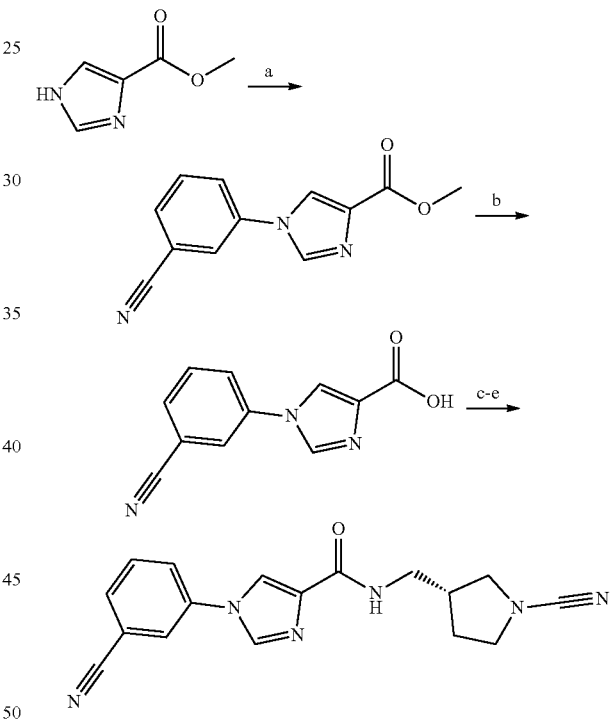

Step a. To a stirred solution of methyl 4-imidazolecarboxylate (CAS Number 17325-26-7; 1.000 g, 7.93 mmol) and 3-iodobenzonitrile (CAS Number 69113-59-3; 1.990 g, 8.72 mmol) in DMSO (15 ml) was added L-proline (0.180 g, 1.57 mmol), K₂CO₃ (2.290 g, 16.65 mmol) and CuI (0.154 g, 0.79 mmol) in a sealed tube. The reaction mixture was heated at 90° C. for 16 h. The resulting reaction mixture was cooled to rt, diluted with water (100 ml) and extracted with EtOAc (3×100 ml). The combined organic layer was dried over Na₂SO₄, filtered and concentrated under reduced pressure. The crude material was triturated using MTBE (3×10) and resulting material was dried under vacuum yielding methyl 1-(3-cyanophenyl)-1H-imidazole-4-carboxylate (0.400 g, 1.76 mmol). This material was directly used for next step without any further purification. LCMS: Method C, 1.483 min, MS: ES+ 228.36; ¹H NMR (400

MHz, DMSO-d$_6$) δ ppm 8.64 (s, 1H), 8.51 (s, 1H), 8.38 (s, 1H), 8.15 (dd, J=7.6, 1.6 Hz, 1H), 7.89 (d, J=8.0 Hz, 1H), 7.75 (t, J=8.0 Hz, 1H), 3.80 (s, 3H).

Step b. To a solution of methyl 1-(3-cyanophenyl)-1H-imidazole-4-carboxylate (0.400 g, 1.76 mmol) in THF:water (9:1; 10 ml) was portion wise added NaOH (0.211 g, 5.18 mmol) at rt. The reaction mixture was stirred at rt for 2 h. The resulting mixture diluted with water (30 ml) and extracted with EtOAc (2×50 ml). The aqueous layer was acidified using 1 M HCl and the obtained precipitates were collected by filtration and washed with hexane (10 ml). The obtained solid material was dried under high vacuum yielding 1-(3-cyanophenyl)-1H-imidazole-4-carboxylic acid (0.250 g, 1.173 mmol). This material was directly used for next step without any further purification. LCMS: Method C, 1.343 min, MS: ES+ 214.33.

Steps c-e. The title compound was synthesised from the intermediate above using a procedure similar to that described for Example 55. LCMS: Method A, 2.673 min, MS: ES+ 321.10; $^1$H NMR (400 MHz, DMSO-d$_6$) δ ppm 8.50 (s, 1H), 8.37-8.43 (m, 3H), 8.14 (dd, J=8.8, 1.6 Hz, 1H), 7.87 (d, J=8.8 Hz, 1H), 7.74 (d, J=8.0 Hz, 1H), 3.31-3.46 (m, 4H), 3.24-3.31 (m, 2H), 3.15-3.19 (m, 1H), 1.89-1.94 (m, 1H), 1.64-1.69 (m, 1H).

Example 72 (R)-1-(4-cyanophenyl)-N-((1-cyanopyrrolidin-3-yl)methyl)-1H-imidazole-4-carboxamide

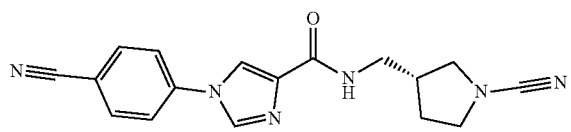 [SMILES: N#Cc1ccc(-n2cnc(C(=O)NC[C@H]3CCN(C#N)C3)c2)cc1]

The title compound was synthesised by a procedure similar to Example 71. LCMS: Method A, 2.693 min, MS: ES+ 321.15; $^1$H NMR (400 MHz, DMSO-d$_6$) δ ppm 8.56 (d, J=1.6 Hz, 1H), 8.44-8.45 (m, 1H), 8.43 (d, J=1.2 Hz, 1H), 8.00-8.06 (m, 4H), 3.37-3.44 (m, 2H), 3.24-3.31 (m, 2H), 3.15-3.19 (m, 1H), 2.51-2.53 (m, 2H), 1.89-1.93 (m, 1H), 1.64-1.69 (m, 1H).

Example 73 (R)—N-((1-Cyanopyrrolidin-3-yl)methyl)-1-(2-methoxyphenyl)-1H-imidazole-4-carboxamide

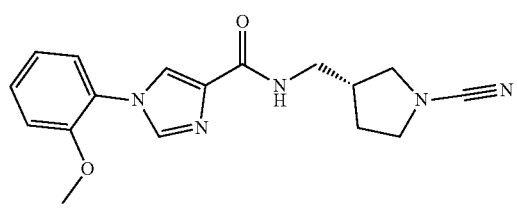 [SMILES: COc1ccccc1-n1cnc(C(=O)NC[C@H]2CCN(C#N)C2)c1]

The title compound was synthesised by a procedure similar to Example 71. LCMS: Method A, 2.963 min, MS: ES+ 326.20; $^1$H NMR (400 MHz, DMSO-d$_6$) δ ppm 8.33 (t, J=6.0 Hz, 1H), 7.98 (s, 1H), 7.87 (s, 1H), 7.44-7.48 (m, 2H), 7.28 (d, J=8.0 Hz, 1H), 7.09 (d, J=7.6 Hz, 1H), 3.84 (s, 3H), 3.49-3.51 (m, 4H), 3.24-3.27 (m, 2H), 3.15-3.19 (m, 1H), 1.87-1.95 (m, 1H), 1.59-1.71 (m, 1H).

Example 74 (R)—N-((1-Cyanopyrrolidin-3-yl)methyl)-1-(3-methoxyphenyl)-1H-imidazole-4-carboxamide

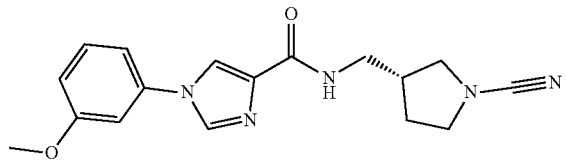 [SMILES: COc1cccc(-n2cnc(C(=O)NC[C@H]3CCN(C#N)C3)c2)c1]

The title compound was synthesised by a procedure similar to Example 71. LCMS: Method B, 3.202 min, MS: ES+ 326.53; $^1$H NMR (400 MHz, DMSO-d$_6$) δ ppm 8.38 (d, J=1.2 Hz, 1H), 8.34-8.37 (m, 1H), 8.28 (d, J=1.2 Hz, 1H), 7.43 (t, J=8.0 Hz, 1H), 7.30-7.33 (m, 2H), 6.97 (dd, J=8.8, 2.0 Hz, 1H), 3.85 (s, 3H), 3.35-3.44 (m, 4H), 3.25-3.28 (m, 2H), 3.15-3.19 (m, 1H), 1.89-1.94 (m, 1H), 1.65-1.70 (m, 1H).

Example 39 N-((1-Cyanopyrrolidin-3-yl)methyl)-6-(1-methyl-1H-pyrazol-4-yl)imidazo[1,2-a]pyridine-2-carboxamide

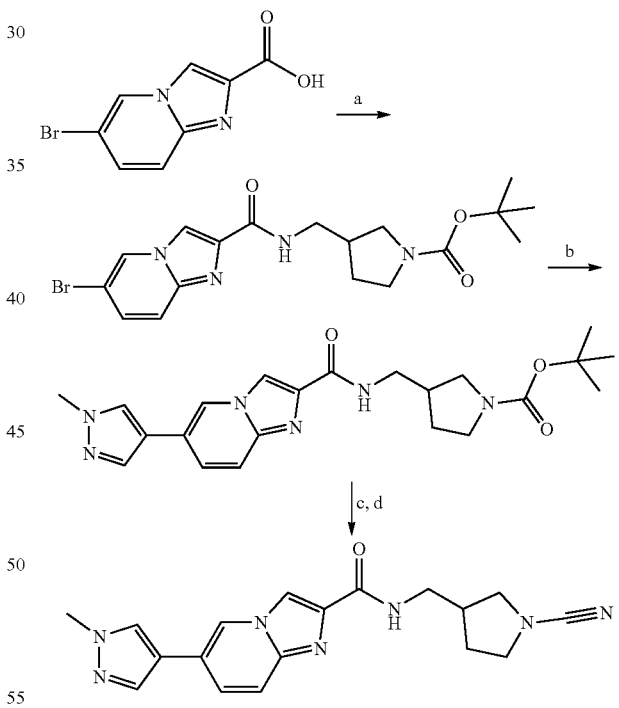

Step a. To a solution of 6-bromoimidazo[1,2-a]pyridine-2-carboxylic acid (CAS Number 749849-14-7; 1.0 g, 4.14 mmol) and tert-butyl 3-(aminomethyl)pyrrolidine-1-carboxylate (0.99 g, 4.97 mmol) in DMF (10 ml) were added DIPEA (1.1 ml, 6.22 mmol) and HATU (2.36 g, 6.22 mmol) at 0° C. The reaction mixture was stirred at rt for 2 h. The resulting reaction mixture was poured into water (200 ml) and extracted with EtOAc (4×50 ml). The combined organic phase was collected, dried over Na$_2$SO$_4$, filtered and concentrated under reduced pressure. The resulting residue was purified by column chromatography (2-3% MeOH in DCM)

yielding tert-butyl 3-((6-bromoimidazo[1,2-a]pyridine-2-carboxamido)methyl)pyrrolidine-1-carboxylate (1.75 g, 4.13 mmol). LCMS: Method C, 2.02 min, MS: ES+ 423.32; $^1$H NMR (400 MHz, DMSO-$d_6$) δ ppm 8.94 (s, 1H), 8.64 (t, J=6.0 Hz, 1H), 8.30 (s, 1H), 7.58 (d, J=9.6 Hz, 1H), 7.47 (dd, J=9.6, 1.6 Hz, 1H), 3.23-3.39 (m, 3H), 3.16-3.21 (m, 2H), 2.97-3.01 (m, 1H), 2.42-2.47 (m, 1H), 1.80-1.90 (m, 1H), 1.54-1.65 (m, 1H), 1.41 (s, 9H).

Step b. To a solution of tert-butyl 3-((6-bromoimidazo[1,2-a]pyridine-2-carboxamido)methyl) pyrrolidine-1-carboxylate (0.30 g, 0.70 mmol) and 1-methyl-4-(4,4,5,5-tetramethyl-1,3,2-dioxaborolan-2-yl)-1H-pyrazole (0.17 g, 0.85 mmol) in 1,4-dioxane:water (9:1; 8 ml) was added $K_2CO_3$ (0.195 g, 1.40 mmol) at rt. The reaction mixture was degassed for 10 min before addition of Pd(PPh$_3$)$_4$ (0.04 g, 0.035 mmol). The reaction mixture was heated at 100° C. for 16 h. The resulting reaction mixture was poured into water (150 ml) and extracted with EtOAc (3×50 ml). The combined organic phase was washed with brine solution (2×25 ml), dried over $Na_2SO_4$, filtered and concentrated under reduced pressure. The resulting residue was purified by column chromatography (2-3% MeOH in DCM) yielding tert-butyl 3-((6-(1-methyl-1H-pyrazol-4-yl)-imidazo[1,2-a]pyridine-2-carboxamido)methyl)pyrrolidine-1-carboxylate (0.15 g, 0.35 mmol). LCMS: Method C, 1.93 min, MS: ES+ 425.75; $^1$H NMR (400 MHz, DMSO-$d_6$) δ ppm 8.83 (s, 1H), 8.57 (t, J=6.00 Hz, 1H), 8.25 (s, 1H), 8.18 (s, 1H), 7.88 (s, 1H), 7.57-7.62 (m, 2H), 3.89 (s, 3H), 3.29-3.39 (m, 3H), 3.17-3.21 (m, 2H), 2.98-3.02 (m, 1H), 2.42-2.47 (m, 1H), 1.84-1.87 (m, 1H), 1.54-1.61 (m, 1H), 1.39 (s, 9H).

Steps c, d. The title compound was synthesised from the intermediate above using a procedure similar to that described for Example 9, steps c, d and purified by column chromatography (2-3% MeOH in DCM) yielding the title compound (0.028 g, 0.08 mmol). LCMS: Method C, 1.64 min, MS: ES+ 350.74; $^1$H NMR (400 MHz, DMSO-$d_6$) δ ppm 8.83 (s, 1H), 8.64 (t, J=6.4 Hz, 1H), 8.26 (s, 1H), 8.19 (s, 1H), 7.88 (s, 1H), 7.57-7.62 (m, 2H), 3.89 (s, 3H), 3.37-3.46 (m, 3H), 3.27-3.33 (m, 2H), 3.16-3.20 (m, 1H), 2.51-2.55 (m, 1H), 1.88-1.94 (m, 1H), 1.64-1.72 (m, 1H).

Example 75 (R)—N-((1-Cyanopyrrolidin-3-yl)methyl)-6-(H-pyrazol-4-yl)imidazo[1,2-a]pyridine-2-carboxamide The title compound was synthesised by a procedure similar to Example 39. LCMS: Method A, 2.148 min, MS: ES+ 336.08; $^1$H NMR (400 MHz, DMSO-$d_6$) δ ppm 13.05 (br s, 1H), 8.87 (s, 1H), 8.64 (t, J=6.0 Hz, 1H), 8.25 (s, 1H), 8.11 (br s, 2H), 7.59-7.67 (m, 2H), 3.40-3.47 (m, 3H), 3.29-3.36 (m, 2H), 3.17-3.20 (m, 1H), 2.54-2.56 (m, 1H), 1.90-1.95 (m, 1H), 1.66-1.71 (m, 1H).

Example 76 (R)—N-((1-Cyanopyrrolidin-3-yl)-6-(H-pyrazol-3-yl)imidazo[1,2-a]pyridine-2-carboxamide

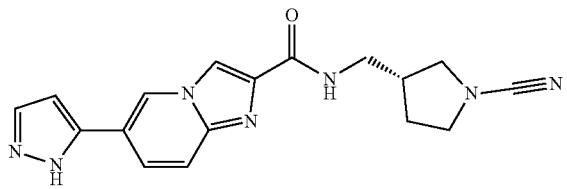 [SMILES: N#CN1CC[C@H](CNC(=O)c2cn3cc(-c4ccn[nH]4)ccc3n2)C1]

The title compound was synthesised by a procedure similar to Example 39. LCMS: Method A, 2.845 min, MS: ES+ 336.01; $^1$H NMR (400 MHz, DMSO-$d_6$) δ ppm 13.02 (s, 1H), 9.02 (s, 1H), 8.64 (t, J=6.0 Hz, 1H), 8.34 (s, 1H), 7.80-7.84 (m, 1H), 7.47-7.61 (m, 2H), 6.72 (s, 1H), 3.36-3.42 (m, 3H), 3.27-3.33 (m, 2H), 3.14-3.17 (m, 1H), 2.54-2.56 (m, 1H), 1.87-1.91 (m, 1H), 1.63-1.69 (m, 1H).

Example 77 (R)—N-((1-Cyanopyrrolidin-3-yl)methyl)-7-cyclopropylimidazo[1,2-a]pyridine-2-carboxamide

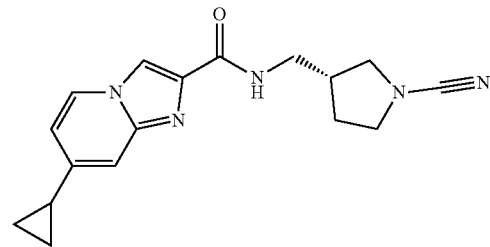 [SMILES: N#CN1CC[C@H](CNC(=O)c2cn3ccc(C4CC4)cc3n2)C1]

The title compound was synthesised by a procedure similar to Example 39. LCMS: Method B, 2.675 min, MS: ES+ 310.58; $^1$H NMR (400 MHz, DMSO-$d_6$) δ ppm 8.53 (br s, 1H), 8.41 (d, J=6.4 Hz, 1H), 8.21 (s, 1H), 7.25 (s, 1H), 6.62 (d, J=6.4 Hz, 1H), 3.32-3.37 (m, 2H), 3.22-3.26 (m, 2H), 3.14-3.16 (m, 1H), 2.49-2.53 (m, 2H) 1.99-2.01 (m, 1H), 1.87-1.89 (m, 1H), 1.63-1.66 (m, 1H), 0.98-1.00 (m, 2H), 0.72-0.79 (m, 2H).

Example 40 1-Benzyl-N-((1-cyanopyrrolidin-3-yl)methyl)-5-methyl-1H-pyrazole-3-carboxamide

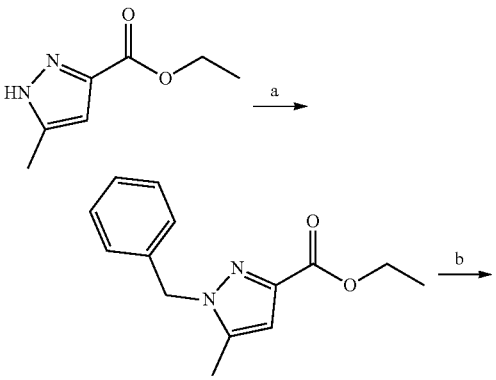

71
-continued

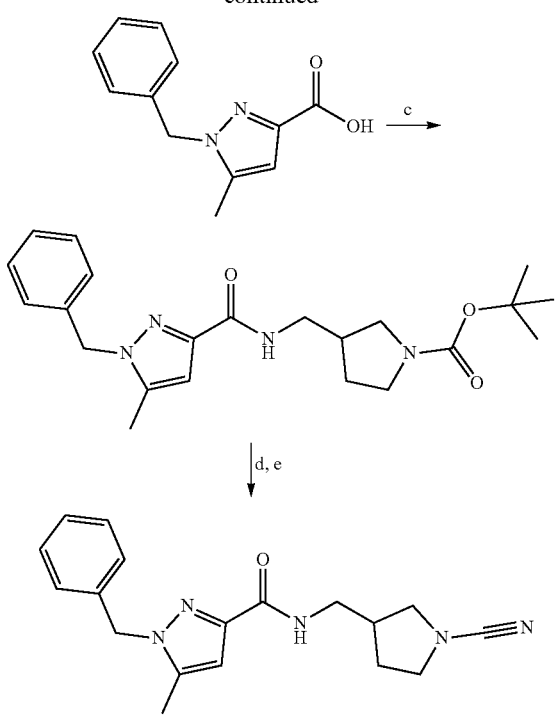

Step a. To a solution of ethyl 3-methyl-1H-pyrazole-5-carboxylate (CAS Number 4027-57-0; 1.50 g, 9.73 mmol) in THF (20 ml) was added KOH (0.65 g, 11.67 mmol) at rt. The reaction mixture was stirred at rt for 45 min. Benzyl bromide (1.16 ml, 9.73 mmol) was added dropwise to the reaction mixture at rt. The resulting reaction mixture was stirred at 70° C. for 16 h. The mixture was then poured into water (50 ml) and extracted with EtOAc (2×50 ml) and the combined organic phase was dried over $Na_2SO_4$, filtered and concentrated under reduced pressure. The resulting residue was purified by column chromatography (18% EtOAc in hexane) yielding ethyl 1-benzyl-5-methyl-1H-pyrazole-3-carboxylate (1.4 g, 5.734 mmol) LCMS: Method C, 2.27 min, MS: ES+ 245.4.

Step b. To a solution of ethyl 1-benzyl-5-methyl-1H-pyrazole-3-carboxylate (1.4 g, 5.73 mmol) in THF: water (16 ml: 4 ml) was added LiOH (1.20 g, 28.65 mmol) at rt. The reaction mixture was stirred at 50° C. for 16 h. The resulting reaction mixture was poured into water (50 ml) and extracted with ethyl acetate (2×100 ml). The aqueous layer was acidified using 1 M aqueous solution of HCl (5 ml) and extracted into EtOAc (2×50 ml). The combined organic phase was dried over $Na_2SO_4$, filtered and concentrated under reduced pressure yielding 1-benzyl-5-methyl-1H-pyrazole-3-carboxylic acid (1.10 g, 5.09 mmol). This material was directly used for the next step without further purification. LCMS: Method C, 1.89 min, MS: ES+ 217.29.

Steps c-e. The title compound was synthesised from the intermediate above using a procedure similar to that described for Example 20, steps a-c. LCMS: Method B, 3.68 min, MS: ES+ 324.6; $^1$H NMR (400 MHz, DMSO-$d_6$) δ ppm 8.29 (t, J=6 Hz, 1H), 7.26-7.37 (m, 3H), 7.11 (d, J=7.2 Hz, 2H), 6.47 (s, 1H), 5.36 (s, 2H), 3.29-3.43 (m, 3H), 3.20 (t, J=6.4 Hz, 2H), 3.12-3.16 (m, 1H), 2.42-2.46 (m, 1H), 2.21 (s, 3H), 1.85-1.93 (m, 1H), 1.59-1.68 (m, 1H).

72
Example 78 (R)-1-Benzyl-N-((1-cyanopyrrolidin-3-yl)methyl)-1H-imidazole-4-carboxamide

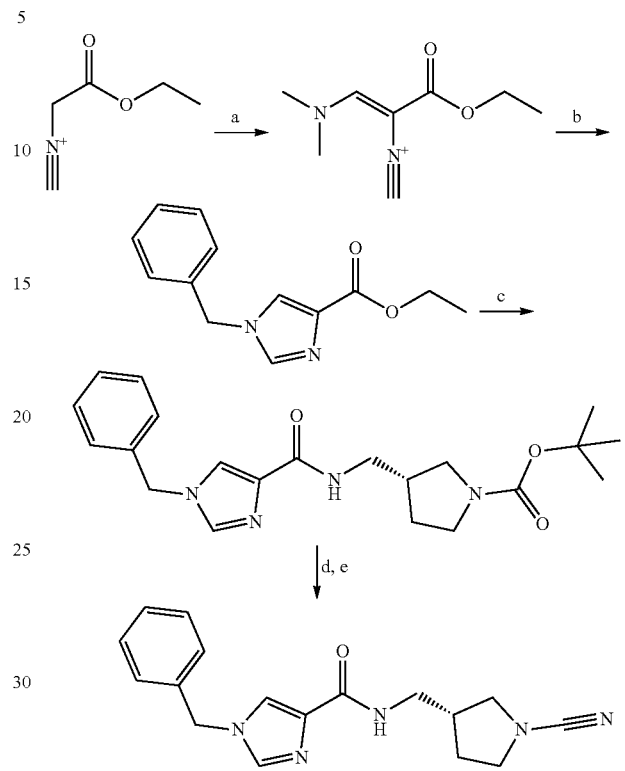

Step a. A mixture of tert-butoxybis(dimethylamino)methane (CAS Number 5815-08-7; 3.500 g, 20.11 mmol) and ethyl isocyanoacetate (CAS Number 2999-46-4; 2.270 g, 20.11 mmol) was stirred at rt for 2 h. The reaction mixture was concentrated under reduced pressure and the resulting residue was purified by flash column chromatography (15% EtOAc in hexane) yielding 1-(dimethylamino)-3-ethoxy-N-methylidyne-3-oxoprop-1-en-2-aminium (1.900 g, 11.24 mmol). LCMS: Method C, 1.570 min, MS: ES+ 169.43

Step b. A mixture of 1-(dimethylamino)-3-ethoxy-N-methylidyne-3-oxoprop-1-en-2-aminium (0.500 g, 2.98 mmol) and benzylamine (1.500 g, 14.9 mmol) was heated at 90° C. for 2 h. The resulting reaction mixture was cooled to rt, diluted with water (20 ml) and extracted with EtOAc (3×50 ml). The combined organic layer was washed with brine solution (20 ml), dried over $Na_2SO_4$, filtered and concentrated under reduced pressure yielding ethyl 1-benzyl-1H-imidazole-4-carboxylate (0.530 g, 2.30 mmol). This material was directly used for next step without any further purification. LCMS: Method C, 1.580 min, MS: ES+ 231.36

Step c. To a stirred solution of ethyl 1-benzyl-1H-imidazole-4-carboxylate (0.350 g, 1.52 mmol) and tert-butyl (R)-3-(aminomethyl)pyrrolidine-1-carboxylate (CAS Number 199174-29-3; 0.365 g, 1.826 mmol) in THF (5 ml) was added DIPEA (0.84 ml, 4.56 mmol) at rt. Trimethyl aluminium (2M in toluene; 3.8 ml, 7.6 mmol) was added dropwise to the reaction mixture at rt and then heated at 70° C. for 16 h. The reaction mixture was cooled to rt, diluted with water (20 ml) and $NH_4Cl$ solution (20 ml). The mixture was extracted with EtOAc (3×50 ml) and the combined organic layer was dried over $Na_2SO_4$, filtered and concentrated under reduced pressure. The resulting residue was purified by flash column chromatography (2% MeOH in DCM) yielding tert-butyl (R)-3-((1-benzyl-1H-imidazole-4-carboxamido)methyl)pyrrolidine-1-carboxylate (0.410 g, 1.067 mmol). LCMS: Method C, 1.405 min, MS: ES+ 285.48 [M-100]

Steps d, e. The title compound was synthesised from the intermediate above using a procedure similar to that described for Example 9, steps c, d. LCMS: Method A, 2.789 min, MS: ES+ 310.10; $^1$H NMR (400 MHz, DMSO-$d_6$) δ ppm 8.19 (t, J=6.0 Hz, 1H), 7.85 (s, 1H), 7.70 (s, 1H), 7.31-7.39 (m, 5H), 5.23 (s, 2H), 3.33-3.43 (m, 3H), 3.28-3.34 (m, 2H), 3.11-3.21 (m, 1H), 2.41-2.46 (m, 1H), 1.83-1.92 (m, 1H), 1.58-1.67 (m, 1H).

Example 79 (R)—N-((1-Cyanopyrrolidin-3-yl)methyl)-1-(cyclopropylmethyl)-1H-imidazole-4-carboxamide

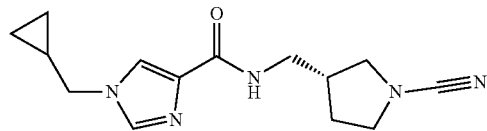 [SMILES: N#CN1CC[C@H](CNC(=O)c2cn(CC3CC3)cn2)C1]

The title compound was synthesised by a procedure similar to Example 78. LCMS: Method B, 2.583 min, MS: ES+ 274.48; $^1$H NMR (400 MHz, DMSO-$d_6$) δ ppm 8.16 (s, 1H), 7.73 (s, 2H), 3.84-3.86 (m, 2H), 3.32-3.40 (m, 3H), 3.15-3.22 (m, 3H), 2.49-2.50 (m, 1H), 1.87-1.90 (m, 1H), 1.62-1.70 (m, 1H), 1.18-1.22 (m, 1H), 0.50-0.60 (m, 2H), 0.34-0.40 (m, 2H).

Example 41 1-(3-Chlorophenyl)-3-((1-cyanopyrrolidin-3-yl)methyl)urea

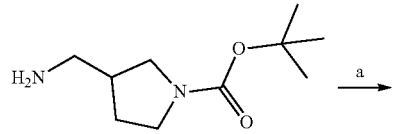

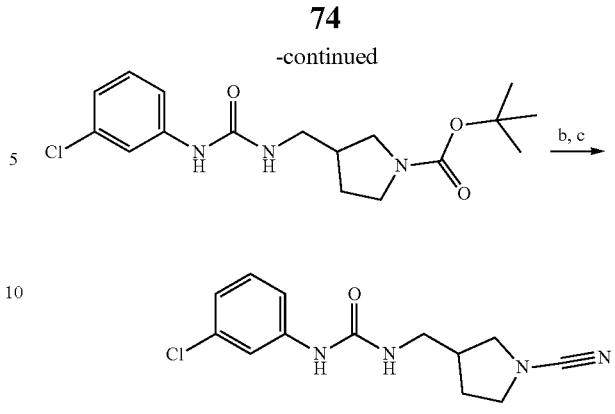

Step a. To a solution of 1-chloro-3-isocyanatobenzene (0.2 mmol) in DCM (1 mL) was added tert-butyl 3-(aminomethyl)pyrrolidine-1-carboxylate (0.2 mmol) and DIPEA (0.6 mmol). The reaction mixture was stirred at rt for 16 h. The mixture was concentrated under reduced pressure and the resulting residue was purified by prep-TLC (PE:EtOAc 1:2) yielding tert-butyl 3-((3-(3-chlorophenyl)ureido)methyl)-pyrrolidine-1-carboxylate. MS: ES+ 354.8.

Step b, c. The title compound was synthesised from the intermediate above using a procedure similar to that described for Example 1, steps b, c to provide the title compound (5.03 mg, 0.018 mmol). LCMS: Method E, retention time 2.56 min, MS: ES+ 279.0.

Compounds in Table 4 were synthesised using a procedure similar to that described for Example 41.

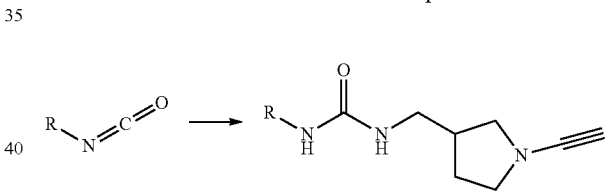

TABLE 4

| Ex | R | Name | LCMS Method | LCMS RT (min) | MS ES+ |
|---|---|---|---|---|---|
| 42 | ![F, methyl substituted phenyl] | 1-((1-Cyanopyrrolidin-3-yl)methyl)-3-(2-fluoro-5-methylphenyl)urea | F | 2.30 | 277.0 |
| 43 | ![benzylphenyl] | 1-(3-Benzylphenyl)-3-((1-cyanopyrrolidin-3-yl)methyl)urea | E | 2.85 | 335.0 |

TABLE 4-continued

| Ex | R | Name | LCMS Method | LCMS RT (min) | MS ES+ |
|---|---|---|---|---|---|
| 44 | 2,4-dichlorophenyl | 1-((1-Cyanopyrrolidin-3-yl)methyl)-3-(2,4-dichlorophenyl)urea | E | 3.09 | 313.0 |
| 45 | 4-(trifluoromethyl)phenyl | 1-((1-Cyanopyrrolidin-3-yl)methyl)-3-(4-(trifluoromethyl)phenyl)urea | E | 2.90 | 313.0 |

Example 46 N-((1-Cyanopyrrolidin-3-yl)methyl)-N-methyl-3-(2-methylthiazol-4-yl)-benzenesulfonamide

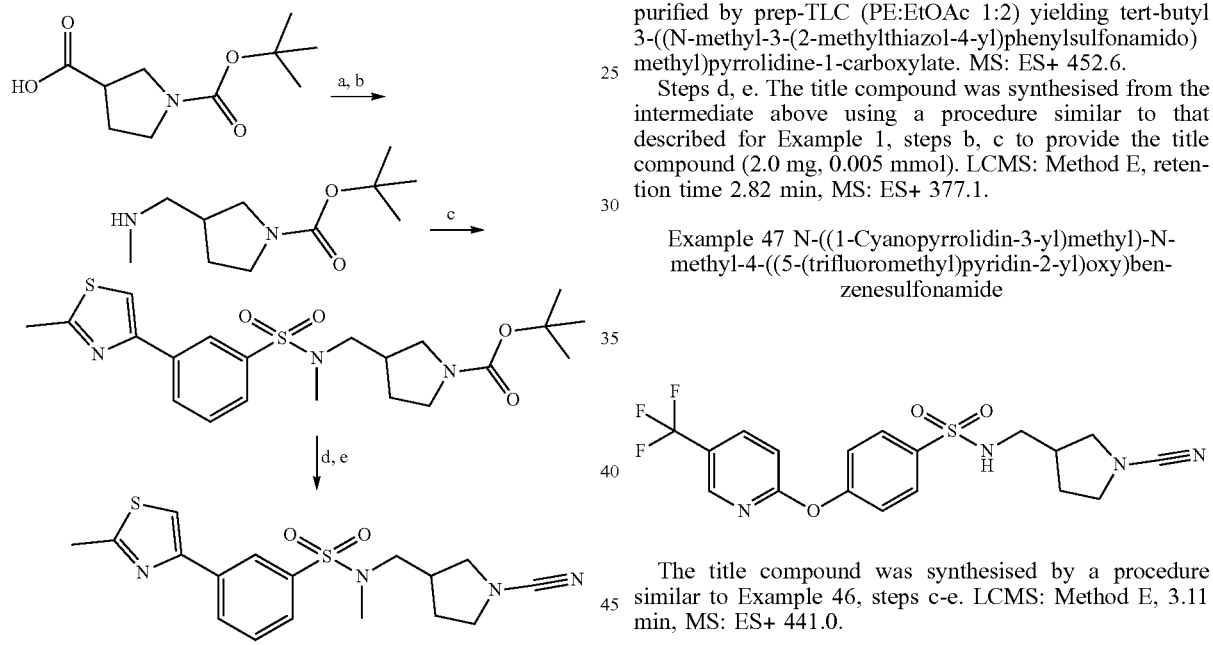

Steps a, b. See the procedure described for Example 37, steps a, b.

Step c. To a solution of 3-(2-methylthiazol-4-yl)benzene-1-sulfonyl chloride (0.2 mmol) in DCM (1 ml) was added tert-butyl 3-((methylamino)methyl)pyrrolidine-1-carboxylate (0.2 mmol) and DIPEA (0.6 mmol). The reaction mixture was stirred at rt for 16 h. The resulting mixture was concentrated under reduced pressure and the residue was purified by prep-TLC (PE:EtOAc 1:2) yielding tert-butyl 3-((N-methyl-3-(2-methylthiazol-4-yl)phenylsulfonamido)methyl)pyrrolidine-1-carboxylate. MS: ES+ 452.6.

Steps d, e. The title compound was synthesised from the intermediate above using a procedure similar to that described for Example 1, steps b, c to provide the title compound (2.0 mg, 0.005 mmol). LCMS: Method E, retention time 2.82 min, MS: ES+ 377.1.

Example 47 N-((1-Cyanopyrrolidin-3-yl)methyl)-N-methyl-4-((5-(trifluoromethyl)pyridin-2-yl)oxy)benzenesulfonamide The title compound was synthesised by a procedure similar to Example 46, steps c-e. LCMS: Method E, 3.11 min, MS: ES+ 441.0.

Example 48 3-(1-((6-(5-Methylisoxazol-4-yl)benzo[d]thiazol-2-yl)amino)ethyl)pyrrolidine-1-carbonitrile

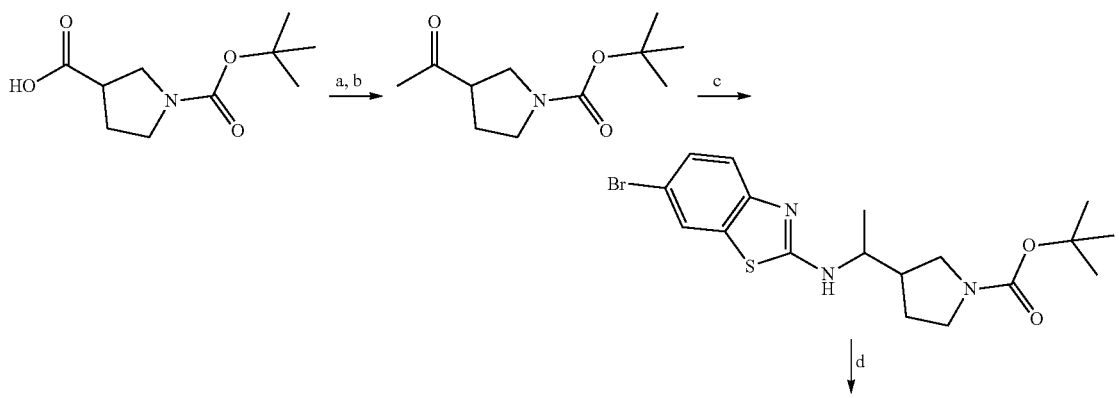

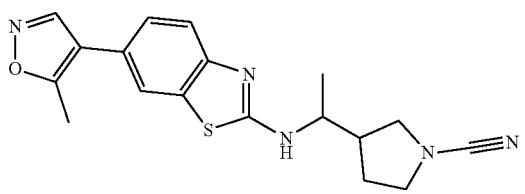 ← e, f 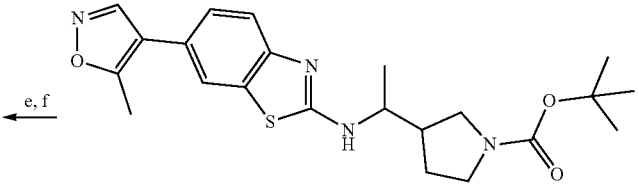

Step a. To a stirred solution of 1-(tert-butoxycarbonyl)pyrrolidine-3-carboxylic acid (3.0 g, 13.94 mmol) in DCM (70 ml) was added CDI (2.2 g, 13.94 mmol) at rt. The reaction mixture was stirred at rt for 1 h. N,O-Dimethyl hydroxylamine HCl (2.4 g, 245.1 mmol) was added at rt. The resulting mixture was stirred at rt for 16 h. The reaction mixture was poured into water (300 ml) and extracted with DCM (2×100 ml). The combined organic phase was dried over $Na_2SO_4$, filtered and concentrated under reduced pressure yielding tert-butyl 3-(methoxy(methyl)carbamoyl)pyrrolidine-1-carboxylate (4.0 g, quantitative). This material was used for the next step without further purification. LCMS: Method C, 1.91 min, MS: ES+ 259.31; $^1$H NMR (400 MHz, DMSO-$d_6$) δ ppm 3.69 (s, 3H), 3.44-3.50 (m, 3H), 3.19-3.28 (m, 2H), 3.11 (s, 3H), 1.94-2.08 (m, 1H), 1.86-1.91 (m, 1H), 1.40 (s, 9H).

Step b. A solution of tert-butyl 3-(methoxy(methyl)carbamoyl)pyrrolidine-1-carboxylate (4.0 g, 15.50 mmol) in THF (70 ml) was stirred at 0° C. under nitrogen. 3M $CH_3MgBr$ in diethyl ether (26 ml, 78 mmol) was added drop wise at 0° C. The reaction mixture was stirred at 0° C. for 30 min. The resulting reaction mixture was poured into saturated ammonium chloride solution (1 L) and extracted with EtOAc (2×200 ml). The combined organic phase was dried over $Na_2SO_4$, filtered and concentrated under reduced pressure yielding tert-butyl 3-acetylpyrrolidine-1-carboxylate (3.0 g, 14.08 mmol). This material was used for the next step without further purification. LCMS: Method A, 3.83 min, MS: ES+ 157.89 (M-56); $^1$H NMR (400 MHz, DMSO-$d_6$) δ ppm 3.77-3.40 (m, 2H), 3.22-3.25 (m, 3H), 2.17 (s, 3H), 2.03-2.11 (m, 1H), 1.85-1.94 (m, 1H), 1.39 (s, 9H).

Step c. To a stirred solution of tert-butyl 3-acetylpyrrolidine-1-carboxylate (0.5 g, 2.347 mmol) and 2-amino-6-bromobenzothiazole (0.43 g, 1.88 mmol) in THF (10 ml) was added titanium(IV) isopropoxide (3.33 g, 11.7 mmol) at 0° C. The reaction mixture was stirred at rt for 16 h. EtOH (4 ml) and sodium borohydride (0.26 g, 7.04 mmol) was added to the reaction mixture at 0° C. The reaction mixture was stirred at 80° C. for 8 h. The resulting reaction mixture was poured into water (100 ml) and filtered through celite hyflow. The resulting filtrate was extracted with EtOAc (2×70 ml). The combined organic phase was dried over $Na_2SO_4$, filtered and concentrated under reduced pressure. The resulting crude material was purified by flash chromatography (25% EtOAc in hexane) yielding tert-butyl 3-(1-((6-bromobenzo[d]thiazol-2-yl)amino)ethyl)pyrrolidine-1-carboxylate (0.18 g, 0.423 mmol). LCMS: Method A, 5.57 min, MS: ES+ 425.8, 427.8.

Step d. A solution of tert-butyl 3-(1-((6-bromobenzo[d]thiazol-2-yl)amino)ethyl)pyrrolidine-1-carboxylate (0.15 g, 0.352 mmol), 5-methyl-4-(4,4,5,5-tetramethyl-1,3,2-dioxaborolan-2-yl)isoxazole (0.29 g, 1.41 mmol) and $NaHCO_3$ (0.148 g, 1.76 mmol) in DMF:water (4:1; 5 ml) was stirred at rt in a microwaveable vial. The mixture was degassed for 30 min before addition of Pd(dppf)$Cl_2$ (0.025 g, 0.035 mmol) and the reaction mixture was heated to 90° C. for 1 h in a microwave. The resulting reaction mixture was poured into water (100 ml) and extracted with EtOAc (2×50 ml). The combined organic phase was dried over $Na_2SO_4$, filtered and concentrated under reduced pressure. The crude material was purified by flash chromatography (30% EtOAc in hexane) yielding tert-butyl 3-(1-((6-(5-methylisoxazol-4-yl)benzo[d]thiazol-2-yl)amino)ethyl)pyrrolidine-1-carboxylate (0.1 g, 0.233 mmol). LCMS: Method A, 4.95 min, MS: ES+ 429.10.

Steps e, f. The title compound was synthesised as mixture of diastereoisomers from the intermediate above using a procedure similar to that described for Example 1, steps b, c to provide the title compound yielding (0.03 g, 0.084 mmol). LCMS: Method A, 4.10 min, MS: ES+ 354.0; $^1$H NMR (400 MHz, DMSO-$d_6$) δ ppm 8.83 (s, 1H), 8.12 (d, J=8.4 Hz, 1H), 7.85 (s, 1H), 7.36-7.44 (m, 2H), 3.96-4.06 (m, 1H), 3.45-3.52 (m, 1H), 3.14-3.21 (m, 1H), 2.58 (s, 3H), 2.41-2.46 (m, 2H), 1.83-2.05 (m, 1H), 1.55-1.65 (m, 1H), 1.19 (d, J=6.4 Hz, 3H).

Example 49 3-(1-((6-(1H-Pyrazol-4-yl)benzo[d]thiazol-2-yl)amino)ethyl)pyrrolidine-1-carbonitrile

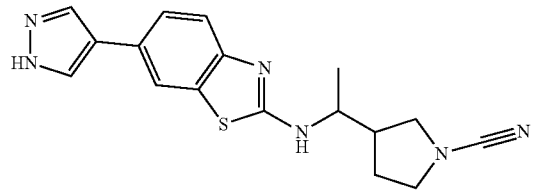 [SMILES: CC(Nc1nc2ccc(-c3cn[nH]c3)cc2s1)C1CCN(C#N)C1]

The title compound was synthesised by a procedure similar to Example 48. LCMS: Method A, 3.32 min, MS: ES+ 338.9; $^1$H NMR (400 MHz, DMSO-$d_6$) δ ppm 12.86 (s, 1H), 8.12 (s, 1H), 7.99 (dd, J=3, 8.4 Hz, 1H), 7.91 (t, J=2 Hz, 1H), 7.88 (s, 1H), 7.45-7.48 (m, 1H), 7.33 (dd, J=3, 8.4 Hz, 1H), 3.94-3.98 (m, 1H), 3.43-3.51 (m, 2H), 3.13-3.22 (m, 2H), 2.36-2.42 (m, 1H), 1.95-2.01 (m, 1H), 1.68-1.75 (m, 1H), 1.17-1.23 (m, 3H).

Example 50 3-(1-(Isoquinolin-3-ylamino)ethyl)pyrrolidine-1-carbonitrile

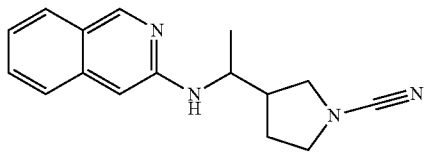 [SMILES: CC(Nc1cc2ccccc2cn1)C1CCN(C#N)C1]

The title compound was synthesised by a procedure similar to Example 48. LCMS: Method G, 24.90 min, 25.00 min, MS: ES+ 267.09; ¹H NMR (400 MHz, DMSO-d₆) δ ppm 8.84 (s, 1H), 7.78 (d, J=8.4 Hz, 1H), 7.51-7.54 (m, 1H), 7.43-7.47 (m, 1H), 7.12-7.16 (m, 1H), 6.611 (s, 1H), 6.41 (d, J=8.8 Hz, 1H), 3.88-3.97 (m, 1H), 3.41-3.53 (m, 2H), 3.76-3.99 (m, 1H), 3.12-3.20 (m, 1H), 2.35-2.43 (m, 1H), 1.97-2.02 (m, 1H), 1.65-1.76 (m, 1H), 1.30-1.67 (m, 3H).

Example 51 3-((1-(1-Cyanopyrrolidin-3-yl)ethyl)amino)isoquinoline-6-carbonitrile

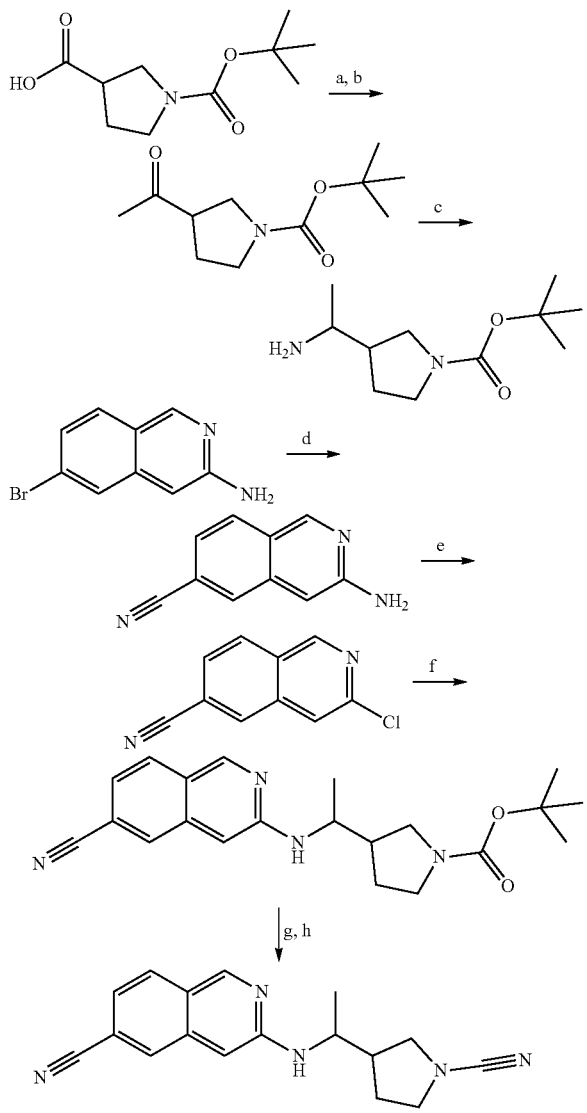

Step a. To a solution of 1-(tert-butoxycarbonyl)pyrrolidine-3-carboxylic acid (3.00 g, 13.95 mmol) in DCM (70 ml) was added CDI (2.26 g, 13.95 mmol) at 0° C. The reaction mixture was stirred at rt for 1 h. The reaction mixture was treated with N,O-dimethylhydroxylamine HCl (2.03 g, 2.09 mmol) and stirred for 12 h. The resulting reaction mixture was poured into water (50 ml) and extracted with DCM (3×40 ml). The combined organic phase was collected, dried over Na₂SO₄, filtered and concentrated under reduced pressure yielding tert-butyl 3-(methoxy(methyl)carbamoyl)pyrrolidine-1-carboxylate (3.20 g, 12.40 mmol). This material was directly used in the next step without further purification. LCMS: Method C, 1.90 min, MS: ES+ 259.40.

Step b. To a solution of tert-butyl 3-(methoxy(methyl)carbamoyl)pyrrolidine-1-carboxylate (3.20 g, 12.4 mmol) in THF (40 ml) was added 3M solution of CH₃MgBr in diethyl ether (21.0 ml, 63 mmol) at 0° C. The reaction mixture was stirred at rt for 2 h. The reaction mixture was cooled to 0° C. and quenched by dropwise addition of water (50 ml) followed by addition of EtOAc (50 ml). The resulting reaction mixture was filtered through celite hyflow and the celite bed was washed with EtOAc (3×20 ml). The filtrate was extracted with EtOAc (3×70 ml). The combined organic phase was collected, dried over Na₂SO₄, filtered and concentrated under reduced pressure. The resulting residue was purified by column chromatography (5% MeOH in DCM) yielding tert-butyl 3-acetylpyrrolidine-1-carboxylate (2.10 g, 9.84 mmol). LCMS: Method C, 1.93 min, MS: ES+ 214.30.

Step c. To a solution of tert-butyl 3-acetylpyrrolidine-1-carboxylate (0.70 g, 3.20 mmol) in MeOH (10 ml) was added ammonium acetate (0.91 g, 11.00 mmol) at 0° C. The reaction mixture was stirred at 0° C. for 1 h. NaCNBH₃ (0.60 g, 9.60 mmol) was added portion wise to the reaction mixture at 0° C.

The reaction mixture was stirred at rt for 16 h. The resulting reaction mixture was concentrated under reduced pressure, diluted with water (150 ml) and extracted with EtOAc (2×20 ml). The combined organic phase was collected, dried over Na₂SO₄, filtered and concentrated under reduced pressure yielding tert-butyl 3-(1-aminoethyl)pyrrolidine-1-carboxylate (0.47 g, 2.19 mmol) as a mixture of diastereomers. This material was directly used for the next step without further purification. LCMS: Method A, 3.54 & 3.67 min, MS: ES+ 215.10.

Step d. To a solution of 6-bromoisoquinolin-3-amine (0.80 g, 3.59 mmol) in DMA (10 ml) was added Zn(CN)₂ (2.09 g, 17.94 mmol) and Pd(PPh₃)₄ (1.24 g, 1.08 mmol). The reaction mixture was heated at 90° C. for 1 h. The resulting mixture was poured into water (100 ml) and extracted with EtOAc (3×100 ml). The combined organic phase was dried over Na₂SO₄, filtered and concentrated under reduced pressure. The resulting residue was purified by column chromatography (28% EtOAc in hexane) yielding 3-aminoisoquinoline-6-carbonitrile (0.57 g, 3.37 mmol). LCMS: Method C, 1.58 min, MS: ES+ 170.23; ¹H NMR (400 MHz, DMSO-d₆) δ ppm 8.94 (s, 1H), 8.19 (s, 1H), 7.95 (d, J=8.40 Hz, 1H), 7.34 (dd, J=8.40, 1.60 Hz, 1H), 6.67 (s, 1H), 6.34 (s, 2H).

Step e. A solution of 3-aminoisoquinoline-6-carbonitrile (0.56 g, 3.31 mmol) in concentrated HCl (3.2 ml) was stirred 0° C. for 15 min. NaNO₂ (0.22 g, 3.31 mmol) was added portion wise to the reaction mixture at 0° C. and stirred for 30 min. The resulting reaction mixture was poured into ice cold water (50 ml) and basified with saturated aqueous solution of NaHCO₃. The resulting mixture was extracted with EtOAc (3×60 ml). The combined organic phase was collected, dried over Na₂SO₄, filtered and concentrated under reduced pressure. The resulting residue was purified by column chromatography (8% EtOAc in hexane) yielding 3-chloroisoquinoline-6-carbonitrile (0.40 g, 2.11 mmol). LCMS: Method C, 2.15 min, MS: ES+ 189.04; ¹H NMR (400 MHz, DMSO-d₆) δ ppm 9.39 (s, 1H), 8.63 (s, 1H), 8.39 (d, J=8.40 Hz, 1H), 8.17 (s, 1H), 8.02 (dd, J=8.80, 1.60 Hz, 1H).

Step f. To a solution of 3-chloroisoquinoline-6-carbonitrile (0.25 g, 1.33 mmol) and tert-butyl 3-(1-aminoethyl)pyrrolidine-1-carboxylate (0.42 g, 1.99 mmol) in toluene (5 ml) was added t-BuOK (0.29 g, 2.66 mmol) at rt. The reaction mixture was degassed for 15 min before addition of Pd$_2$(dba)$_3$ (0.12 g, 0.13 mmol) and Ruphos (0.06 g, 0.13 mmol) at rt. The reaction mixture was heated at 100° C. for 16 h. The resulting reaction mixture was poured into water (50 ml) and extracted with EtOAc (3×50 ml). The combined organic phase was washed with brine solution (50 ml), dried over Na$_2$SO$_4$, filtered and concentrated under reduced pressure. The resulting residue was purified by column chromatography (18% EtOAc in hexane) yielding tert-butyl 3-(1-((6-cyanoisoquinolin-3-yl)amino)ethyl)pyrrolidine-1-carboxylate (0.135 g, 0.36 mmol). LCMS: Method C, 2.58 min, MS: ES+ 367.53.

Steps g, h. The title compound was synthesised from the intermediate above using a procedure similar to that described for Example 9, steps c, d to provide (0.071 g, 0.24 mmol). LCMS: Method A, 4.28 min, MS: ES+ 292.17; $^1$H NMR (400 MHz, DMSO-d$_6$) δ ppm 8.98 (d, J=2.40 Hz, 1H), 8.16 (s, 1H), 7.96 (dd, J=8.40, 2.80 Hz, 1H), 7.32-7.36 (m, 1H), 6.85 (d, J=8.80 Hz, 1H), 6.71 (s, 1H), 3.95-3.97 (m, 1H), 3.36-3.49 (m, 3H), 3.14-3.16 (m, 1H), 2.34-2.49 (m, 1H), 1.97-1.99 (m, 1H), 1.67-1.69 (m, 1H), 1.15 (m, 3H).

Example 52 3-((Benzo[d]thiazol-2-ylamino)(cyano)methyl)pyrrolidine-1-carbonitrile

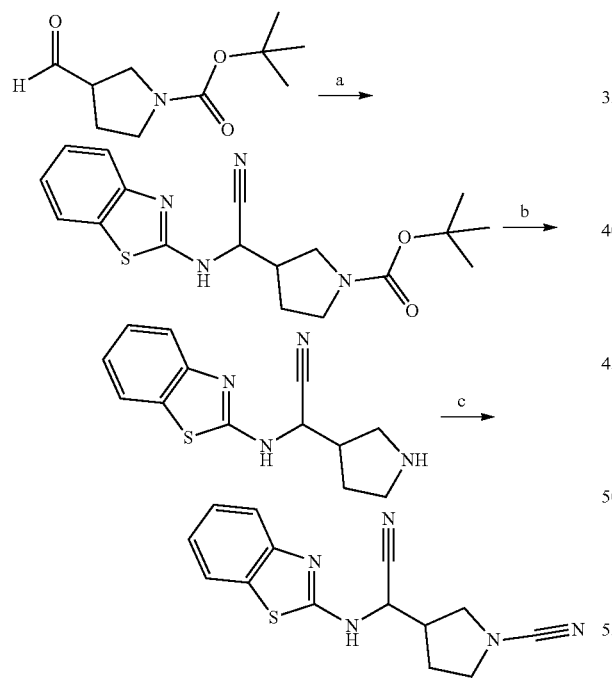

Step a. A mixture of 2-aminobenzothiazole (0.2 g, 1.33 mmol), 1-Boc-pyrrolidine-3-carboxaldehyde (0.53 g, 2.67 mmol) and Na$_2$SO$_4$ (1.0 g) in MeOH (15 ml) was stirred at rt for 24 h. Acetic acid (0.5 ml) was added to the reaction mixture and stirred at rt for an additional 24 h. The reaction mixture was filtered and excess of MeOH was distilled out. The obtained residue was dissolved in THF (5 ml) and lithium perchlorate (0.028 g, 0.267 mmol) was added at rt. Trimethylsilyl cyanide (0.263 g, 2.67 mmol) was added to reaction mixture at 0° C. The reaction mixture was stirred at rt for 5 h. Additional trimethylsilyl cyanide (0.16 g, 1.60 mmol) and phenol (0.15 g, 1.60 mmol) was added to the reaction mixture and heated to reflux for 16 h. The resulting reaction mixture was poured into saturated NaHCO$_3$ solution (50 ml) and extracted with EtOAc (3×15 ml). The combined organic phase was washed with water (20 ml). The organic phase was separated, dried over Na$_2$SO$_4$, filtered and concentrated under reduced pressure. The resulting residue was purified by flash chromatography (20% EtOAc in hexane) yielding tert-butyl 3-((benzo[d]thiazol-2-ylamino)(cyano)methyl)pyrrolidine-1-carboxylate (0.640 g, quantitative). MS: ES+ 359.25.

Step b. To a stirred solution of tert-butyl 3-((benzo[d]thiazol-2-ylamino)(cyano)methyl)pyrrolidine-1-carboxylate (0.32 g, 0.894 mmol) in DCM (10 ml) was added TFA (0.68 ml) at 0° C. The reaction mixture was stirred at rt for 16 h. The resulting reaction mixture was concentrated under reduced pressure. The resulting residue was azeotropically distilled using DCM (10 ml) yielding 2-(benzo[d]thiazol-2-ylamino)-2-(pyrrolidin-3-yl)acetonitrile TFA salt (0.657 g, quantitative). This material was used directly for the next step without further purification. LCMS: Method C, 1.57 min, 1.66 min, MS: ES+ 259.36.

Step c. To a solution of 2-(benzo[d]thiazol-2-ylamino)-2-(pyrrolidin-3-yl)acetonitrile TFA salt (0.65 g, 1.74 mmol) and K$_2$CO$_3$ (0.48 g, 3.49 mmol) in THF (10 ml) was added cyanogen bromide (0.28 g, 2.62 mmol) at -78° C. Five drops of TEA were added to the reaction mixture at -78° C. to pH 6. The reaction mixture was stirred at -78° C. The resulting reaction mixture was poured into water (20 ml) and extracted with EtOAc (3×15 ml). The combined organic phase was dried over Na$_2$SO$_4$, filtered and concentrated under reduced pressure. The resulting residue was purified by preparative HPLC [mobile phase: (A) 20 mM Ammonium acetate in water (B) MeCN, column: X Select Phenyl Hexyl 250×19 mm, 5 µm, flow rate: 16 ml/min] yielding 3-((benzo[d]thiazol-2-ylamino)-(cyano)methyl)pyrrolidine-1-carbonitrile (0.016 g, 0.056 mmol). LCMS: Method G, 22.80 min, 22.97 min, MS: ES+ 283.95; $^1$H NMR (400 MHz, DMSO-d$_6$) δ ppm 8.84 (s, 1H), 7.79 (d, J=8.0 Hz, 1H), 7.53 (dd, J=2.8 Hz, 8.0 Hz, 1H), 7.31 (t, J=8 Hz, 1H), 7.14 (t, J=7.6 Hz, 1H), 5.06-5.18 (m, 1H), 3.40-3.68 (m, 4H), 2.88-2.95 (m, 1H), 2.08-2.21 (m, 1H), 1.76-1.94 (m, 1H).

Example 53 2-((1-(1-Cyanopyrrolidin-3-yl)ethyl)amino)benzo[d]thiazole-6-carbonitrile

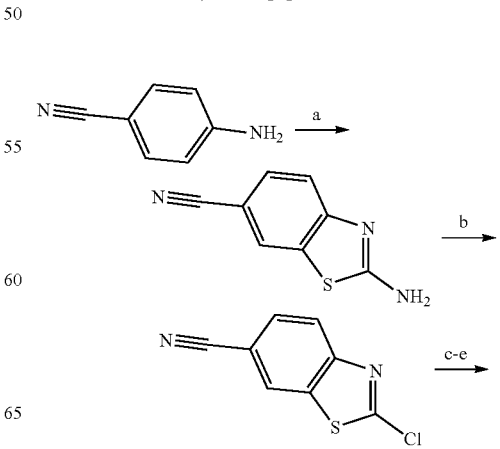

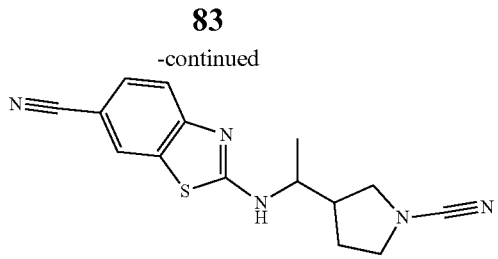

Step a. To a solution of 4-aminobenzonitrile (1.00 g, 8.47 mmol) in acetic acid (12 ml) was added potassium thiocyanate (1.00 g, 16.9 mmol) at 10° C. The reaction mixture was stirred at rt for 30 min. A solution of bromine (0.5 ml, 10.16 mmol) in acetic acid (3 ml) was added dropwise to the reaction at rt. The reaction mixture was stirred at rt for 16 h. The resulting solid precipitates were collected by filtration under reduced pressure, washed with acetic acid (10 ml) and dried under vacuum. The obtained precipitates were suspended in ice cold aqueous solution of $NH_4OH$ (10 ml) and stirred at rt for 30 min. The resulting solid precipitates were collected by filtration under reduced pressure, dried under vacuum yielding 2-aminobenzo[d]thiazole-6-carbonitrile (0.70 g, 4.00 mmol). This material was directly used in the next step without further purification. LCMS: Method C, 1.62 min, MS: ES+176.13.

Step b. To a solution of CuCl (0.13 g, 1.02 mmol) in MeCN (4 ml) was added tert butyl nitrite (0.24 g, 2.00 mmol) at 0° C. The reaction mixture was stirred at 0° C. for 10 min and then treated with 2-aminobenzo[d]thiazole-6-carbonitrile (0.18 g, 1.02 mmol). The reaction mixture was heated at 70° C. for 1 h. The resulting reaction mixture was poured into water (50 ml) and extracted with EtOAc (3×15 ml). The combined organic phase was dried over $Na_2SO_4$, filtered and concentrated under reduced pressure. The residue was triturated with n-pentane (2×5 ml) yielding 2-chloro-benzo[d]thiazole-6-carbonitrile (0.165 g, 0.84 mmol). This material was directly used in the next step without further purification. LCMS: Method C, 2.27 min, MS: ES+ 195; $^1$H NMR (400 MHz, DMSO-$d_6$) δ ppm 8.70 (s, 1H), 8.15 (d, J=8.40 Hz, 1H), 7.98 (d, J=8.40 Hz, 1H).

Step c-e. The title compound was synthesised from the intermediate above using a procedure similar to that described for Example 9, steps b-d. Method A, 3.90 min, MS: ES+ 298.1; $^1$H NMR (400 MHz, DMSO-$d_6$) δ ppm 8.58 (d, J=6.00 Hz, 1H), 8.20 (s, 1H), 7.62 (d, J=8.40 Hz, 1H), 7.45 (dd, J=8.40, 2.80 Hz, 1H), 3.99-4.02 (m, 1H), 3.42-3.51 (m, 2H), 3.36-3.39 (m, 1H), 3.13-3.20 (m, 1H), 2.41-2.44 (m, 1H), 1.97-1.99 (m, 1H), 1.65-1.73 (m, 1H), 1.20 (t, J=8.00 Hz, 3H).

Example 54 (3aR,6aS)-4-Oxo-5-(5-phenylthiazol-2-yl)hexahydropyrrolo[3,4-c]pyrrole-2(1H)-carbonitrile

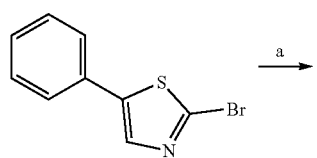

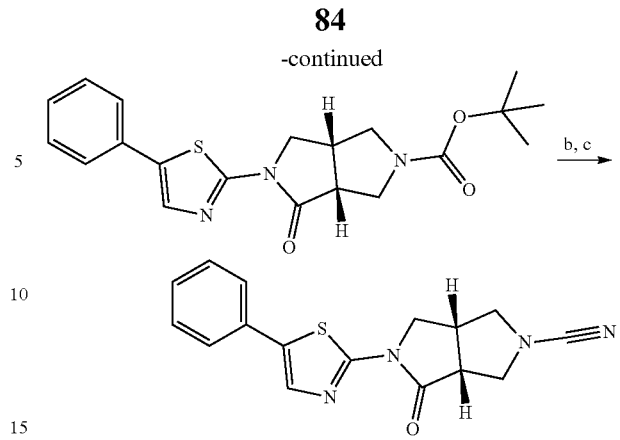

Step a. To a solution of 2-bromo-5-phenylthiazole (0.2 g, 0.83 mmol) in 1,4-dioxane (6 ml) was added tert-butyl (3aR,6aR)-4-oxohexahydropyrrolo[3,4-c]pyrrole-2(1H)-carboxylate (0.17 g, 0.75 mmol) at rt. CuI (0.03 g, 0.16 mmol), $K_3PO_4$ (0.71 g, 3.34 mmol) and N,N-dimethylethylenediamine (0.01 g, 0.16 mmol) were added to the reaction mixture at rt. The reaction mixture was heated at 100° C. for 4 h. The resulting reaction mixture was cooled to rt and poured into water (50 ml). The resulting mixture was extracted with EtOAc (3×20 ml). The organic phase was collected, dried over $Na_2SO_4$, filtered and concentrated under reduced pressure. The resulting residue was purified by solvent trituration using n-pentane (2×5 ml). The obtained material was dried under high vacuum to yield tert-butyl (3aR,6aS)-4-oxo-5-(5-phenylthiazol-2-yl)hexahydropyrrolo[3,4-c]pyrrole-2(1H)-carboxylate (0.19 g, 0.49 mmol), LCMS: Method C, 2.40 min, MS: ES+ 386.33.

Step b, c. The title compound was synthesised from the intermediate above using a procedure similar to that described for Example 9, steps c, d. LCMS: Method A, 4.15 min, MS: ES+ 310.93; $^1$H NMR (400 MHz, DMSO-$d_6$) δ ppm 7.97 (s, 1H), 7.65 (d, J=7.2 Hz, 2H), 7.43 (t, J=7.6 Hz, 2H), 7.33 (t, J=7.2 Hz, 1H), 4.16-4.21 (m, 1H), 4.01-4.04 (m, 1H), 3.62-3.71 (m, 3H), 3.55-3.56 (m, 1H), 3.44-3.48 (m, 1H), 3.21-3.25 (m, 1H).

BIOLOGICAL ACTIVITY OF COMPOUNDS OF THE INVENTION

Abbreviations

TAMRA carboxytetramethylrhodamine
PCR polymerase chain reaction
PBS phosphate buffered saline
EDTA ethylenediaminetetraacetic acid
Tris 2-amino-2-(hydroxymethyl)-1,3-propanediol
NP-40 Nonidet P-40, octylphenoxypolyethoxyethanol
BSA bovine serum albumin
PNS peripheral nervous system
BH3 Bcl-2 homology domain 3
PTEN phosphatase and tensin homologue
In Vitro USP30 Inhibition Assay
USP30 biochemical kinetic assay. Reactions were performed in duplicate in black 384 well plates (small volume, Greiner 784076) in a final reaction volume of 21 μl. USP30 CD (57-517, #64-0057-050 Ubiquigent) was diluted in reaction buffer (40 mM Tris, pH 7.5, 0.005% Tween 20, 0.5 mg/ml BSA, 5 mM beta-mercaptoethanol) to the equivalent of 0, 0.005, 0.01, 0.05, 0.1 and 0.5 l/well. Buffer was optimised for optimal temperature, pH, reducing agent, salts, time of incubation, and detergent. Reactions were initiated by the addition of 50 nM of TAMRA labelled peptide linked to ubiquitin via an iso-peptide bond as fluorescence polarisation substrate. Reactions were incubated at room temperature and read every 2 min for 120 min. Readings were performed on a Pherastar Plus (BMG Labtech). λ Excitation 540 nm; λ Emission 590 nm.

USP30 Biochemical IC50 Assay

Dilution plates were prepared at 21 times the final concentration (2100 μM for a final concentration of 100 μM) in 50% DMSO in a 96-well polypropylene V-bottom plate (Greiner #651201). A typical 8-point dilution series to be 100, 30, 10, 3, 1, 0.3, 0.1, 0.03 μM final. Reactions were performed in duplicate in black 384 well plates (small volume, Greiner 784076) in a final reaction volume of 21 μl. Either 1 μl of 50% DMSO or diluted compound was added to the plate. USP30 was diluted in reaction buffer (40 mM Tris, pH 7.5, 0.005% Tween 20, 0.5 mg/ml BSA, 5 mM beta-mercaptoethanol) to the equivalent of 0.05 μl/well and 10 μl of diluted USP30 was added to the compound. Enzyme and compound were incubated for 30 min at room temp. Reactions were initiated by the addition of 50 nM of TAMRA labelled peptide linked to ubiquitin via an iso-peptide bond as fluorescence polarisation substrate. Reactions were read immediately after addition of substrate and following a 2 hr incubation at room temperature. Readings were performed on a Pherastar Plus (BMG Labtech). λ Excitation 540 nm; λ Emission 590 nm.

Activity of Exemplary Compounds in USP30 biochemical IC50 assay

Ranges:
A<0.1 μM;
0.1<B<1 μM;
1<C<10 μM;
10<D<100 μM

| Example | IC50 range |
|---------|------------|
| 1 | C |
| 2 | C |
| 3 | C |
| 4 | D |
| 5 | B |
| 6 | C |
| 7 | C |
| 8 | C |
| 9 | A |
| 10 | B |
| 11 | B |
| 12 | C |
| 13 | C |
| 14 | C |
| 15 | C |
| 16 | C |
| 17 | C |
| 18 | B |
| 19 | C |
| 20 | B |
| 21 | B |
| 22 | B |
| 23 | B |
| 24 | B |
| 25 | B |
| 26 | B |
| 27 | B |
| 28 | A |
| 29 | C |
| 30 | B |
| 31 | B |
| 32 | B |
| 33 | B |
| 34 | C |
| 35 | C |
| 36 | C |
| 37 | B |
| 38 | B |
| 39 | C |
| 40 | C |
| 41 | B |
| 42 | B |
| 43 | B |
| 44 | B |
| 45 | B |
| 46 | B |
| 47 | B |
| 48 | B |
| 49 | B |
| 50 | C |
| 51 | C |
| 52 | B |
| 53 | C |
| 54 | C |
| 55 | A |
| 56 | C |
| 57 | C |
| 58 | B |
| 59 | B |
| 60 | B |
| 61 | B |
| 62 | B |
| 63 | B |
| 64 | B |
| 65 | C |
| 66 | B |
| 67 | B |
| 68 | A |
| 69 | A |
| 70 | C |
| 71 | A |
| 72 | B |
| 73 | B |
| 74 | B |
| 75 | C |
| 76 | C |
| 77 | B |
| 78 | B |
| 79 | C |

The invention claimed is:

1. A compound of formula (I):

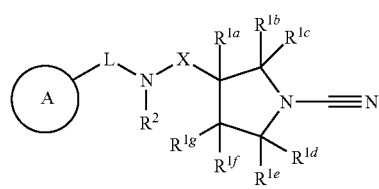

or a pharmaceutically acceptable salt thereof, wherein:
$R^{1b}$, $R^{1c}$, $R^{1d}$, $R^{1e}$ each independently represent hydrogen or an optionally substituted $C_1$-$C_6$ alkyl, or $R^{1b}$ is linked to $R^{1a}$ or $R^{1c}$ to form an optionally substituted cycloalkyl ring, or $R^{1e}$ is linked to $R^{1d}$ or $R^{1f}$ to form an optionally substituted cycloalkyl ring;

$R^{1a}$ and $R^{1g}$ each independently represent hydrogen, fluorine, cyano, hydroxyl, amino, optionally substituted $C_1$-$C_6$ alkyl or optionally substituted $C_1$-$C_6$ alkoxy, or $R^{1a}$ and $R^{1g}$ together form an optionally substituted cycloalkyl ring, or $R^{1a}$ is linked to $R^{1b}$ to form an optionally substituted cycloalkyl ring, or $R^{1g}$ is linked to $R^{1f}$ to form an optionally substituted cycloalkyl ring;

$R^{1f}$ represents hydrogen, fluorine, cyano, hydroxyl, amino, optionally substituted $C_1$-$C_6$ alkyl, optionally substituted $C_1$-$C_6$ alkoxy, or $R^{1f}$ is linked to $R^{1g}$ or $R^{1e}$ to form an optionally substituted cycloalkyl ring, or $R^{1f}$ together with $R^2$ forms an optionally further substituted heterocyclic ring;

$R^2$ represents hydrogen, optionally substituted $C_1$-$C_6$ alkyl or $R^2$ together with $R^{1f}$ forms an optionally further substituted heterocyclic ring;

X is $C(R^3)(R^4)$, wherein $R^3$ and $R^4$ each independently represent hydrogen, cyano, optionally substituted $C_1$-$C_6$ alkyl, a 5 or 6 membered heteroaryl or aryl ring or $R^3$ and $R^4$ together form a 3 to 6 membered heteroalkyl or cycloalkyl ring;

L represents a covalent bond, —SO—, —SO$_2$—, —C(O)—, —C(O)O—, —CONR$^5$—, —SO$_2$NR$^5$—, —C(O)—$C_1$-$C_6$ alkylene, —C(O)—$C_2$-$C_6$ alkenylene, $C_1$-$C_6$ alkylene-C(O)—, $C_2$-$C_6$ alkenylene-C(O)—, —$C_1$-$C_6$ alkylene-NR$^5$CO—, —$C_1$-$C_6$ alkylene-CONR$^5$—, optionally substituted $C_1$-$C_6$ alkylene or optionally substituted —$C_2$-$C_6$ alkenylene;

A represents a substituted monocyclic heteroaryl or aryl ring or an optionally substituted bicyclic heteroaryl or aryl ring;

$R^5$ represents hydrogen or optionally substituted $C_1$-$C_6$ alkyl.

2. The compound according to claim 1, wherein ring A is a 5 to 10 membered ring selected from oxazolyl, isoxazolyl, pyrazolyl, thiazolyl, pyridinyl, quinolinyl, benzothiazolyl, isoquinolinyl, pyrimidinyl, phenyl, benzomorpholinyl, indazolyl, imidazopyridinyl, quinazolinyl, pyrazolopyridinyl, benzimidazolyl, imidazolyl and oxadiazolyl.

3. The compound according to claim 1, wherein ring A is substituted with one or more -$Q^1$-$(R^6)_n$ wherein each occurrence -$Q^1$-$(R^6)_n$ is the same or different, wherein:

n is 0 or 1;

$Q^1$ represents halogen, cyano, oxo, nitro, —OR$^7$, —SR$^7$, —NR$^7$R$^8$, —CONR$^7$R$^8$, —NR$^7$CONR$^8$R$^9$, —COR$^7$, —C(O)OR$^7$, —SO$_2$R$^7$, —SO$_2$NR$^7$R$^8$, —NR$^7$SO$_2$R$^8$, NR$^7$SO$_2$NR$^8$R$^9$, —NR$^7$C(O)OR$^8$, optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, a covalent bond, an oxygen atom, a sulphur atom, —SO—, —SO$_2$—, —C(O)—, —C(O)O—, —CONR$^7$—, —NR$^7$—, —NR$^7$CO—, —NR$^7$CONR$^8$—, —SO$_2$NR$^7$—, —NR$^7$SO$_2$—, —NR$^7$SO$_2$NR$^8$—, —NR$^7$C(O)O—, —NR$^7$C(O)OR$^8$—, optionally substituted $C_1$-$C_6$ alkylene or optionally substituted —$C_2$-$C_6$ alkenylene;

$R^6$ is an optionally substituted 3 to 10 membered ring;

$R^7$, $R^8$ and $R^9$ each independently represent hydrogen, optionally substituted $C_1$-$C_6$ alkyl or optionally substituted $C_1$-$C_6$ alkylene.

4. The compound according to claim 3, wherein $R^6$ is a 3 to 10 membered heterocyclic, cycloalkyl, aryl or heteroaryl ring selected from phenyl, thiazolyl, pyridinyl, pyrrolidinyl pyrazolyl, isoindolyl, isoxazolyl and cyclopropyl.

5. The compound according to claim 3, wherein $R^6$ is substituted with one or more substituents selected from halogen, cyano, oxo, nitro, —OR$^{10}$, —SR$^{10}$, —NR$^{10}$R$^{11}$, —CONR$^{10}$R$^{11}$, —NR$^{10}$COR$^{11}$, —NR$^{10}$CONR$^{11}$R$^{12}$, —COR$^{10}$, —C(O)OR$^{10}$, —SO$_2$R$^{10}$, —SO$_2$NR$^{10}$R$^{11}$, —NR$^{10}$SO$_2$R$^{11}$, NR$^{10}$SO$_2$NR$^{11}$R$^{12}$, —NR$^{10}$C(O)OR$^{11}$, optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, -$Q^2$-R$^{10}$, -$Q^2$-NR$^{10}$CONR$^{11}$R$^{12}$, -$Q^2$-NR$^{10}$R$^{11}$, -$Q^2$-COR$^{10}$, -$Q^2$-NR$^{10}$COR$^{11}$, -$Q^2$-NR$^{10}$C(O)OR$^{11}$, -$Q^2$-SO$_2$R$^{10}$, $Q^2$-CONR$^{10}$R$^{11}$, -$Q^2$-CO$_2$R$^{10}$, -$Q^2$-SO$_2$NR$^{10}$R$^{11}$, -$Q^2$-NR$^{10}$SO$_2$R$^{11}$ and -$Q^2$-NR$^{10}$SO$_2$NR$^{11}$R$^{12}$;

$Q^2$ represents a covalent bond, an oxygen atom, a sulphur atom, —SO—, —SO$_2$—, —CO—, optionally substituted $C_1$-$C_6$ alkylene or optionally substituted $C_2$-$C_6$ alkenylene; and $R^{10}$, $R^{11}$, $R^{12}$ each independently represent hydrogen, optionally substituted $C_1$-$C_6$ alkyl, optionally substituted heterocyclyl, optionally substituted heteroaryl, optionally substituted aryl, or an optionally substituted cycloalkyl.

6. The compound according to claim 5, wherein $R^6$ is substituted with halogen, cyano, $C_1$-$C_4$ alkyl, $C_1$-$C_4$ alkoxy, wherein the alkyl and alkoxy is optionally substituted with one or more fluorine.

7. The compound according to claim 1, wherein $R^2$ is hydrogen or methyl.

8. The compound according to claim 1, wherein $C_1$-$C_6$ alkyl, $C_1$-$C_6$ alkoxy, $C_2$-$C_6$ alkenyl, $C_2$-$C_6$ alkynyl, $C_1$-$C_6$ alkylene, $C_2$-$C_6$ alkenylene, are each independently optionally substituted with one or more substituents selected from halogen, hydroxyl, thiol, cyano, amino, nitro and SF$_5$.

9. The compound according to claim 1, wherein $R^{1a}$, $R^{1b}$, $R^{1c}$, $R^{1d}$, $R^{1e}$, $R^{1f}$ and $R^{1g}$ are each hydrogen.

10. The compound according to claim 1, selected from the group consisting of:

3-((quinolin-2-ylamino)methyl)pyrrolidine-1-carbonitrile;

3-(((6-fluorobenzo[d]thiazol-2-yl)amino)methyl)pyrrolidine-1-carbonitrile;

3-((isoquinolin-1-ylamino)methyl)pyrrolidine-1-carbonitrile;

3-(((3-phenylpyridin-2-yl)amino)methyl)pyrrolidine-1-carbonitrile;

3-(((4-phenylpyridin-2-yl)amino)methyl)pyrrolidine-1-carbonitrile;

3-(((5-phenylpyridin-2-yl)amino)methyl)pyrrolidine-1-carbonitrile;

3-(((6-phenylpyridin-2-yl)amino)methyl)pyrrolidine-1-carbonitrile;

3-(((4-phenylpyrimidin-2-yl)amino)methyl)pyrrolidine-1-carbonitrile;

(R)-3-(((5-phenylthiazol-2-yl)amino)methyl)pyrrolidine-1-carbonitrile;

(S)-3-(((5-phenylthiazol-2-yl)amino)methyl)pyrrolidine-1-carbonitrile;

3-(((6-(1H-pyrazol-4-yl)benzo[d]thiazol-2-yl)amino)methyl)pyrrolidine-1-carbonitrile;

(R)-3-(((7-(1H-pyrazol-4-yl)quinazolin-2-yl)amino)methyl)pyrrolidine-1-carbonitrile;

3-(((3-(1,3-dimethyl-1H-pyrazol-4-yl)phenyl)amino)methyl)pyrrolidine-1-carbonitrile;

3-(((4-(1,3-dimethyl-1H-pyrazol-4-yl)phenyl)amino)methyl)pyrrolidine-1-carbonitrile;

3-(((4-(1,3-dimethyl-1H-pyrazol-4-yl)-2-fluorophenyl)amino)methyl)pyrrolidine-1-carbonitrile;

3-(((1-cyanopyrrolidin-3-yl)methyl)amino)isoquinoline-6-carbonitrile;

3-(((1-cyanopyrrolidin-3-yl)methyl)amino)-N-methylisoquinoline-6-carboxamide;

3-(((2-(isoindolin-2-yl)pyridin-4-yl)amino)methyl)pyrrolidine-1-carbonitrile;

(S)-3-(((4-phenylpyrimidin-2-yl)amino)methyl)pyrrolidine-1-carbonitrile;

N-((1-cyanopyrrolidin-3-yl)methyl)-2-phenyloxazole-5-carboxamide;

N-((1-cyanopyrrolidin-3-yl)methyl)-3-phenylisoxazole-5-carboxamide;
N-((1-cyanopyrrolidin-3-yl)methyl)-5-phenyl-1H-pyrazole-3-carboxamide;
N-((1-cyanopyrrolidin-3-yl)methyl)-4-methyl-3-oxo-3,4-dihydro-2H-benzo[b][1,4]oxazine-6-carboxamide;
N-((1-cyanopyrrolidin-3-yl)methyl)-4-(pyridin-4-yl)benzamide;
N-((1-cyanopyrrolidin-3-yl)methyl)-3-(o-tolyl)-1H-pyrazole-5-carboxamide;
N-((1-cyanopyrrolidin-3-yl)methyl)-2-phenylthiazole-4-carboxamide;
N-((1-cyanopyrrolidin-3-yl)methyl)-4-(pyrrolidin-1-yl)picolinamide;
N-((1-cyanopyrrolidin-3-yl)methyl)-1-(2,4-dichlorobenzyl)-1H-indazole-3-carboxamide;
1-benzyl-N-((1-cyanopyrrolidin-3-yl)methyl)-1H-indazole-3-carboxamide;
N-((1-cyanopyrrolidin-3-yl)methyl)-4-(N-phenylsulfamoyl)benzamide;
N-((1-cyanopyrrolidin-3-yl)methyl)-3-(2-fluorophenyl)-1H-pyrazole-5-carboxamide;
(E)-N-((1-cyanopyrrolidin-3-yl)methyl)-3-(2-fluoro-4-methoxyphenyl)acrylamide;
N-((1-cyanopyrrolidin-3-yl)methyl)-5-(4-fluorophenyl)nicotinamide;
(S)—N-((1-cyanopyrrolidin-3-yl)methyl)-3-oxo-3,4-dihydro-2H-benzo[b][1,4]oxazine-6-carboxamide;
(R)-6-chloro-N-((1-cyanopyrrolidin-3-yl)methyl)imidazo[1,2-a]pyridine-2-carboxamide;
(R)—N-((1-cyanopyrrolidin-3-yl)methyl)pyrazolo[1,5-a]pyridine-2-carboxamide;
2-([1,1'-biphenyl]-4-yl)-N-((1-cyanopyrrolidin-3-yl)methyl)-N-methylacetamide;
N-((1-cyanopyrrolidin-3-yl)methyl)-5-phenyloxazole-2-carboxamide;
N-((1-cyanopyrrolidin-3-yl)methyl)-6-(1-methyl-1H-pyrazol-4-yl)imidazo[1,2-a]pyridine-2-carboxamide;
1-benzyl-N-((1-cyanopyrrolidin-3-yl)methyl)-5-methyl-1H-pyrazole-3-carboxamide;
1-(3-chlorophenyl)-3-((1-cyanopyrrolidin-3-yl)methyl)urea;
1-((1-cyanopyrrolidin-3-yl)methyl)-3-(2-fluoro-5-methylphenyl)urea;
1-(3-benzylphenyl)-3-((1-cyanopyrrolidin-3-yl)methyl)urea;
1-((1-cyanopyrrolidin-3-yl)methyl)-3-(2,4-dichlorophenyl)urea;
1-((1-cyanopyrrolidin-3-yl)methyl)-3-(4-(trifluoromethyl)phenyl)urea;
N-((1-cyanopyrrolidin-3-yl)methyl)-N-methyl-3-(2-methylthiazol-4-yl)benzenesulfonamide;
N-((1-cyanopyrrolidin-3-yl)methyl)-N-methyl-4-((5-(trifluoromethyl)pyridin-2-yl)oxy)benzenesulfonamide;
3-(1-((6-(5-methylisoxazol-4-yl)benzo[d]thiazol-2-yl)amino)ethyl)pyrrolidine-1-carbonitrile;
3-(1-((6-(1H-pyrazol-4-yl)benzo[d]thiazol-2-yl)amino)ethyl)pyrrolidine-1-carbonitrile;
3-(1-(isoquinolin-3-ylamino)ethyl)pyrrolidine-1-carbonitrile;
3-(((1-(1-cyanopyrrolidin-3-yl)ethyl)amino)isoquinoline-6-carbonitrile;
3-((benzo[d]thiazol-2-ylamino)(cyano)methyl)pyrrolidine-1-carbonitrile;
2-((1-(1-cyanopyrrolidin-3-yl)ethyl)amino)benzo[d]thiazole-6-carbonitrile;
(3aR,6aS)-4-oxo-5-(5-phenylthiazol-2-yl)hexahydropyrrolo[3,4-c]pyrrole-2(1H)-carbonitrile;
(R)-3-(3-chlorophenyl)-N-((1-cyanopyrrolidin-3-yl)methyl)isoxazole-5-carboxamide;
(R)—N-((1-cyanopyrrolidin-3-yl)methyl)-1H-benzo[d]imidazole-2-carboxamide;
(R)—N-((1-cyanopyrrolidin-3-yl)methyl)isoquinoline-3-carboxamide;
(R)—N-((1-cyanopyrrolidin-3-yl)methyl)-5-phenylisoxazole-3-carboxamide;
(R)—N-((1-cyanopyrrolidin-3-yl)methyl)-4-phenylpicolinamide;
(R)—N-((1-cyanopyrrolidin-3-yl)methyl)-5-phenylpicolinamide;
(R)—N-((1-cyanopyrrolidin-3-yl)methyl)-5-phenylthiazole-2-carboxamide;
(R)—N-((1-cyanopyrrolidin-3-yl)methyl)-4-phenylthiazole-2-carboxamide;
(R)—N-((1-cyanopyrrolidin-3-yl)methyl)-1-phenyl-1H-pyrazole-3-carboxamide;
(R)—N-((1-cyanopyrrolidin-3-yl)methyl)-2-phenyl-1H-imidazole-5-carboxamide;
(R)-7-chloro-N-((1-cyanopyrrolidin-3-yl)methyl)imidazo[1,2-a]pyridine-2-carboxamide;
(R)-3-(2-chlorophenyl)-N-((1-cyanopyrrolidin-3-yl)methyl)isoxazole-5-carboxamide;
(R)-3-(4-chlorophenyl)-N-((1-cyanopyrrolidin-3-yl)methyl)isoxazole-5-carboxamide;
(R)-5-(3-cyanophenyl)-N-((1-cyanopyrrolidin-3-yl)methyl)-1,3,4-oxadiazole-2-carboxamide;
(S)-5-(3-cyanophenyl)-N-((1-cyanopyrrolidin-3-yl)methyl)-1,3,4-oxadiazole-2-carboxamide;
(R)—N-((1-cyanopyrrolidin-3-yl)methyl)-1-phenyl-1H-imidazole-4-carboxamide;
(R)-1-(3-cyanophenyl)-N-((1-cyanopyrrolidin-3-yl)methyl)-1H-imidazole-4-carboxamide;
(R)-1-(4-cyanophenyl)-N((1-cyanopyrrolidin-3-yl)methyl)-1H-imidazole-4-carboxamide;
(R)—N-((1-cyanopyrrolidin-3-yl)methyl)-1-(2-methoxyphenyl)-1H-imidazole-4-carboxamide;
(R)—N-((1-cyanopyrrolidin-3-yl)methyl)-1-(3-methoxyphenyl)-1H-imidazole-4-carboxamide;
(R)—N-((1-cyanopyrrolidin-3-yl)methyl)-6-(1H-pyrazol-4-yl)imidazo[1,2-a]pyridine-2-carboxamide;
(R)—N-((1-cyanopyrrolidin-3-yl)methyl)-6-(1H-pyrazol-3-yl)imidazo[1,2-a]pyridine-2-carboxamide;
(R)—N-((1-cyanopyrrolidin-3-yl)methyl)-7-cyclopropylimidazo[1,2-a]pyridine-2-carboxamide;
(R)-1-benzyl-N-((1-cyanopyrrolidin-3-yl)methyl)-1H-imidazole-4-carboxamide; and
(R)—N-((1-cyanopyrrolidin-3-yl)methyl)-1-(cyclopropylmethyl)-1H-imidazole-4-carboxamide, or a pharmaceutically acceptable salt thereof.

11. A process for the preparation of a compound of formula (I) or a pharmaceutically acceptable salt thereof as defined according to claim 1, comprising the steps of reacting an amine of formula (IV) with cyanogen bromide:

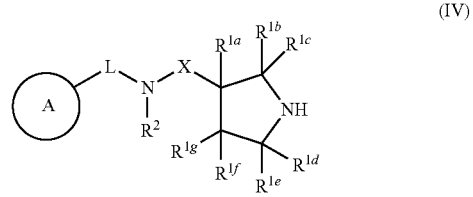

(IV)

wherein $R^{1a}$, $R^{1b}$, $R^{1c}$, $R^{1d}$, $R^{1e}$, $R^{1f}$, $R^{1g}$, $R^2$, ring A, L and X are defined according to claim 1.

12. A pharmaceutical composition, comprising a compound according to claim 1, or a pharmaceutically acceptable salt thereof, together with one or more pharmaceutically acceptable excipients.

\* \* \* \* \*

UNITED STATES PATENT AND TRADEMARK OFFICE
CERTIFICATE OF CORRECTION

PATENT NO. : 11,130,748 B2
APPLICATION NO. : 15/781615
DATED : September 28, 2021
INVENTOR(S) : Mark Ian Kemp et al.

It is certified that error appears in the above-identified patent and that said Letters Patent is hereby corrected as shown below:

In the Claims

Column 87, Line 38, -- -NR7COR8, -- should be inserted before "-NR7CONR8R9."

Signed and Sealed this
Nineteenth Day of April, 2022

*Katherine Kelly Vidal*

Katherine Kelly Vidal
*Director of the United States Patent and Trademark Office*